United States Patent
Yip et al.

(10) Patent No.: US 10,151,758 B2
(45) Date of Patent: Dec. 11, 2018

(54) METHODS FOR TOP-DOWN MULTIPLEXED MASS SPECTRAL ANALYSIS OF MIXTURES OF PROTEINS OR POLYPEPTIDES

(71) Applicant: Thermo Finnigan LLC, San Jose, CA (US)

(72) Inventors: Ping F. Yip, Salem, MA (US); James L. Stephenson, Jr., Raleigh, NC (US); John E. P. Syka, Charlottesville, VA (US)

(73) Assignee: THERMO FINNIGAN LLC, San Jose, CA (US)

( * ) Notice: Subject to any disclaimer, the term of this patent is extended or adjusted under 35 U.S.C. 154(b) by 141 days.

(21) Appl. No.: 15/406,626

(22) Filed: Jan. 13, 2017

(65) Prior Publication Data
US 2017/0205425 A1    Jul. 20, 2017

Related U.S. Application Data

(60) Provisional application No. 62/278,935, filed on Jan. 14, 2016.

(51) Int. Cl.
*G01N 33/68* (2006.01)
*H01J 49/00* (2006.01)

(52) U.S. Cl.
CPC ...... *G01N 33/6848* (2013.01); *H01J 49/0031* (2013.01); *H01J 49/0036* (2013.01); *H01J 49/0072* (2013.01)

(58) Field of Classification Search
None
See application file for complete search history.

(56) References Cited

U.S. PATENT DOCUMENTS

| | | |
|---|---|---|
| 5,175,430 A | 12/1992 | Enke et al. |
| 7,064,317 B2 | 6/2006 | McLuckey et al. |
| 7,355,169 B2 | 4/2008 | McLuckey et al. |
| 7,518,108 B2 | 4/2009 | Frey et al. |
| 7,550,718 B2 | 6/2009 | McLuckey et al. |
| 7,749,769 B2 | 7/2010 | Hunt et al. |
| 8,283,626 B2 | 10/2012 | Brown et al. |
| 8,334,503 B2 | 12/2012 | McLuckey et al. |
| 8,440,962 B2 | 5/2013 | Le Blanc |
| 2002/0172961 A1 | 11/2002 | Schneider et al. |
| 2004/0069943 A1 | 4/2004 | Kato |

(Continued)

FOREIGN PATENT DOCUMENTS

| | | |
|---|---|---|
| WO | 02/086490 A2 | 10/2002 |
| WO | 2008/151140 A2 | 12/2008 |

(Continued)

OTHER PUBLICATIONS

Coon et al., "Protein identification using sequential ionionreactions and tandem mass spectrometry", PNAS 2005, vol. 102 (27), 9463-9468.

(Continued)

*Primary Examiner* — Xiaoyun R Xu
(74) *Attorney, Agent, or Firm* — Thomas F. Cooney

(57) ABSTRACT

Applications of ion-ion reaction chemistry are disclosed in which proton transfer reactions (PTR) and real-time data analysis methods are used to (1) simplify complex mixture analysis of samples introduced into a mass spectrometer, and (2) improve resolution and sensitivity for the analysis of large proteins in excess of 50 kDa by removing charge and reducing the collisional cross section.

19 Claims, 54 Drawing Sheets

(56) References Cited

U.S. PATENT DOCUMENTS

| | | |
|---|---|---|
| 2004/0181351 A1 | 9/2004 | Thompson et al. |
| 2005/0098719 A1 | 5/2005 | Thomson |
| 2008/0093546 A1 | 4/2008 | Hartmer |
| 2008/0093547 A1 | 4/2008 | Hartmer et al. |
| 2008/0128607 A1 | 6/2008 | Herold et al. |
| 2011/0114835 A1 | 5/2011 | Chen et al. |
| 2011/0189788 A1 | 8/2011 | Brown et al. |
| 2011/0288779 A1 | 11/2011 | Satulovsky |
| 2012/0156707 A1 | 6/2012 | Hartmer et al. |
| 2012/0205531 A1 | 8/2012 | Zabrouskov |
| 2013/0084645 A1 | 4/2013 | Coon et al. |
| 2013/0240722 A1 | 9/2013 | Coon et al. |
| 2014/0120565 A1 | 5/2014 | Coon et al. |
| 2014/0326871 A1 | 11/2014 | Whitehouse et al. |
| 2014/0357502 A1 | 12/2014 | Campbell et al. |
| 2015/0293058 A1 | 10/2015 | Wuhr et al. |
| 2015/0380231 A1 | 12/2015 | Brown et al. |
| 2017/0162372 A1 | 6/2017 | Stephenson, Jr. et al. |

FOREIGN PATENT DOCUMENTS

| | | |
|---|---|---|
| WO | 2013/112677 A2 | 8/2013 |
| WO | 2013/166169 A1 | 11/2013 |
| WO | 2014/116711 A1 | 7/2014 |
| WO | 2014/150040 A2 | 9/2014 |
| WO | 2016/011355 A1 | 1/2016 |

OTHER PUBLICATIONS

Campbell et al., "Targeted Ion Parking for the Quantitation of Biotherapeutic Proteins: Concepts and Preliminary Data", J Am Soc Mass Spectrom 2010, 21, pp. 2011-2022.

Cargile et al., "Identification of Bacteriophage MS2 Coat Proteinfrom E. coli Lysates via Ion Trap Collisional Activation of Intact Protein Ions", Anal. Chem. 2001, 73, pp. 1277-1285.

Chrisman et al., "Parallel Ion Parking of Protein Mixtures", Anal. Chem. 2006, 78, pp. 310-316.

Chrisman et al., "Parallel Ion Parking: Improving Conversion of Parents to First-Generation Products in Electron Transfer Dissociation", Anal. Chem. 2005, 77 (10), pp. 3411-3414.

He et al., "Dissociation of Multiple Protein Ion Charge States Following a Single Gas-Phase Purification and Concentration Procedure", Anal. Chem. 2002, pp. 4653-4661.

Horn, et al, "Automated Reduction and Interpretation of High Resolution Electrospray Mass Spectra of Large Molecules," J. Am. Soc. Mass Spectrom., vol. 11, No. 4., (2000), pp. 320-332.

Kalli et al., "Evaluation and Optimization of Mass Spectrometric Settings During Data-dependent Acquisition Mode: Focus on LTQ-Orbitrap Mass Analyzers," J. Proteome Res., 2013, 12, pp. 3071-3086.

Kyowon et al., "UniNovo : A Universal Tool for de Novo Peptide Sequencing", Research in Computational Molecular Biology, Springer Berlin Heidelberg, XP047026500, 2013, pp. 100-117.

Liu et al., "Top-Down Protein Identification/Characterization of a Priori Unknown Proteins via Ion Trap Collision-Induced Dissociation and Ion/Ion Reactions in a Quadrupole/Time-of-Flight Tandem Mass Spectrometer", Anal. Chem. 2009, 81, pp. 1433-1441.

McLuckey et al., "Electrospray/Ion Trap Mass Spectrometry for the Detection and Identification of Organisms", joint services workshop on biological mass spectrometry, Baltimore, MD (United States), Jul. 28-30, 1997, https://www.osti.gov/scitech/biblio/622805, pp. 1-8.

McLuckey et al., "Ion Parking during Ion/Ion Reactions in Electrodynamic Ion Traps", Anal. Chem. 2002, 74, pp. 336-346.

McLuckey et al., "Ion/Ion Chemistry of High-Mass Multiply Charged Ions", Mass Spectrometry Reviews, 1998, 17, pp. 369-407.

McLuckey et al., "Ion/Ion Proton-Transfer Kinetics: Implications forAnalysis of Ions Derived from Electrospray of Protein Mixtures", Anal. Chem. 1998, 70, pp. 1198-1202.

McLuckey et al., "Ion/Molecule Reactions for Improved Effective Mass Resolution in Electrospray Mass Spectrometry", Anal. Chem. 1995, 67, pp. 2493-2497.

Reid et al., "Gas-Phase Concentration, Purification, and Identification ofWhole Proteins from Complex Mixtures", J. Am. Chem. Soc. 2002, 124, pp. 7353-7362.

Scalf et al., "Charge Reduction Electrospray Mass Spectrometry", Anal. Chem. 2000, 72, pp. 52-60.

Stephenson et al., "Charge Manipulation for Improved Mass Determination of High-mass Species and Mixture Components by Electrospray Mass Spectrometry", J. Mass Spectrom. 1998, 33, pp. 664-672.

Stephenson et al., "Ion-ion Proton Transfer Reactions of Bio-ions Involving Noncovalent Interactions: Holomyoglobin", J Am Soc Mass Spectrom 1997, 8, pp. 637-644.

Stephenson et al., "Ion/Ion Proton Transfer Reactions for ProteinMixture Analysis", Anal. Chem. 1996, 68, pp. 4026-4032.

Stephenson et al., "Ion/Ion Reactions for Oligopeptide Mixture Analysis: Application to Mixtures Comprised of 0.5-100 kDa Components", J Am Soc Mass Spectrom 1998, 9, pp. 585-596.

Stephenson et al., "Ion/Ion Reactions in the Gas Phase: Proton Transfer Reactions Involving Multiply-Charged Proteins", J. Am. Chem. Soc. 1996, 118, pp. 7390-7397.

Stephenson et al., "Simplification of Product Ion Spectra Derived from Multiply Charged Parent Ions via Ion/Ion Chemistry", Anal. Chem. 1998, 70, pp. 3533-3544.

Subramanian et al., "S1182 Serum Protein Signatures Determined by Mass Spectrometry (SELDI-ToF) Accurately Distinguishes Crohn's Disease (CD) from Ulcerative Colitis (UC)", Gastroenterology, Elsevier, Amsterdam, NL, vol. 134 (4), 2008, AGA Abstracts, p. A-196.

Sutton et al., "Top-Down Analysis of the Low Molecular Weight Human Plasma Proteome Using Hybrid Ion Trap-Fourier Transform Mass Spectrometry", http://tools.thermofisher.com/content/sfs/brochures/AN-344-LC-MS-Human-Plasma-Proteome-AN62498-EN.pdf, 2007, pp. 1-6.

Xia et al., "Mutual Storage Mode Ion/Ion Reactions in a Hybrid Linear Ion Trap", J Am Soc Mass Spectrom 2005, 16, pp. 71-81.

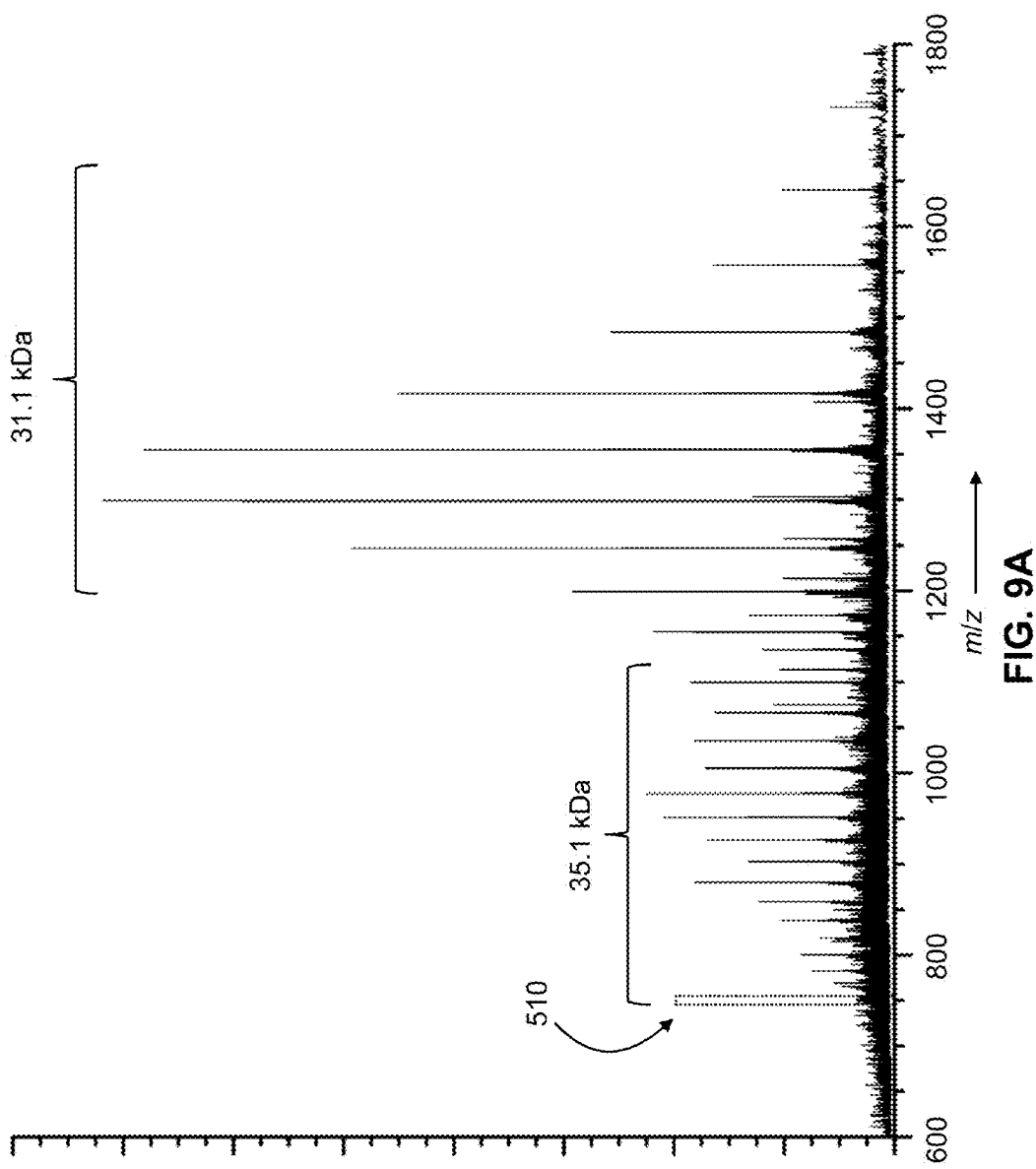

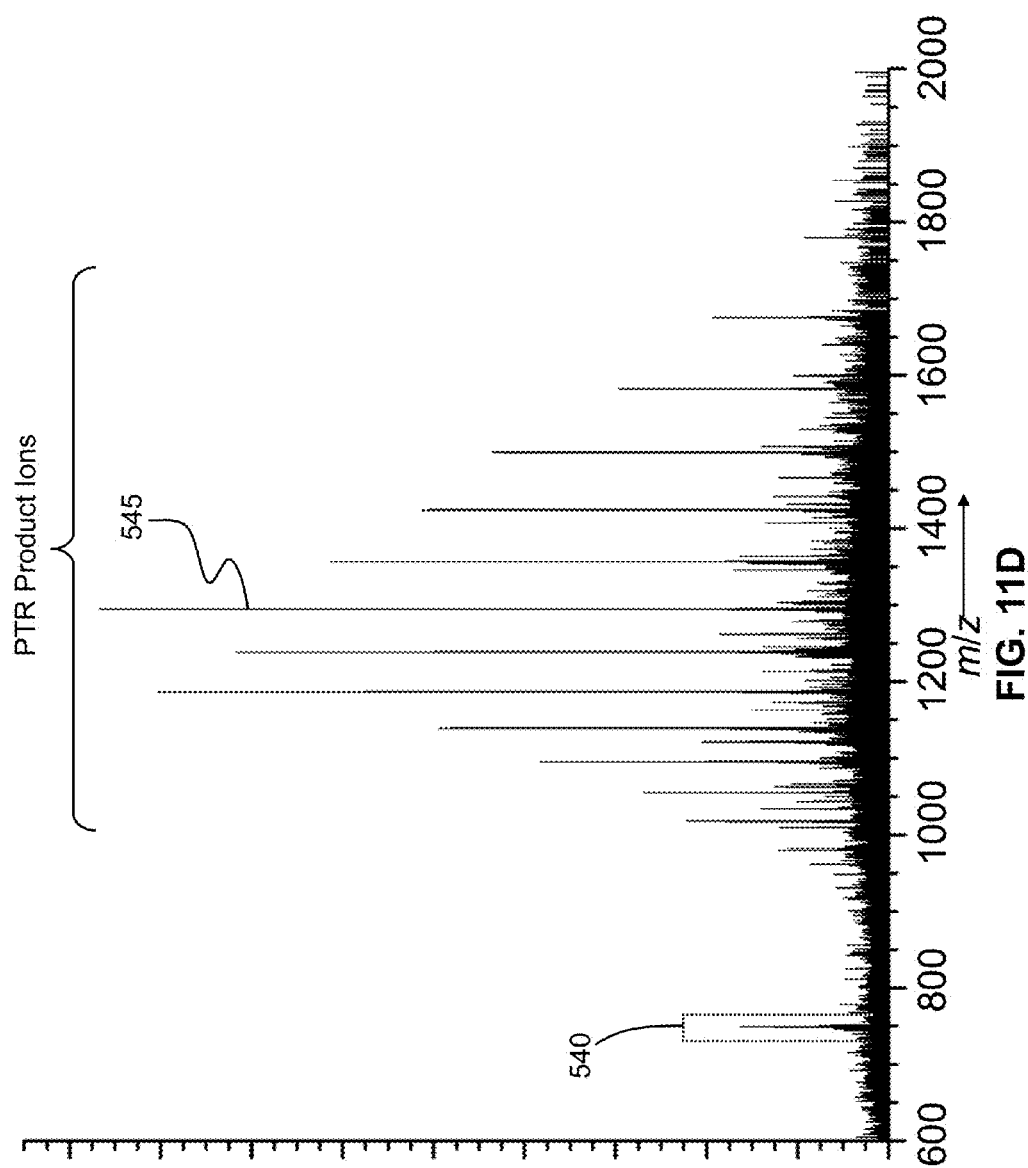

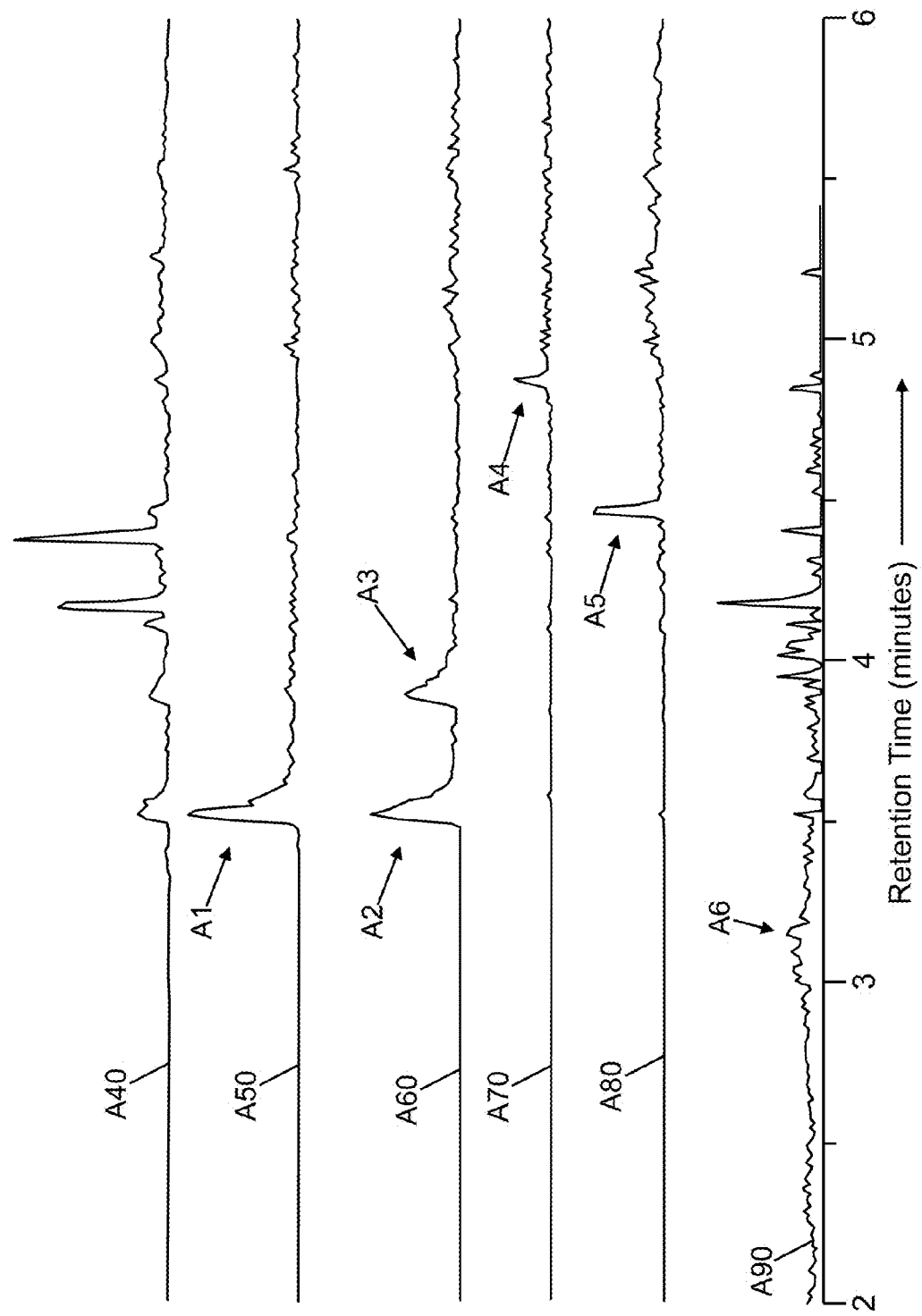

A400

Convert Centroid Data to Discretized Array Form

Table A1

| No. C$^{12}$ | MW(typical) | Mode(C$^{13}$) | Ave(C$^{13}$) | Ave − Mode |
|---|---|---|---|---|
| 50 | 1100 | 0 | 0.535 | 0.535 |
| 100 | 2200 | 1 | 1.07 | 0.07 |
| 150 | 3300 | 1 | 1.605 | 0.605 |
| 200 | 4400 | 2 | 2.14 | 0.14 |
| 250 | 5500 | 2 | 2.675 | 0.675 |
| 300 | 6600 | 3 | 3.21 | 0.21 |
| 350 | 7700 | 3 | 3.745 | 0.745 |
| 400 | 8800 | 4 | 4.28 | 0.28 |
| 450 | 9900 | 4 | 4.815 | 0.815 |
| 500 | 11000 | 5 | 5.35 | 0.35 |
| 550 | 12100 | 5 | 5.885 | 0.885 |
| 600 | 13200 | 6 | 6.42 | 0.42 |
| 650 | 14300 | 6 | 6.955 | 0.955 |
| 700 | 15400 | 7 | 7.49 | 0.49 |
| 750 | 16500 | 8 | 8.025 | 0.025 |
| 800 | 17600 | 8 | 8.56 | 0.56 |
| 850 | 18700 | 9 | 9.095 | 0.095 |
| 900 | 19800 | 9 | 9.63 | 0.63 |
| 950 | 20900 | 10 | 10.165 | 0.165 |
| 1000 | 22000 | 10 | 10.7 | 0.7 |
| 1050 | 23100 | 11 | 11.235 | 0.235 |
| 1100 | 24200 | 11 | 11.77 | 0.77 |
| 1150 | 25300 | 12 | 12.305 | 0.305 |
| 1200 | 26400 | 12 | 12.84 | 0.84 |
| 1250 | 27500 | 13 | 13.375 | 0.375 |

FIG. 20A

Table A1 (continued)

| No. $C^{12}$ | MW(typical) | Mode($C^{13}$) | Ave($C^{13}$) | Ave − Mode |
|---|---|---|---|---|
| 1300 | 28600 | 13 | 13.91 | 0.91 |
| 1350 | 29700 | 14 | 14.445 | 0.445 |
| 1400 | 30800 | 14 | 14.98 | 0.98 |
| 1450 | 31900 | 15 | 15.515 | 0.515 |
| 1500 | 33000 | 16 | 16.05 | 0.05 |
| 1550 | 34100 | 16 | 16.585 | 0.585 |
| 1600 | 35200 | 17 | 17.12 | 0.12 |
| 1650 | 36300 | 17 | 17.655 | 0.655 |
| 1700 | 37400 | 18 | 18.19 | 0.19 |
| 1750 | 38500 | 18 | 18.725 | 0.725 |
| 1800 | 39600 | 19 | 19.26 | 0.26 |
| 1850 | 40700 | 19 | 19.795 | 0.795 |
| 1900 | 41800 | 20 | 20.33 | 0.33 |
| 1950 | 42900 | 20 | 20.865 | 0.865 |
| 2000 | 44000 | 21 | 21.4 | 0.4 |
| 2050 | 45100 | 21 | 21.935 | 0.935 |
| 2100 | 46200 | 22 | 22.47 | 0.47 |
| 2150 | 47300 | 23 | 23.005 | 0.005 |
| 2200 | 48400 | 23 | 23.54 | 0.54 |
| 2250 | 49500 | 24 | 24.075 | 0.075 |
| 2300 | 50600 | 24 | 24.61 | 0.61 |
| 2350 | 51700 | 25 | 25.145 | 0.145 |
| 2400 | 52800 | 25 | 25.68 | 0.68 |
| 2450 | 53900 | 26 | 26.215 | 0.215 |
| 2500 | 55000 | 26 | 26.75 | 0.75 |

FIG. 20B

Table A1 (continued)

| No. $C^{12}$ | MW(typical) | Mode($C^{13}$) | Ave($C^{13}$) | Ave − Mode |
|---|---|---|---|---|
| 2550 | 56100 | 27 | 27.285 | 0.285 |
| 2600 | 57200 | 27 | 27.82 | 0.82 |
| 2650 | 58300 | 28 | 28.355 | 0.355 |
| 2700 | 59400 | 28 | 28.89 | 0.89 |
| 2750 | 60500 | 29 | 29.425 | 0.425 |
| 2800 | 61600 | 29 | 29.96 | 0.96 |
| 2850 | 62700 | 30 | 30.495 | 0.495 |
| 2900 | 63800 | 31 | 31.03 | 0.03 |
| 2950 | 64900 | 31 | 31.565 | 0.565 |
| 3000 | 66000 | 32 | 32.1 | 0.1 |
| 3050 | 67100 | 32 | 32.635 | 0.635 |
| 3100 | 68200 | 33 | 33.17 | 0.17 |
| 3150 | 69300 | 33 | 33.705 | 0.705 |
| 3200 | 70400 | 34 | 34.24 | 0.24 |
| 3250 | 71500 | 34 | 34.775 | 0.775 |
| 3300 | 72600 | 35 | 35.31 | 0.31 |
| 3350 | 73700 | 35 | 35.845 | 0.845 |
| 3400 | 74800 | 36 | 36.38 | 0.38 |
| 3450 | 75900 | 36 | 36.915 | 0.915 |
| 3500 | 77000 | 37 | 37.45 | 0.45 |
| 3550 | 78100 | 37 | 37.985 | 0.985 |
| 3600 | 79200 | 38 | 38.52 | 0.52 |
| 3650 | 80300 | 39 | 39.055 | 0.055 |
| 3700 | 81400 | 39 | 39.59 | 0.59 |
| 3750 | 82500 | 40 | 40.125 | 0.125 |

FIG. 20C

Table A1 (continued)

| No. C$^{12}$ | MW(typical) | Mode(C$^{13}$) | Ave(C$^{13}$) | Ave − Mode |
|---|---|---|---|---|
| 3800 | 83600 | 40 | 40.66 | 0.66 |
| 3850 | 84700 | 41 | 41.195 | 0.195 |
| 3900 | 85800 | 41 | 41.73 | 0.73 |
| 3950 | 86900 | 42 | 42.265 | 0.265 |
| 4000 | 88000 | 42 | 42.8 | 0.8 |
| 4050 | 89100 | 43 | 43.335 | 0.335 |
| 4100 | 90200 | 43 | 43.87 | 0.87 |
| 4150 | 91300 | 44 | 44.405 | 0.405 |
| 4200 | 92400 | 44 | 44.94 | 0.94 |
| 4250 | 93500 | 45 | 45.475 | 0.475 |
| 4300 | 94600 | 46 | 46.01 | 0.01 |
| 4350 | 95700 | 46 | 46.545 | 0.545 |
| 4400 | 96800 | 47 | 47.08 | 0.08 |
| 4450 | 97900 | 47 | 47.615 | 0.615 |
| 4500 | 99000 | 48 | 48.15 | 0.15 |
| 4550 | 100100 | 48 | 48.685 | 0.685 |
| 4600 | 101200 | 49 | 49.22 | 0.22 |
| 4650 | 102300 | 49 | 49.755 | 0.755 |
| 4700 | 103400 | 50 | 50.29 | 0.29 |
| 4750 | 104500 | 50 | 50.825 | 0.825 |
| 4800 | 105600 | 51 | 51.36 | 0.36 |
| 4850 | 106700 | 51 | 51.895 | 0.895 |
| 4900 | 107800 | 52 | 52.43 | 0.43 |
| 4950 | 108900 | 52 | 52.965 | 0.965 |
| 5000 | 110000 | 53 | 53.5 | 0.5 |

FIG. 20D

Assignment Controls

|  | MS1 | MS2 |
|---|---|---|
| Mass Accuracy in ppm: | 10 | 10 |
| Peaks Intensity Threshold: | 50000 | 25000 |
| Peaks S/N Threshold: | 10 | 5 |
| Lowest Charge State: | 1 | 1 |
| Highest Charge State: | 50 | 50 |

FIG. 21B

Clustering Controls

|  | MS1 | MS2 |
|---|---|---|
| Minimum Contiguous Charge States | 3 | 3 |
| Minimum Contiguous Isotopes | 5 | 3 |
| Sufficient Contiguous Charge States | 5 | 5 |
| Sufficient Contiguous Isotopes | 7 | 4 |
| Mass Separation | 15 | 15 |

FIG. 21C

METHODS FOR TOP-DOWN MULTIPLEXED MASS SPECTRAL ANALYSIS OF MIXTURES OF PROTEINS OR POLYPEPTIDES

CROSS REFERENCE TO RELATED APPLICATIONS

This application claims, under 35 U.S.C. § 119(e), priority to and the benefit of the filing date of commonly-assigned U.S. Provisional Application No. 62/278,935, filed on Jan. 14, 2016 and titled "Methods for Top-Down Multiplexed Mass Spectral Analysis of Mixtures of Proteins or Polypeptides", the disclosure of which is hereby incorporated by reference in its entirety. The subject matter of this application is also related to commonly-assigned and co-pending International Application No. PCT/US2015/040914, filed on Jul. 17, 2015 and titled "Methods for Mass Spectrometry of Mixtures of Proteins of Polypeptides Using Proton Transfer Reaction" and to commonly-assigned and co-pending U.S. application Ser. No. 15/067,727, filed on Mar. 11, 2016 and titled "Methods for Data-Dependent Mass Spectrometry of Mixed Biomolecular Analytes", the disclosures of both of said applications hereby incorporated by reference herein in their entirety.

TECHNICAL FIELD

The present invention relates to mass spectrometry and, more particularly, relates to methods for mass spectrometric analysis of complex mixtures of proteins or polypeptides by methods that include subjecting ionized samples to proton transfer reactions to separate ionized proteins and polypeptides from other molecules and performing mathematical deconvolution analysis of resulting reaction products to simultaneously characterize a plurality of proteins and/or polypeptides in the mixture.

BACKGROUND ART

The study of proteins in living cells and in tissues (proteomics) is an active area of clinical and basic scientific research because metabolic control in cells and tissues is exercised at the protein level. For example, comparison of the levels of protein expression between healthy and diseased tissues, or between pathogenic and nonpathogenic microbial strains, can speed the discovery and development of new drug compounds or agricultural products. Further, analysis of the protein expression pattern in diseased tissues or in tissues excised from organisms undergoing treatment can also serve as diagnostics of disease states or the efficacy of treatment strategies, as well as provide prognostic information regarding suitable treatment modalities and therapeutic options for individual patients. Still further, identification of sets of proteins in samples derived from microorganisms (e.g., bacteria) can provide a means to identify the species and/or strain of microorganism as well as, with regard to bacteria, identify possible drug resistance properties of such species or strains.

One important aspect of proteomics is the identification of proteins with altered expression levels. Differences in protein and metabolite levels over time or among populations can be associated with diseased states, drug treatments, or changes in metabolism. Identified molecular species may serve as biological markers for the disease or condition in question, allowing for new methods of diagnosis and treatment to be developed. Conventionally, because of the large number of proteins that are generally present in any sample extracted from natural tissue or cells, the proteins must first be separated into individual components by gel or capillary electrophoresis or affinity techniques, before the individual proteins levels can be assessed and compared to a database or between samples.

Because it can provide detailed structural information, mass spectrometry (MS) is currently considered to be a valuable analytical tool for biochemical mixture analysis and protein identification. Conventional methods of protein analysis therefore often combine two-dimensional (2D) gel electrophoresis, for separation and quantification, with mass spectrometric identification of proteins. Also, capillary liquid chromatography as well as various other "front-end" separation techniques have been combined with electrospray ionization tandem mass spectrometry for large-scale protein identification without gel electrophoresis. Using mass spectrometry, qualitative differences between mass spectra can be identified, and proteins corresponding to peaks occurring in only some of the spectra serve as candidate biological markers.

In recent years, mass spectrometry has also gained popularity as a tool for identifying microorganisms due to its increased accuracy and shortened time-to-result when compared to traditional methods for identifying microorganisms. To date, the most common mass spectrometry method used for microbial identification is matrix-assisted laser desorption ionization time-of-flight (MALDI-TOF) mass spectrometry. In MALDI-TOF, cells of an unknown microorganism are mixed with a suitable ultraviolet light absorbing matrix solution and are allowed to dry on a sample plate. Alternatively, an extract of microbial cells is used instead of the intact cells. After transfer to the ion source of a mass spectrometer, a laser beam is directed to the sample for desorption and ionization of the proteins and time-dependent mass spectral data is collected.

The mass spectrum of a microorganism produced by MALDI-TOF methods reveals a number of peaks from intact peptides, proteins, protein fragments, and other molecules that constitute the microorganism's "fingerprint". This method relies on the pattern matching of the peak profiles in the mass spectrum of an unknown microorganism to a reference database comprising a collection of mass spectra for known microorganisms obtained using essentially the same experimental conditions. The better the match between the spectrum of the isolated microorganism and a spectrum in the reference database, the higher the confidence level in identification of the organism at the genus, species, or in some cases, subspecies level. Because the method relies upon matching the patterns of peaks in MALDI-TOF mass spectra, there is no requirement to identify or otherwise characterize the proteins represented in the spectrum of the unknown microorganism in order to identify it.

Although MALDI-TOF methods are rapid and cost effective, they have limitations that restrict the range of applications to pathogen characterization and identification including but not limited to virulence detection and quantitation, resistance marker determination, strain matching, and antibiotic susceptibility testing to name a few. The information content within a MALDI mass spectrum reflects the most abundant and ionizable proteins which are generally limited to ribosomal proteins at the experimental conditions used. Because ribosomal proteins are highly conserved among prokaryotes, differentiation of closely related microorganisms by MALDI-TOF is limited. In this case many of the ribosomal proteins across closely related species contain either the same or slightly different amino acid sequences (i.e. single amino acid substitutions) that cannot be effectively differentiated with low resolution mass spectrometers. Moreover, determination of strain and/or serovar type, antibiotic resistance, antibiotic susceptibility, virulence or other important characteristics relies upon the detection of protein markers other than ribosomal proteins which further limits the application of MALDI-TOF for microbial analysis. Laboratories using MALDI-TOF for identification of microorganisms must use other methods to further characterize the identified microbes. In addition, the MALDI-TOF method's reliance upon matching spectral patterns requires a pure culture for high quality results and thus is not generally suitable for direct testing, mixed cultures, blood culture, or other complex samples containing different microorganisms.

Several other mass spectrometry methods for detection of microorganisms have been used. For example, mass spectrometry-based protein sequencing methods have been described wherein liquid chromatography is coupled to tandem mass spectrometry (LC-MS/MS) and sequence information is obtained from enzymatic digests of proteins derived from the microbial sample. This approach, termed "bottom-up" proteomics, is a widely practiced method for protein identification. The method can provide identification to the subspecies or strain level as chromatographic separation allows the detection of additional proteins other than just ribosomal proteins, including those useful for characterization of antibiotic resistance markers and virulence factors.

In contrast to "bottom-up" proteomics, "top-down" proteomics refers to methods of analysis in which protein samples are introduced intact into a mass spectrometer, without enzymatic, chemical or other means of digestion. Top-down analysis enables the study of the intact protein, allowing identification, primary structure determination and localization of post-translational modifications (PTMs) directly at the protein level. Top-down proteomic analysis typically consists of introducing an intact protein into the ionization source of a mass spectrometer, fragmenting the protein ions and measuring the mass-to-charge ratios and abundances of the various fragments so-generated. The resulting fragmentation is many times more complex than a peptide fragmentation, which may, in the absence of the methods taught herein, necessitate the use of a mass spectrometer with very high mass accuracy and resolution capability in order to interpret the fragmentation pattern with acceptable certainty. The interpretation generally includes comparing the observed fragmentation pattern to either a protein sequence database that includes compiled experimental fragmentation results generated from known samples or, alternatively, to theoretically predicted fragmentation patterns. For example, Liu et al. ("Top-Down Protein Identification/Characterization of a Priori Unknown Proteins via Ion Trap Collision-Induced Dissociation and Ion/Ion Reactions in a Quadrupole/Time-of-Flight Tandem Mass Spectrometer", *Anal. Chem.* 2009, 81, 1433-1441) have described top-down protein identification and characterization of both modified and unmodified unknown proteins with masses up to ≈28 kDa.

An advantage of a top-down analysis over a bottom-up analysis is that a protein may be identified directly, rather than inferred as is the case with peptides in a bottom-up analysis. Another advantage is that alternative forms of a protein, e.g. post-translational modifications and splice variants, may be identified. However, top-down analysis has a disadvantage when compared to a bottom-up analysis in that many proteins can be difficult to isolate and purify. Thus, each protein in an incompletely separated mixture can yield, upon mass spectrometric analysis, multiple ion species, each species corresponding to a different respective degree of protonation and a different respective charge state, and each such ion species can give rise to multiple isotopic variants. A single MS spectrum measured in a top-down analysis can easily contain hundreds to even thousands of peaks which belong to different analytes—all interwoven over a given m/z range in which the ion signals of very different intensities overlap and suppress one other.

Because mass spectra of biological samples, as obtained in top-down analyses, are generally very complex, improved methods are required for interpreting the mass spectra. The resulting computational challenge that such methods must overcome is to trace each peak back to a certain analyte(s) and, once this is done for one or several analytes, to determine the molecular weights of analyte(s) in a process which is best described as mathematical decomposition (also referred to, in the art, as mathematical deconvolution). A still further challenge associated with the use of mass spectral analyses of proteins and polypeptides in a clinical setting is to derive such information in the shortest time period possible, often termed as analysis in "real time". Obviously, the computations are much more challenging in real time during an automatic top-down data dependent analysis since this should occur very fast, especially when chromatographic separation is involved. To succeed, one needs to provide both: (i) an optimized real time computational strategy as well as (ii) a mass spectral data acquisition strategy that anticipates multiple mass spectral lines for each ion species and that anticipates efficient isolation of analyte compounds of interest from a potential multitude of contaminant compounds.

The existing data dependent and dynamic exclusion workflow techniques and corresponding algorithms were developed for small molecules, small peptides and other analytes which acquire a limited number of charges (for example, 1-3 charges) in the electrospray ionization process. When applied to higher-molecular-weight biopolymer analytes (most commonly, intact proteins during the course of top-down proteomics studies) these conventional methodologies significantly under-perform due to a combination of different electrospray behavior and computational limitations. More specifically: (1) intact high mass analytes in general, and proteins in particular, develop many more charge states (up to 50 charges or more per molecule, e.g., FIG. 12C) than do small molecules during the electrospray ionization process because of a greater number of charge acquiring sites which results in much more complex MS spectra; (2) in complex mixtures such as cell lysates or their fractions, there is a wide distribution of molecular weights and copy numbers which results in a very complex overlap of charge state distribution patterns of varying intensities; (3) the variability in physiochemical properties of the high-mass analytes of the same or different chemical nature produces significant variability of chromatographic peak shapes and analyte retention on the column; (4) if the mass spectra are acquired on a mass spectrometer with high resolving power such as an Orbitrap™ mass analyzer (a type of electrostatic trap mass analyzer) or a time-of-flight (TOF) mass analyzer, corresponding peaks further resolve into a number of isotopes in a series of clusters whose quality is often far from a theoretical binomial distribution; (5) matrix ionization effects of a variety of different proteins can greatly influence the observed intensity of multiply overlapping species so as to distort the true ratios of protein intensities found in any given standard or sample. Additional levels of complexity are introduced by oxidized species of the same analyte or adducts, overlaps of isotope clusters and inability of existing software tools correctly calculate charge state for high mass species.

In practical terms, the above considerations imply that, in the case of intact proteins and other biopolymers, existing data dependent algorithms are being confounded and MS/MS is being performed in a redundant fashion on a number of different charge states from the same biopolymer. Also, when isotopic clusters do not match the traditional binomial distribution patterns defined by the number of carbon, hydrogen, nitrogen, oxygen, and sulfur atoms present in a given biopolymer, or do not meet intensity threshold or signal-to-noise requirements, redundancy occurs from fragmenting multiple isotopes which belong to the same isotopic cluster. This duplication of work leads to redundancy in identification of the most abundant/ionizable proteins, while the information about other species is lost and provides very little opportunity for triggering an $MS^n$ analysis.

With regard to efficient instrument-associated data acquisition strategies, it may be noted that ion-ion reactions have found great utility in the field of biological mass spectrometry over the last decade, primarily with the use of electron transfer dissociation (ETD) to dissociate peptide/proteins and determine primary sequence information and characterize post-translational modifications. Proton transfer, another type of ion-ion reaction, has also been used extensively in biological applications. Experimentally, in one form of proton transfer, multiply-positively-charged protein ions (i.e., protein cations) from a sample are allowed to react with singly-charged reagent anions so as to reduce the charge state of an individual protein cation and the number of such charge states of the protein cations. These reactions proceed with pseudo-first order reaction kinetics when the reagent anions are present in large excess over the protein cation population. The rate of reaction is directly proportional to the square of charge of the protein cation (or other multiply-charged cation) multiplied by the charge on the reagent anion. The same relationship also holds for reactions of the opposite polarity, defined here as reaction between singly-charged reagent cations and a population of multiply-charged anions derived from a protein sample. This produces a series of pseudo-first order consecutive reaction curves as defined by the starting multiply-charged protein cation population. Although the reactions are highly exothermic (in excess of 100 kcal/mol), proton transfer is an even-electron process performed in the presence of 1 mtorr of background gas (i.e. helium) and thus does not fragment the starting multiply-charged protein cation population. The collision gas serves to remove the excess energy on the microsecond time scale (108 collisions per second), thus preventing fragmentation of the resulting product ion population.

Proton transfer reactions (PTR) have been used successfully to identify proteins in mixtures of proteins. Particularly, application of proton transfer reaction methods may be envisioned as a mixture simplification process that is carried out in real-time (a few milliseconds) in a mass spectrometer that separates mass spectral signatures of proteins and polypeptides from one another as well as from generally low-charge contaminant ions. This procedure enables isolation of the analyte proteins and polypeptide ions either as a group or as individual ion species and has thus been employed to determine charge state and molecular weights of high mass proteins. PTR has also been utilized for simplifying product ion spectra derived from the collisional-activation of multiply-charged precursor protein ions. Although PTR reduces the overall signal derived from multiply-charged protein ions, this is more than offset by the significant gain in signal-to-noise ratio of the resulting PTR product ions. The PTR process is 100% efficient leading to only single series of reaction products, and no side reaction products that require special interpretation and data analysis.

Various aspects of the application of PTR to the analysis of peptides, polypeptides and proteins have been described in the following documents: U.S. Pat. No. 7,749,769 B2 in the names of inventors Hunt et al., U.S. Patent Pre-Grant Publication No. 2012/0156707 A1 in the names of inventors Hartmer et al., U.S. Pre-Grant Publication No. 2012/0205531 A1 in the name of inventor Zabrouskov; McLuckey et al., "Ion/Ion Proton-Transfer Kinetics: Implications for Analysis of Ions Derived from Electrospray of Protein Mixtures", *Anal. Chem.* 1998, 70, 1198-1202; Stephenson et al., "Ion-ion Proton Transfer Reactions of Bio-ions Involving Noncovalent Interactions: Holomyoglobin", *J. Am. Soc. Mass Spectrom.* 1998, 8, 637-644; Stephenson et al., "Ion/Ion Reactions in the Gas Phase: Proton Transfer Reactions Involving Multiply-Charged Proteins", *J. Am. Chem. Soc.* 1996, 118, 7390-7397; McLuckey et al., "Ion/Molecule Reactions for Improved Effective Mass Resolution in Electrospray Mass Spectrometry", *Anal. Chem.* 1995, 67, 2493-2497; Stephenson et al., "Ion/Ion Proton Transfer Reactions for Protein Mixture Analysis", *Anal. Chem.* 1996, 68, 4026-4032; Stephenson et al., "Ion/Ion Reactions for Oligopeptide Mixture Analysis: Application to Mixtures Comprised of 0.5-100 kDa Components", *J. Am. Soc. Mass Spectrom.* 1998, 9, 585-596; Stephenson et al., "Charge Manipulation for Improved Mass Determination of High-mass Species and Mixture Components by Electrospray Mass Spectrometry", *J. Mass Spectrom.* 1998, 33, 664-672; Stephenson et al., "Simplification of Product Ion Spectra Derived from Multiply Charged Parent Ions via Ion/Ion Chemistry", *Anal. Chem.*, 1998, 70, 3533-3544 and Scalf et al., "Charge Reduction Electrospray Mass Spectrometry", *Anal. Chem.* 2000, 72, 52-60. Various aspects of general ion/ion chemistry have been described in McLuckey et al., "Ion/Ion Chemistry of High-Mass Multiply Charged Ions", *Mass Spectrom. Rev.* 1998, 17, 369-407 and U.S. Pat. No. 7,550,718 B2 in the names of inventors McLuckey et al. Apparatus for performing PTR and for reducing ion charge states in mass spectrometers have been described in U.S. Pre-Grant Publication No. 2011/0114835 A1 in the names of inventors Chen et al., U.S. Pre-Grant Publication No. 2011/0189788 A1 in the names of inventors Brown et al., U.S. Pat. No. 8,283,626 B2 in the names of inventors Brown et al. and U.S. Pat. No. 7,518,108 B2 in the names of inventors Frey et al. Adaptation of PTR charge reduction techniques to detection and identification of organisms has been described by McLuckey et al. ("*Electrospray/Ion Trap Mass Spectrometry for the Detection and Identification of Organisms*", Proc. First Joint Services Workshop on Biological Mass Spectrometry, Baltimore, Md., 28-30 Jul. 1997, 127-132).

The product ions produced by the PTR process can be accumulated into one or into several charge states by the use of a technique known as "ion parking". Ion parking uses supplementary AC voltages to consolidate the PTR product ions formed from the original variously protonated ions of any given protein molecule into a particular charge state or states at particular mass-to-charge (m/z) values during the reaction period. This technique can be used to concentrate the product ion signal into a single or limited number of charge states (and, consequently, into a single or a few respective m/z values) for higher sensitivity detection or further manipulation using collisional-activation, ETD, or other ion manipulation techniques. Various aspects of ion parking have been described in U.S. Pat. No. 7,064,317 B2 in the name of inventor McLuckey; U.S. Pat. No. 7,355,169 B2 in the name of inventor McLuckey; U.S. Pat. No. 8,334,503 B2 in the name of inventor McLuckey; U.S. Pat. No. 8,440,962 B2 in the name of inventor Le Blanc; and in the following documents: McLuckey et al., "Ion Parking during Ion/Ion Reactions in Electrodynamic Ion Traps", Anal. Chem. 2002, 74, 336-346; Reid et al., "Gas-Phase Concentration, Purification, and Identification of Whole Proteins from Complex Mixtures", J. Am. Chem. Soc. 2002, 124, 7353-7362; He et al., "Dissociation of Multiple Protein Ion Charge States Following a Single Gas-Phase Purification and Concentration Procedure", Anal. Chem. 2002, 74, 4653-4661; Xia et al., "Mutual Storage Mode Ion/Ion Reactions in a Hybrid Linear Ion Trap", J. Am. Soc. Mass. Spectrom. 2005, 16, 71-81; Chrisman et al., "Parallel Ion Parking: Improving Conversion of Parents to First-Generation Products in Electron Transfer Dissociation", Anal. Chem. 2005, 77(10), 3411-3414 and Chrisman et al., "Parallel Ion Parking of Protein Mixtures", Anal. Chem. 2006, 78, 310-316.

As a result of the ongoing requirement in the art of mass spectral proteome analysis for analysis of complex natural samples in real-time or near-real-time, there is thus a need for improved methods of mass analysis, both instrumental and computational, that can efficiently separate analytes from contaminants, differentiate signal from noise, correctly allocate related m/z values into proper isotopic clusters, correctly determine charge states and properly organize the various charge states into distribution envelopes. Such improvements are required for success in both data acquisition and, optionally, post-acquisition processing workflows. Preferably, the improved instrumental methods, workflows and algorithms should be able to work in a "real-time" environment such that automated data-dependent decisions may be made while mass spectra are being acquired and such that clinical interpretations may be made shortly thereafter. The present disclosure addresses these needs.

DISCLOSURE OF INVENTION

The present disclosure teaches an application of ion-ion reaction chemistry in which: (i) one or more stages of proton transfer reactions, optionally supplemented by data-dependent fragmentation, are employed to simplify the mass spectrometric analysis of complex ion populations derived from electrospray ionization of samples comprising mixtures of compounds extracted from samples of tissues, biological fluids, microorganisms or other cells; and (ii) an optimized spectral deconvolution procedure is employed to automatically discriminate between mass spectral signatures, in the simplified spectra, of a plurality of biopolymer molecules in a sufficiently short time (i.e., computation time of one second or less) such that decisions may be made in real time regarding the course of subsequent mass spectral analysis steps of the same respective sample.

In particular, the inventors have discovered that by subjecting a mass-to-charge-restricted subset of such ions to PTR, the resulting population of product ions comprises a much simpler population of charge states of lower total charge values (where the words "lower" or "reduced", in this context, refer to lower or reduced in terms of absolute value) which can be readily resolved and assigned to specific protein or peptide ions. Because the PTR product ions represent a smaller subset of multiply-charged species derived from a complex mixture of charge states than the original precursor ions, mass spectral interpretation is greatly simplified and target analysis using tandem mass spectrometry (MS/MS or MS$^n$) can be performed on a single protein or other component(s) derived from a microbial extract.

The charge-reduced protein and peptide product ions resulting from a given proton transfer reaction produce mass-to-charge (m/z) values that are greater than those of the original m/z values. For a mixture of protein ions that have the same m/z value but differing mass and charge, the mixture can be separated on the micro- or millisecond timescale. Further, these multiply-charged protein ions of the same m/z value with differing mass and charge can be separated from low m/z value background ions derived from small molecules, lipids, solvents, or other interferents based on the charge squared dependence of the reaction. Multiply-charged ions are therefore separated in time from the background signal thus producing a separated protein mixture at highly increased signal-to-noise (s/n) ratio. The inventors have discovered that, as a result of these two factors, the spectral signatures of the protein/peptide or any other analyte product ions may be significantly separated from those of most interferent ions. In addition, multiple stages of PTR reactions can be performed to separate protein mixtures on low resolution instrumentation, such as a linear ion trap mass spectrometer, in order to simplify and isolate these proteins and other analytes such that target analysis can be performed via MS$^n$ analysis. The inventors have further discovered that the advantageous properties of simple PTR reactions may be even further amplified by performing "ion parking" procedures in conjunction with PTR reaction, thus enabling an analyst to at least partially select or control the product-ion charge state distribution that results from the PTR reaction.

PTR can also be used to improve high mass performance in mass spectrometry. In mass spectrometry, an ion may be assigned either an integer nominal mass or mass-to-charge ratio or an accurate or exact mass or mass-to-charge ratio. Accurate or exact masses or mass-to-charge ratios can be considered as comprising an integer component or value and a decimal component or value. Atomic and molecular masses are measured in units of daltons (Da) and m/z ratio values are generally given in in units of daltons per elementary charge, or Da/e or thomson (Th). It is to be noted that, in instances of described numerical values of m/z ratios in this document, such ratios are understood to be provided in units of daltons per elementary charge, or Th. Accurate or exact (i.e. non-integer) masses or m/z ratios can be represented as an integer nominal mass or mass-to-charge ratio value or component together with a corresponding decimal component. Thus, as used in this document, accurate mass determination or mass analysis can be considered as comprising sub-integer accuracy, i.e. accuracy of ±0.5 Da or better and, preferably, 0.1 Da or better.

Alternatively, accurate or exact masses or m/z ratios may be defined in terms of parts-per-million (ppm) mass accuracy. For mass spectrometric determinations of polypeptides and proteins, an experimental mass accuracy of 50 ppm or better, more preferably 10 ppm or better and, still more preferably 1 ppm or better, is generally required because such molecules and their ions frequently have molecular or ionic weights of at least 10,000 Da and as much as 100,000 Da. Thus, as used in this document, accurate mass determination or mass analysis can alternatively be considered as comprising an accuracy of 50 ppm or better, more preferably 10 ppm or better and, still more preferably, 1 ppm or better.

In addition to improving the signal-to-noise ratios for this type of analysis, the inventors have considered that the reduction of charge on protein ions causes these large ions to refold in the gas phase, as has been described in Zhao et al., "Effects of Ion/Ion Proton Transfer Reactions on Conformation of Gas-Phase Cytochrome c Ions", *J. Am. Soc. Mass Spec.* 2010, 21, 1208-1217. It is believed that this results in a more compact configuration which reduces the collisional cross section of the protein ions and, accordingly, increases their stability against fragmentation by collision with background gas molecules present in the mass analyzer chamber. The inventors have discovered that this effect can be especially beneficial with mass analyzers that employ image current detection, such as is done in a Fourier-transform ion cyclotron resonance (FT-ICR) mass analyzer or in an Orbitrap™ mass analyzer (a type of electrostatic trap mass analyzer commercially available from Thermo Fisher Scientific of Waltham, Mass. USA). Another potential reason for improved high mass performance is the large deposition of energy into a given protein ion that results from the PTR process. The energy deposited as a result of the PTR process exceeds 100 kcal/mol and is then effectively dampened by the presence of collision energy. This rapid heating process "boils off" neutral molecules that may be attached to the protein via ion-dipole, ion-induced dipole, or dipole-induced dipole interactions. Most importantly, the reduction of charge state for high mass proteins may significantly improve the transfer of these ions from the relatively high pressure of an ion guide, ion storage or ion trapping device where the PTR process is commonly performed, to a lower-pressure region of a mass analyzer, such as an Orbitrap™ mass analyzer. The reduced charge state means that ions are transferred at less kinetic energy thus limiting ion scattering, direct fragmentation, or formation of metastable species. The inventors further consider that this latter property is especially significant in enabling high-accuracy mass analysis of the PTR product ions in an accurate-mass spectrometer—such as the Orbitrap™-type of electrostatic trap mass analyzer—that detects image currents produced by cyclic ionic motion over an extended time range.

The present teachings are especially useful for the analysis and identification of intact proteins having molecular weight in excess of 50 kDa. The inventors have discovered the surprising result that, taken together, the various advantageous factors noted above can enable accurate identification of multiple intact proteins or large peptides from even very complex mixtures derived from natural microorganism samples. Such identifications can enable microorganism identification to the species, subspecies or even strain level. The target protein or polypeptide ion single species or multiple species may be chosen so as to be indicative, based on prior knowledge or information, either individually or in combination, of the presence in a sample of a specific microorganism or cell type, or a specific strain or variant of a microorganism or cell type, or a given virulence factor or toxin, or of the capacity of a microorganism or cell to resist an antimicrobial compound or antibiotic drug.

The present invention, in one aspect, offers an alternative to traditional bottom-up proteomics methods, namely top-down analysis of intact proteins derived from microbial cells via a method which is applicable to substantially all microorganisms including Gram-positive bacteria, Gram-negative bacteria, mycobacteria, *mycoplasma*, yeasts, protozoans, filamentous (i.e., microscopic) fungi. The present invention provides identification of microorganisms at the genus, species, subspecies, strain pathovar, and serovar level even in samples containing mixtures of microorganisms and/or microorganisms analyzed directly from pure and/or mixed cultures and from direct samples (e.g., surface swabs, bodily fluids, etc.). In addition, the approaches taught herein can be employed for targeted detection of virulence factors, antibiotic resistance and susceptibility markers, or other characteristics. The top-down methods of the present teachings are simple and quick because there is no need for chemical or enzymatic digestion of a sample and data processing is accomplished in real time.

Methods in accordance with the present teachings may comprise at least one or more of the following steps: microbial cell disruption, solubilization of proteins, sample clean-up (to desalt, remove insoluble components and debris, and/or concentrate), sample infusion or flow injection, fast partial liquid chromatographic separation, standard chromatographic separation, isoelectric focusing, ionization of proteins in solution, isolation of a given m/z range of the ions, causing the isolated range of ions to undergo PTR so as to form first-generation PTR product ions, optional isolation of an m/z range of the first-generation PTR product ions, optional mass spectrometry in MS or MS/MS mode, optionally causing the isolated range of first-generation PTR product ions to undergo a second PTR reaction so as to form second-generation PTR product ions, mass spectrometry in MS or MS/MS mode, and microbial identification via molecular weight analysis and/or protein sequence analysis, or using any statistical classification method. Preferably, but not necessarily, the mass spectrometry steps are performed with a high-resolution, high-accuracy mass spectrometer, such as a mass spectrometer comprising an Orbitrap™ mass analyzer.

Because a common method using a limited set of chemical reagents is performed, the methods of the present teachings are suitable for use within a completely automated system for sample preparation and mass spectrometry. Ideally, these methods may be automated from sample preparation through results reporting. Results may be automatically transferred to a hospital's electronic medical records system where they can be directly linked to patient treatment strategies, insurance, billing, or used in epidemiological reporting. Such an integrated system facilitates epidemiological tracking of an outbreak at the hospital, local, regional, and global levels. For high throughput laboratories, multiple systems can be interfaced to a central computer which integrates data from the different instruments prior to reporting. The system can import phenotypic susceptibility data where it can be combined with identification, virulence, antibiotic resistance and typing information generated by the invention.

Computational methods described herein enable both effective (1) non-redundant data dependent mass spectrometry analysis employing mass spectral workflow decision-making based on results of the computations and, optionally, post-acquisition data processing for individual high mass analytes and their mixtures of different complexities. For data dependent mass spectrometry analysis, the herein-described novel "Top P Unique Analyte-Specific Clusters" workflow and associated computation replaces the previous conventional state-of-the-art "Top P Most Abundant Precursors" logic. Each such species-correlative envelope is a set of related mass spectral lines (m/z values) which are indicated, according to the methods of the present teachings, to all be generated from a single unique molecule. Each species-correlative envelope groups together various charge states and isotopic clusters that are indicated to have been produced from a single molecular species. The method also works with mass spectral data in which no peaks attributable to isotopic distributions are observed (such as may be the case for low-resolution data) or with mass spectral data having resolved isotopic distributions but only one charge state per molecule. However, the species-correlative envelope can exclude adducts if desired, which are removed prior to data analysis.

Tandem mass spectrometry (or, more-generally, MS$^n$ analysis) may be performed, based on the computational results, only on selected representatives of a given species-correlative charge state distribution envelope after which data acquisition is directed to the next species-correlative charge state distribution envelope (i.e., of a different compound) that is determined in a preceding MS spectrum, and so on. In various embodiments, the computations are made using data derived from one or more stages of application of proton transfer reaction (PTR), as noted above, to subsets of ions derived from a biological sample comprising a complex mixture of proteins and/or polypeptides and other organic molecules. Prior to MS$^n$ analysis, computed charge state distribution patterns are filtered so as to exclude oxidized (or other specified) species of the same analyte and various other unwanted adducts. In this approach, the most possible abundant information on the analytes in a sample is retrieved either on a chromatographic time scale, or in experiments in which sample is introduced into a mass spectrometer by infusion, flow injection or by means of any other sample introduction device. In all cases, data-acquisition redundancy is either totally eliminated or significantly reduced.

The optimized "Top P Unique Analyte-Specific Clusters" computational workflow may include one or more of: (1) use of centroids for representing peak positions; (2) use of either a binary or simplified intensity scale for representing peak heights; (3) correct computational assignment of charge state to each peak (centroid) in isotopic clusters found in a scan; (4) the use of information on charge state to assign isotopic clusters (either resolved or unresolved) to the appropriate charge-state envelope(s); (5) optional determination of molecular weights; and (6) the control of data-dependent acquisition in a way to allow only one (or a selected number) of MS$^n$ event(s) per each individual charge state envelope. The "Top P Unique Cluster" method can be set up to recognize and work with either the most intense charge state for a given biopolymer, the median charge state between the highest charge state detected and the most intense charge state observed, or any other desired charge state (i.e., not just a maximum abundance or median charge state) or combination of charge states. The method is therefore well-suited for use with a variety of ion activation methods used for ion fragmentation including but not limited to collision-induced dissociation (CID) and electron-transfer dissociation (ETD), defined for a given molecular weight range, or in instances in which the least abundant proteins species are interrogated first. Similar methods may be employed for post-acquisition data processing, in which the same computation logic is applied to raw MS spectra for which acquisition is completed prior to execution of the novel methods. Either real-time or post-acquisition data processing may further include molecular weight determination and analyte identification.

These principles of the present teachings can be applied for analytes of various molecular weights and chemical nature on high resolution tandem mass spectrometry systems including but not limited to mass spectrometer instruments that are based on or include an Orbitrap™ mass analyzer. Such instruments include Orbitrap Fusion™, Orbitrap Velos-Pro™, Q-Exactive™, and Orbitrap Elite™ as well as quadrupole time-of-flight (QTOF) mass spectrometers and Fourier transform ion cyclotron resonance (FT-ICR) mass spectrometers. Further, the same computational principles can be applied to isotopically unresolved charge state envelopes which can be seen in mass spectra obtained on high resolution mass spectrometry systems for comparatively very high mass analytes, or to unit resolution mass spectra obtained on mass analyzers such as linear ion traps or any other Paul trap configuration. In instances, instead of making charge determinations based on a distance between individually resolved lines of isotopic clusters, these are instead calculated using distances between charge states within the same charge state envelope. Again, this clustering based strategy can be applied to unit resolution data as well as to data generated by linear ion traps and triple quadrupole instrumentation.

When used in conjunction with chromatographic separation, the proposed computational workflow methods maximize information from each individual mass spectrum obtained during the course of a chromatographic run. The novel methods may also be employed in conjunction with mass spectral experiments in which sample is introduced by infusion or flow injection. In most experimental situations, the novel methods significantly reduce total analysis time. When applied to data already acquired, the novel "Top P Unique Analyte-Specific Clusters" workflow methods can maximize the information yield from MS spectra and can calculate the molecular weights of the analytes in real time.

The novel principles, workflows and algorithms and methods described and taught in this disclosure are applicable in all cases when several analytes are mass spectrometrically (MS) detectable within the same mass spectrum. For example, the novel teachings may be employed in cases in which two or more analytes co-elute from a chromatographic column and the co-eluting analytes are simultaneously introduced into a mass spectrometer. As a second example, the novel teachings may be employed in cases in which two or more analytes are introduced into a mass spectrometer using a flow injection methodology. In yet a third example, the novel teachings may be employed in cases in which two or more analytes are introduced into a mass spectrometer using syringe infusion. In still yet other examples, the novel teachings may be employed in cases in which analytes are introduced into a mass spectrometer after separation by a capillary electrophoresis apparatus or a lab-on-a-chip apparatus. The novel methods may be employed in conjunction with mass spectrometers employing any known ionization technique that generates multiply-charged ions, such as, without limitation, electrospray ionization (ESI).

Accordingly, in a first aspect, there is disclosed a method for identifying the presence or absence of a protein/polypeptide or other biologically relevant compound within a liquid sample comprising a mixture of compounds that includes a plurality of protein compounds or a plurality of polypeptide compounds or pluralities of both protein and polypeptide or other compounds, wherein the method comprises: (a) introducing a portion or all of the liquid sample into an electrospray ionization source of a mass spectrometer; (b) forming positively-charged ions of the mixture of compounds of the portion of the liquid sample by electrospray ionization, the positively-charged ions comprising a plurality of ion species; (c) isolating a first subset of the ion species comprising a first mass-to-charge (m/z) ratio range that includes an m/z ratio of a multiply-protonated molecular species of the analyte compound; (d) generating a plurality of first-generation product ion species from the isolated first subset of ion species by causing the isolated first subset of ion species to be reacted, for a predetermined time duration, with reagent anions that, upon reaction, extract protons from each of one or more ion species that comprises a protonated species of a protein or polypeptide compound; (e) generating a mass spectrum, using a mass analyzer, of either the first-generation product ion species or of second-generation product ion species generated from the first-generation product ion species; (f) conducting a search of the mass spectrum of either the first-generation or the second-generation product ion species for a set of one or more m/z ratios that are diagnostic of the protein or polypeptide analyte compound; and (g) making a determination of the presence or absence of the analyte compound within the sample based on a measure of similarity between a set of m/z ratios identified in the mass spectrum and the set of one or more diagnostic m/z ratios. The measure of similarity may comprise a metric that is calculated based on a determined percentage or proportion of the one or more diagnostic m/z ratios that are found to occur in the measured set of identified m/z ratios. Alternatively, the presence of an analyte compound within the sample can be determined by comparing the measure of similarity between a set of m/z ratios identified in the mass spectrum and those contained in a protein, DNA, or carbohydrate based database; and (h) using the aforementioned information as a way to positively identify any unknown microorganism using spectral libraries, sequence based searching, statistical classification methods including but not limited to Bayesian, logistic regression, and decision tree classifiers. As an alternative to forming positively-charged ions in step (b), negatively-charged analyte ion species may be produced instead. In such cases, the reagent anions are chosen so as to transfer protons to the analyte ion species, thereby reducing the absolute values of their negative charges.

In a second aspect, there is disclosed a method of identifying the presence or absence of a microorganism type in a sample, comprising: (i) identifying a series of molecular weights whose simultaneous presence in the sample is diagnostic of the presence of the microorganism type(s) in the sample (ii) identifying a list of analyte compounds whose simultaneous presence in the sample is diagnostic of the presence of the microorganism type(s) in the sample, said list of analyte compounds comprising protein compounds, polypeptide compounds or both protein and polypeptide compounds; (iii) extracting, from the sample, a liquid solution comprising a mixture of sample-derived proteins and polypeptides; (iv) performing a set of analysis steps for each respective analyte compound in the list; and (v) identifying the presence of the microorganism(s) type within the sample if the presence of microorganism specific analyte compounds of the list of analyte compounds is identified within the liquid solution. The analysis steps that are performed for each respective analyte in the list comprise: (a) introducing a portion of the liquid solution into an electrospray ionization source of a mass spectrometer; (b) forming positively-charged ions of the mixture of compounds of the portion of the liquid solution by electrospray ionization, the positively-charged ions comprising a plurality of ion species; (c) isolating a first subset of the ion species comprising a first mass-to-charge (m/z) ratio range that includes an m/z ratio of either a random or particular predetermined multiply-protonated molecular species of the respective analyte compound; (d) generating a plurality of first-generation product ion species from the isolated first subset of ion species by causing the isolated first subset of ion species to be reacted, for a predetermined time duration, with reagent anions that spontaneously extract protons from each of one or more ion species that comprises a protonated species of a protein or polypeptide compound; (e) generating a mass spectrum, using a mass analyzer, of either the first-generation product ion species or of second-generation product ion species generated from the first-generation product ion species; (f) conducting a search of the mass spectrum of either the first-generation or the second-generation product ion species for a set of one or more m/z ratios that are diagnostic of the respective analyte compound; and (g) identifying the presence of the respective analyte compound within the liquid solution based on a measure of similarity between a set of m/z ratios identified in the mass spectrum and the set of one or more diagnostic m/z ratios. The measure of similarity may comprise a metric that is calculated based on a determined percentage or proportion of the one or more diagnostic m/z ratios that are found to occur in the measured set of identified m/z ratios. The diagnostic m/z ratios can be derived from a spectral library or sequence database. If the m/z ratio that is isolated in step (c) is of a random multiply-protonated molecular species, then the search conducted in step (f) is a sequence-based search. Otherwise, if the m/z ratio that is isolated in step (c) is of a particular predetermined multiply-protonated molecular species, then a spectral library search is conducted in step (f). In addition to using the aforementioned information as a way to positively identify an unknown microorganism using spectral libraries or sequence based searches, statistical classification methods including but not limited to Bayesian, logistic regression, and decision tree classifiers can be utilized for microbial characterization and identification. As an alternative to forming positively-charged ions in step (b), negatively-charged analyte ion species may be produced instead. In such cases, the reagent anions or cations are chosen so as to transfer protons to the analyte anion species, thereby reducing the absolute values of their negative charges. Control of the PTR experimental processes described herein can be performed manually or automatically in real-time using real-time spectral deconvolution.

The term "real-time spectral deconvolution" in the above refers to spectral deconvolution of mass spectral data that is performed concurrently with the mass spectral experiment or analytical run that generates (or that has generated) that mass spectral data. For example, mass spectral data acquired by mass analysis of analytes that elute at a first retention chromatographic retention time during a gradient elution may be deconvoluted, so as to identify the analytes, simultaneously with the continued collection of additional mass spectral data of additional analytes that elute at a second, later retention time during the same gradient elution. Likewise, deconvolution of the additional mass spectral data, so as to identify the additional analytes, may be performed simultaneously with the continued collection of mass spectral data of analytes that elute at a third elution time during the same gradient elution. The real-time spectral deconvolution may be facilitated by the use of a fast computer, such as a computer that employs parallel processing or a graphics processing unit (GPU) to perform the necessary calculations. Alternatively or additionally, the real-time spectral deconvolution may be facilitated by the use of a computationally efficient or optimized algorithm, such as an algorithm that is written at least partially in assembly language or that makes extensive use of in-cache look-up-tables. Advantageously, and as provided by the deconvolution computational methods in accordance with the present teachings (described in the appendix), the mathematical computations will not introduce any significant delays (i.e., greater than 1.0 seconds) into the work flow, taken with respect to the same workflow in the absence of the execution of the deconvolution computations.

More generally, the term "real-time" may be understood as meaning, when used in reference to an event or activity associated with a data acquisition process, that the event or activity occurs while some aspect or sub-process of that data acquisition process is ongoing. The data acquisition process itself may include one of more the following individual sub-processes: sample purification (e.g., solid phase extraction, size-exclusion chromatography); sample separation (e.g., chromatography); sample transfer into a mass spectrometer (e.g., infusion or inletting of eluate from a chromatograph); sample ionization in an ion source to as to generate first-generation ions; selection and isolation of ions for further manipulation; causing fragmentation of sample-derived ions or reaction of sample-derived ions with reagent ions so as to generate a first-generation of product ions; optional selection and isolation of product ions; optional further fragmentation of product ions or further reaction of product ions; transfer of ions (first-generation ions or first-generation or subsequent-generation product ions) to a mass analyzer, detection and measurement of ion mass-to-charge ratios by a detector of the mass analyzer; and transfer of data derived from the detection and measurement to a digital processor for storage, mathematical analysis, etc. The events or activities that may occur in "real-time", so defined, may include, but are not necessarily limited to: determination or identification of the presence of an analyte in a sample; identification or determination of the presence of a microorganism in a sample and providing a notification to a user of the identification or determination of the presence of an analyte or microorganism in a sample.

The above-described and various other features and advantages of the present teachings will become more fully apparent from the following description and appended claims, or may be learned by the practice of the invention as set forth hereinafter.

BRIEF DESCRIPTION OF DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 9A is a full scan mass spectrum of first-generation ions generated from eluate at a retention time of 10 min. and 30 s. during the course of a ten-minute gradient reverse-phase liquid chromatography separation of an *E. coli* extract;

FIG. 11D is a PTR product ion spectrum generated by reaction of PTR reagent ions with an isolated population of ions of the sample of FIG. 11C within a 10 Th wide isolation window centered at 750 Th;

FIG. 13 is a set of chromatograms collected from a single liquid chromatography-mass spectrometry experimental run of an *E. Coli* extract, including a total ion current chromatogram (top curve) and also illustrating various extracted ion chromatograms (lower curves) that contribute to the total ion current, each extracted ion chromatograph representing a respective m/z ratio range;

FIG. 20A and continuations FIGS. 20B, 20C and 20D, is a table showing typical molecular weights, expected number of $C^{13}$ atoms in the most abundant isotope (mode), expected average number of $C^{13}$ atoms among all isotopes and the difference between the expected average number and the mode, as they vary with the total number of $C^{12}$ atoms in a protein;

FIGS. 21A, 21B, 21C and 21D are depictions of computer screen user interfaces which may be employed in conjunction with user control of and information display from computer software that employs methods in accordance with the present teachings;

MODES FOR CARRYING OUT THE INVENTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the claims. The particular features and advantages of the invention will become more apparent with reference to the appended FIGS. 1-11D taken in conjunction with the following description in the main body of this document as well as FIGS. 12A-25D taken in conjunction with the description in the appendix to this document.

Figure 1:
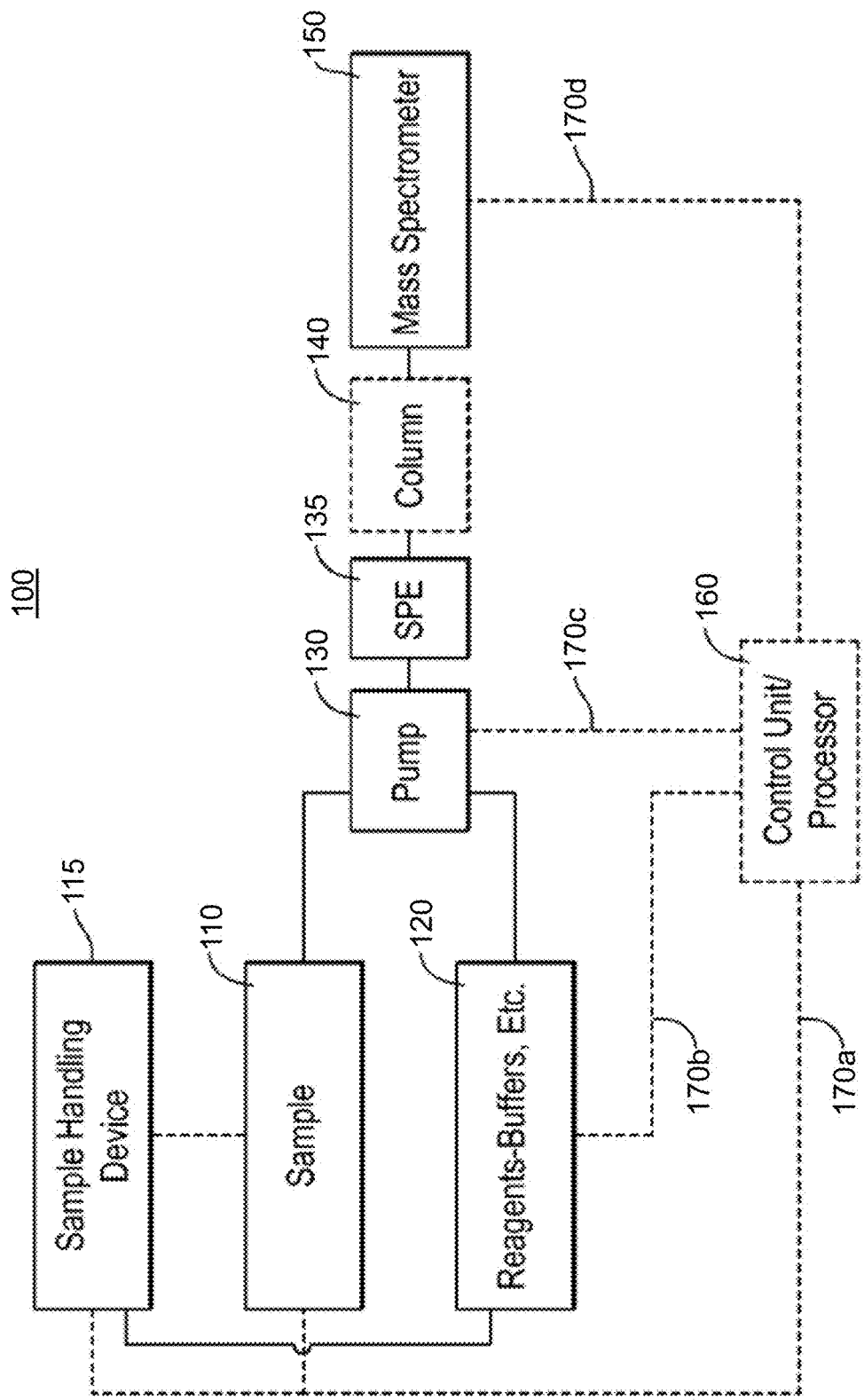
FIG. 1 is a block diagram schematically illustrating a system for rapid extraction and analysis of soluble proteins from at least one microorganism for identifying the at least one microorganism.

Referring now to FIG. 1, a system 100 for extraction of proteins from one or more microorganisms, detection of the proteins, and identification of the one or more microorganisms is schematically illustrated. The system 100 includes a sample handling device 115, a sample 110 that is accessible by the sample handling device 115, and sources of reagents, buffers, and the like 120, these sources being fluidly coupled to the sample handling device 115 by various tubing or other transfer lines. The system 100 further includes a first and, optionally, a second sample-purification device 135 (such as a solid phase extraction cartridge) configured for cleaning up samples (e.g., desalting, removing contaminants, concentrating proteins) and an optional chromatography column 140 that may be configured for at least partially purifying a sample 110 by liquid chromatography prior to mass-spec analysis. At least one sample-purification device 135 can comprise an in-line size exclusion chromatography column that can be used to not only remove salts but small molecules and lipids as well. The sample 110, the first and optional second sample-purification devices 135, and the optional chromatography column 140 are in fluid communication with a fluid handling pump 130, the various reagents, buffers and other fluids 120, and a mass spectrometer 150.

The sample handling device 115 is capable of preparing a range of sample types containing one or more microbes and delivering a soluble protein fraction extracted from the microbes to the mass spectrometer 150 for analysis. A sample 110 may be of any type suspected to contain one or more microorganisms including, without limitation, isolated colonies from a culture plate, cells from liquid growth medium, blood, blood culture, saliva, urine, stool, sputum, wound and body site swabs, soil, food, beverage, water, air, and environmental surface swabs.

The sample handling device 115 may include one or more of a cell disruption means, a robotic liquid handling means, a centrifuge, filtration means, an incubator, mixing means, a vacuum pump, a fluid pump, and reagents 120 that can be used for disruption of microbes and isolation of a soluble protein fraction. Disruption of bacterial, fungal, *mycoplasma* cells, viruses, and the like may be achieved by mechanical, chemical, enzymatic and other means as are commonly known in the art. Mechanical approaches include bead beating, use of pressure like French press and the like, sonication or other methods known in the art. Chemical methods include exposure to chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution.

As illustrated in FIG. 1, the system 100 further includes an optional control unit 160 that can be linked to various components of the system 100 through linkages 170a-170d. For example, the control unit 160 can be linked to the sample 110 to control sample application, the reagents 120 to control the application of various reagents, the pump 130 to control fluid handling, flow rates, etc., to the sample handling device 115 to control sample preparation, and to the mass spectrometer 150 to control mass spectrometry parameters. In the illustrated embodiment, the control unit 160 can also serve as a data processing unit to, for example, process data from the mass spectrometer 150 or to forward the data to server(s) for processing and storage (the server is not shown in FIG. 1). Control unit 160 can also determine molecular weights and charge states of any generation of PTR product ions for MS/MS, $MS^n$, or molecular weight determination in real time. The Control Unit 160 can also be used to automatically forward the results to health care professionals.

In some embodiments, the system 100 is designed to be used by a clinician or a general laboratory technician who is not necessarily expert in all aspects of sample preparation, LC-MS operations, LC-MS methods development, and the like. As such, the control unit 160 can be designed to encapsulate the data system environment by providing a user with a simplified application interface that can be used to initiate and monitor essentially all aspects of assaying a sample 110 without requiring the user to interact with the overall hardware and control systems of the system 100. The control unit 160 is therefore configured to provide a degree of separation between the user and the underlying services that control devices, data files and algorithms for translating data to a user readable form. That is, the control unit 160 eliminates the need for the user to be aware of or in control of hardware for analyzing clinical samples and provides a simplified interface to send and receive information from the mass spectrometer.

The control unit 160 may be configured to internally monitor each sample analysis request and is capable of tracking the analysis request from start to finish through the system 100. Once data for a sample 110 is being acquired or has been acquired by the system 100, the control unit 160 may be configured to automatically start post processing the data based on the type of assay selected by the user. Most importantly, the control unit 160 can be configured to process data in real time during the acquisition process. Here results are returned to the user in real-time that include microbial identification, virulence and resistance characterization, strain matching information, and data on antibiotic susceptibility testing. Moreover, the control unit 160 can be configured to automatically select post-processing parameters based on the type of assay selected by the user, further reducing the need for the user to interact with the system once the assay has been selected and started for analysis. The control unit 160 can be designed as a layer that fits between the system 100 and the user to reduce the complexity needed to set up sample assays for acquisition. The control system 160 can also be configured to return only the most relevant data to the user to avoid overwhelming the user with extraneous information.

In one embodiment, the system 100 can further include a sample detection device (not pictured) operably coupled to or integrated with the sample handling device 115. The sample detection device can work with the sample handling device 115 or independently of the sample handling device 115 perform at least one of the following functions: i. identify samples entering the system; ii. identify assay types for the samples entering the system; iii. select an assay protocol based on the anticipated assay type and/or analyte of interest; iv. direct the sample handling device and/or the control system to initiate analysis of the analyte of interest in the sample; v. direct the control system to select one or more reagents based upon the assay protocol selected for the type of assay and/or analyte of interest; vi. direct the control system to select a liquid chromatography mobile phase condition based upon the assay protocol selected for the type of assay and/or analyte of interest and cause the liquid chromatography system to perform the assay and/or purify the analyte of interest; vii. direct the control system to select a mass spectrometer setting based upon the assay protocol selected for the assay type and/or analyte of interest and cause the mass spectrometer to create mass spectral data associated with the selected assay type and/or analyte of interest; and viii. direct the control system to analyze the mass spectral data associated with the selected assay type and/or analyte of interest to identify the presence and/or concentration of the analyte of interest.

The sample, or the processed sample, may be cleaned up and or purified prior to analysis by mass spectrometry. Such purification, or sample clean-up, may refer to a procedure that removes salts or lipids from the crude cell extract, or to a procedure that enriches one or more analytes of interest relative to one or more other components of the sample. It also may refer to sample processing and clean-up in a separate laboratory that has biosafety level-three facilities for handling mycobacteria or filamentous fungi. In this embodiment samples are transferred to the system and can be analyzed as described previously. In one embodiment, such purification, or sample clean-up, may be accomplished by a solid phase extraction device, in-line size exclusion chromatography and/or the optional chromatography column 140.

In one embodiment, the first and/or second sample-purification device 135 may include a solid phase extraction (SPE) cartridge. In some embodiments, the SPE cartridge may be in line directly with the high resolution/high mass accuracy mass spectrometer 150. In one embodiment, the SPE cartridge may be a polypropylene tip with a small volume of silica or other sorbent containing bonded $C_4$, $C_8$ or $C_{18}$ or other functional groups immobilized in the cartridge, for example, a StageTip™ cartridge (Thermo Fisher Scientific). In alternative embodiments, polymeric sorbents or chelating agents may be used. The bed volume may be as small as 1 µL or less but greater volumes may also be used. The apparatus and method are well suited to the complex samples derived from the microbial cells because each SPE cartridge is used only once, minimizing carryover problems from one sample to another.

In one embodiment, a sample-purification device 135 may be an in-line size-exclusion chromatography column designed to remove salts, small molecules, and lipids from the sample 110. The approach can be used to separate medium and large molecular weight proteins as well. Phases are selected to be compatible with partial (i.e., less than 100 percent) organic solutions and organic acids. Phases can accommodate protein size distributions that differ in molecular weight from 103 to 108 Da. Flow rates are adjusted in real time to effect separation of intact proteins from small molecules with separation flow rates typically much less than the higher flow rates used to remove small molecules, lipids, and salts from the system. In this embodiment, a sample-purification device 135 may also be heated to facilitate faster diffusion rates for intact proteins, thus significantly shortening run times. The flow of mobile phase through a sample-purification device 135 may also be diverted during a portion of the clean-up process to remove certain impurities from the flow stream and prevent them from entering the mass spectrometer 150.

In one embodiment, the optional chromatography column 140 may include a column configured for at least partial chromatographic separation of the proteins in the sample. The stationary phase in the chromatography column may be porous or non-porous silica or agarose particles, or a monolithic material polymerized or otherwise formed inside the column. The stationary phase may be coated with an appropriate material such as $C_{18}$, $C_8$, $C_4$ or another suitable derivative, or contain cation exchanger or other material, or the combination of the above to facilitate the separation of the proteins, and such material may be chemically bonded to the particles or monolith inside the column. Particle sizes typically range from about 1.5 µm to 30 µm. Pore sizes can range from 50 to 300 angstroms. Inside diameters of columns typically range from about 50 µm to 2.1 mm, and column length from about 0.5 cm to 25 cm, or other. The mobile phase or eluent may be a pure solvent, or a mixture of two or more solvents, and may contain added salts, acids and/or other chemical modifiers. The proteins are separated on the column based on one or more physiochemical properties, including size, net charge, hydrophobicity, affinity, or other physiochemical properties. Chromatographic separation methods include one or more of ion exchange, size exclusion, HILIC, hydrophobic interaction, affinity, normal-phase, or reverse-phase chromatography.

Additional methods of purifying the samples may include, without limitation, liquid chromatography, HPLC, UHPLC, precipitation, solid-phase extraction, liquid-liquid extraction, dialysis, affinity capture, electrophoresis, filtration, ultra-filtration or other suitable methods known in the art for purification.

Various methods have been described involving the use of HPLC for sample clean-up prior to mass spectrometry analysis. One of skill in the art can select HPLC instruments and columns that are suitable for use in the invention. The chromatographic column typically includes a medium (i.e., a packing material) to facilitate separation of chemical moieties in space and time. The medium may include very small particles, which may have a bonded surface that interacts with the various chemical moieties to facilitate separation of the analytes of interest. One suitable bonded surface is a hydrophobic bonded surface such as an alkyl bonded surface. Alkyl bonded surfaces may include $C_4$, $C_8$, or $C_{18}$ bonded alkyl groups. In addition, monolithic and other phases known in the state of the art may be used as well. The chromatographic column includes an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used sequentially or as a two-dimensional (2D) chromatography system wherein a test sample may be applied to a first column at the inlet port, eluted with a solvent or solvent mixture onto a second column, and eluted with a solvent or solvent mixture from the second column to the outlet port. Different solvent modes may be selected for eluting the analytes. For example, liquid chromatography may be performed using a gradient mode, an isocratic mode, or a polytyptic (i.e. mixed) mode.

Figure 2:
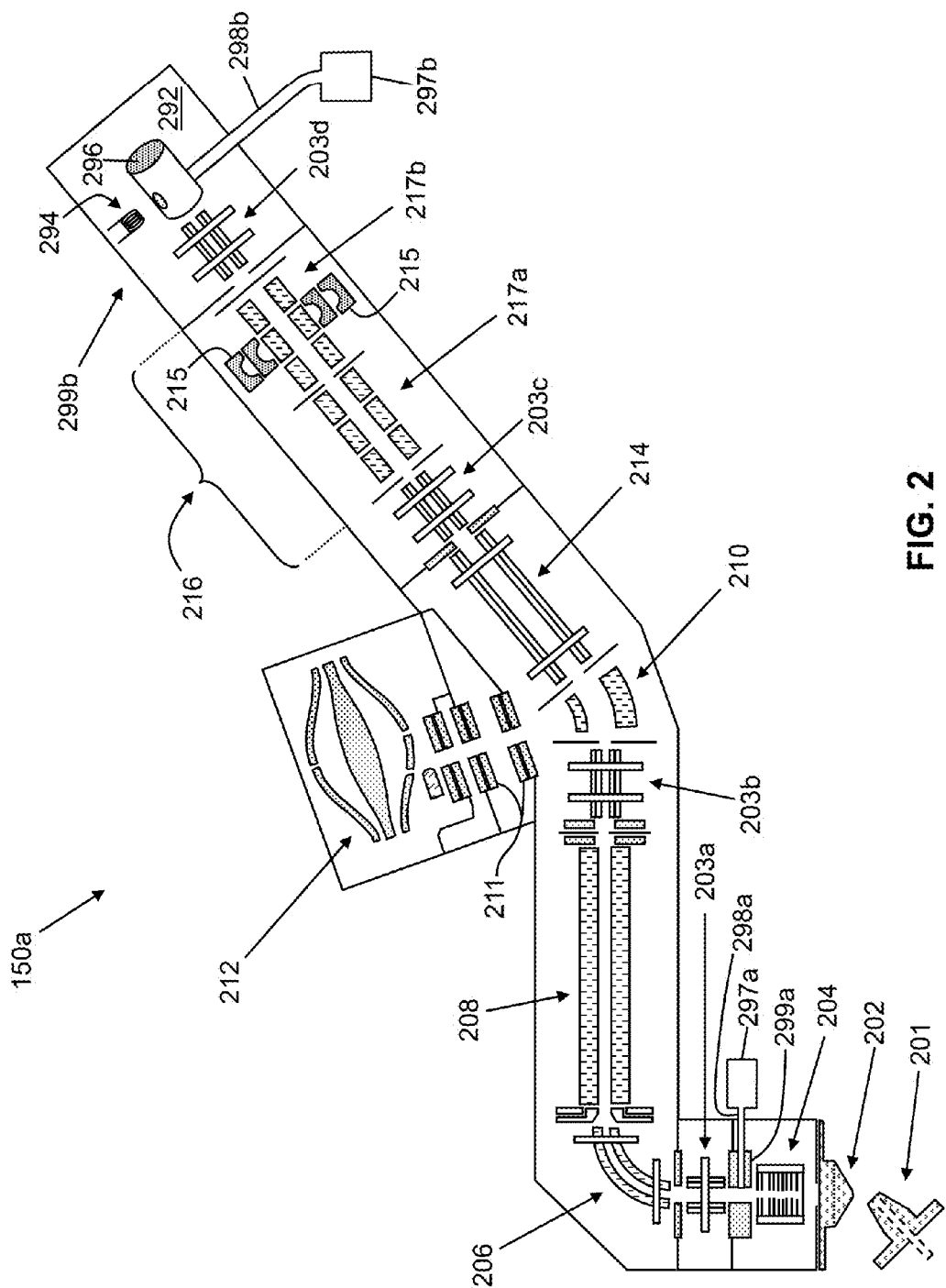
FIG. 2 is a schematic representation of an exemplary mass spectrometer suitable for employment in conjunction with methods according to the present teachings, the mass spectrometer comprising a hybrid system comprising a quadrupole mass filter, a dual-pressure quadrupole ion trap mass analyzer and an electrostatic trap mass analyzer.

FIG. 2 is a schematic depiction of an exemplary mass spectrometer 150a which may be employed as the mass spectrometer 150 of FIG. 1. The mass spectrometer illustrated in FIG. 2 is a hybrid mass spectrometer, comprising more than one type of mass analyzer. Specifically, the mass spectrometer 150a includes an ion trap mass analyzer 216 as well as an Orbitrap™ analyzer, which is a type of electrostatic trap mass analyzer. Since, as will be described below, various analysis methods in accordance with the present teachings employ multiple mass analysis data acquisitions, a hybrid mass spectrometer system can be advantageously employed to improve duty cycles by using two or more analyzers simultaneously. The Orbitrap™ mass analyzer 212 employs image charge detection, in which ions are detected indirectly by detection of an image current induced on an electrode by the motion of ions within an ion trap.

In operation of the mass spectrometer 150a, an electrospray ion source 201 provides ions of a sample to be analyzed to an aperture of a skimmer 202, at which the ions enter into a first vacuum chamber. After entry, the ions are captured and focused into a tight beam by a stacked-ring ion guide 204. A first ion optical transfer component 203a transfers the beam into downstream high-vacuum regions of the mass spectrometer. Most remaining neutral molecules and undesirable high-velocity ion clusters, such as solvated ions, are separated from the ion beam by a curved beam guide 206. The neutral molecules and ion clusters follow a straight-line path whereas the ions of interest are caused to bend around a ninety-degree turn by a drag field, thereby producing the separation.

A quadrupole mass filter 208 of the mass spectrometer 150a is used in its conventional sense as a tunable mass filter so as to pass ions only within a selected narrow m/z range. A subsequent ion optical transfer component 203b delivers the filtered ions to a curved quadrupole ion trap ("C-trap") component 210. The C-trap 210 is able to transfer ions along a pathway between the quadrupole mass filter 208 and the ion trap mass analyzer 216. The C-trap 210 also has the capability to temporarily collect and store a population of ions and then deliver the ions, as a pulse or packet, into the Orbitrap™ mass analyzer 212. The transfer of packets of ions is controlled by the application of electrical potential differences between the C-trap 210 and a set of injection electrodes 211 disposed between the C-trap 210 and the Orbitrap™ mass analyzer 212. The curvature of the C-trap is designed such that the population of ions is spatially focused so as to match the angular acceptance of an entrance aperture of the Orbitrap™ mass analyzer 212.

Multipole ion guide 214 and optical transfer component 203b serve to guide ions between the C-trap 210 and the ion trap mass analyzer 216. The multipole ion guide 214 provides temporary ion storage capability such that ions produced in a first processing step of an analysis method can be later retrieved for processing in a subsequent step. The multipole ion guide 214 can also serve as a fragmentation cell. Various gate electrodes along the pathway between the C-trap 210 and the ion trap mass analyzer 216 are controllable such that ions may be transferred in either direction, depending upon the sequence of ion processing steps required in any particular analysis method.

The ion trap mass analyzer 216 is a dual-pressure quadrupole linear ion trap (i.e., a two-dimensional trap) comprising a high-pressure linear trap cell 217a and a low-pressure linear trap cell 217b, the two cells being positioned adjacent to one another separated by a plate lens having a small aperture that permits ion transfer between the two cells and that presents a pumping restriction and allows different pressures to be maintained in the two traps. The environment of the high-pressure cell 217a favors ion cooling, ion fragmentation by either collision-induced dissociation or electron transfer dissociation or ion-ion reactions such as proton-transfer reactions. The environment of the low-pressure cell 217b favors analytical scanning with high resolving power and mass accuracy. The low-pressure cell includes a dual-dynode ion detector 215.

The use of either a step of electron transfer dissociation or proton transfer reaction within a mass analysis method requires the capability of causing controlled ion-ion reaction within a mass spectrometer. Ion-ion reactions, in turn, require the capabilities of generating reagent ions and of causing the reagent ions to mix with sample ions. The mass spectrometer 150a, as depicted in FIG. 2, illustrates two alternative reagent-ion sources, a first reagent-ion source 299a disposed between the stacked-ring ion guide 204 and the curved beam guide 206 and a second reagent-ion source 299b disposed at the opposite end of the instrument, adjacent to the low-pressure cell 217b of the linear ion trap mass analyzer 216. Generally, any particular system will only include one reagent ion source at most. However, two different reagent ion sources are depicted and discussed here for illustrative purposes. Although the following discussion is directed to reagent ion sources for PTR, similar discussion may apply to ETD reagent ion sources.

A first possible reagent ion source 299a may be located between the stacked ring ion guide 204 and the curved beam guide 206. The reagent ion source 299a comprises a glow discharge cell comprising a pair of electrodes (anode and cathode) that are exposed to a reagent gas conduit 298a that delivers the reagent gas from a reagent liquid (or solid) reservoir 297a having a heater that volatilizes the reagent compound. When a high voltage is applied across the electrodes, glow discharge is initiated which ionizes the reagent flowing between the electrodes. Reagent anions from the glow discharge source are introduced into the ion optics path ahead of the quadrupole mass filter 208 within which they may be m/z selected. The reagent ions may then be accumulated in the multipole ion guide 214, and subsequently transferred into the high pressure cell 217b of the dual-pressure linear ion trap 216 within which they are made available for the PTR reaction. The reaction products may be directly transferred to the low pressure cell 217a or to the Orbitrap™ mass analyzer 212 for m/z analysis.

A possible alternative reagent ion source 299a may be located adjacent to the low pressure linear trap cell 217b where it may comprise an additional high-vacuum chamber 292 from which reagent ions may be directed into the high pressure cell 217b through an aperture in between chamber 292 and the high-pressure cell. In operation, gaseous reagent compound is supplied from a reagent liquid (or solid) reservoir 297b having a heater that volatilizes the reagent compound and is directed through a reagent gas conduit 298b that delivers the reagent gas into a partially confined ion generation volume 296. In operation, thermionic electrons supplied from an electrically heated filament 294 are directed into the ion generation volume 296 with a certain pre-determined energy by application of an electrical potential between the filament 294 and an accelerator electrode (not shown). The supplied energetic electrons cause ionization of the reagent gas so as to generate reagent ions. The reagent ions may then be guided into the high pressure cell 217b by ion optical transfer component 203a under the operation of gate electrodes (not shown).

Figure 3A:
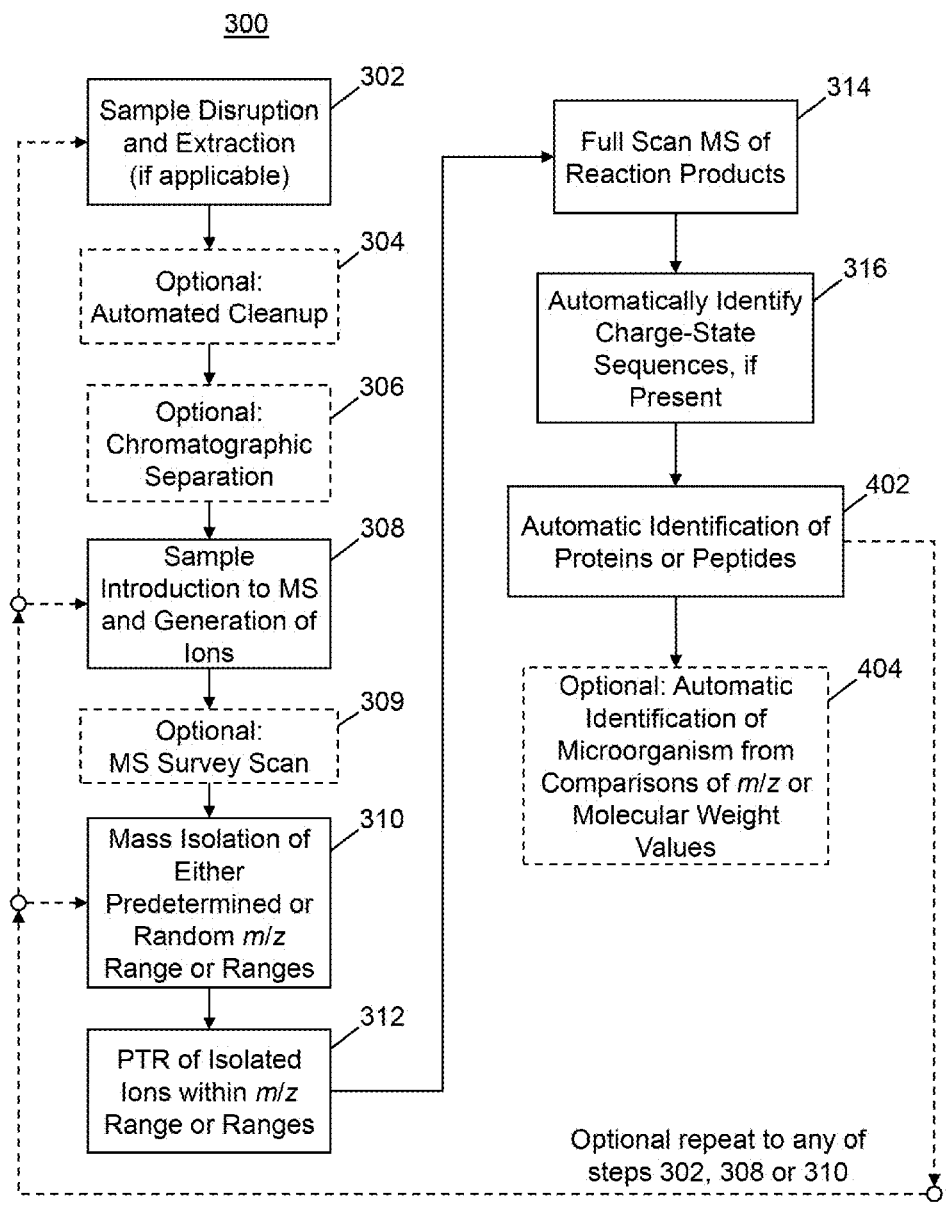
FIG. 3A is a flow diagram of a first method in accordance with the present teachings.

Exemplary methods in accordance with the present teachings are schematically illustrated in the flow diagrams shown in FIGS. 3A-3F. FIG. 3A schematically illustrates a first such exemplary method, method 300, for monitoring for the presence of and, optionally, quantifying, certain specific targeted analyte proteins or peptides in a biological sample. For example, the sample may be a sample of microorganisms. The initial steps 302, 304 and 306 of the method 300 are the steps of cell lysis (if the sample is a sample of microorganisms or other cells) and extraction, solid-phase clean-up, or size-exclusion chromatography and chromatographic separation, respectively, as described above. Step 302 may only be applicable if the sample comprises a tissue sample, a bacterial cell sample, a cell sample of another microorganism, or another form of cell sample. In some experimental situations, the extracted sample may be directly infused into a mass spectrometer in the subsequent sample introduction step 308; thus, the steps 304 and 306 are shown by dashed lines as being optional. Samples may also be prepared using offline approaches including dialysis, or other techniques known in the state of the art. However, in many other experimental situations, the steps 304 and 306 are useful so as to at least partially purify the sample prior to mass-spectral analysis.

When an analysis must be completed according to time constraints, as in some clinical applications, the required time for the analysis may be shortened by employing either a SPE step 304, a time-compressed chromatography step as described in U.S. Pat. No. 5,175,430 to inventor Enke, or the method of "Fast Partial Chromatographic Separation" (FPCS) in the chromatography step 306 as described in international (PCT) patent application publication WO 2013/166169 A1. Generally, in performing FPCS, a crude extract of microbial cells containing a complex mixture of various organic and inorganic analytes (small organic molecules, proteins and their naturally occurring fragments, lipids, nucleic acids, polysaccharides, lipoproteins, etc.) is loaded on a chromatographic column and subjected to chromatography. However, instead of allowing a gradient to elute each analyte separately (ideally, one analyte per chromatographic peak), the gradient is intentionally accelerated to the extent that substantially no chromatographic peaks obtained for example approximately eight minutes or less, and preferably five minutes or less instead of a much longer run time that would be required to obtain a baseline separation. In the FPCS separation, many analytes are intentionally co-eluted from the column at any given time according to their properties and the type of chromatography (reverse phase, HILIC, etc.) used. Partial or incomplete separation may be also accomplished by other methods known to one skilled in the art, including but not limited to the use of mobile phase solvents and/or modifiers that reduce retention of compounds on the column, selection of stationary phase media that reduce retention of compounds on the column (including particle size, pore size, etc.), operation of the chromatographic system at higher flow rate, operation of the chromatographic system at an elevated temperature, or selection of a different chromatographic separation mode (i.e., reversed-phase, size exclusion, etc.). The FPCS technique yields few or, possibly, no resolved chromatographic peaks across the whole gradient. Thus, substantially the only relevant information derived from a chromatogram is the time of elution from the column. Each mass spectrum that is recorded represents a "subset" of co-eluting analytes that is then ionized, separated in the mass analyzer and detected.

In step 308 (FIG. 3A), the sample is introduced into a mass spectrometer. The sample may be provided as the eluate material that emerges from an SPE cartridge, a chromatography apparatus or, alternatively, by direct infusion of the eluate solution. Upon being provided to the mass spectrometer, the sample compounds are ionized (step 308) by an electrospray ionization source of the mass spectrometer. These electrospray-generated ions are herein referred to as "first-generation" ions. At this juncture, a full or segmented $MS^1$ scan may optionally be performed (step 309) in order to identify the protein-rich regions in m/z space. (Note that in this document, the term "scan" may be taken to generally refer to a mass spectrum when used as a noun or, alternatively, to the acquisition of a mass spectrum, when used as a verb). In a preferred embodiment, the $MS^1$ scan can be obtained over the full mass range of the mass spectrometer instrument in order to be able to subsequently choose, in data-dependent or independent fashion, an information-rich portion of the spectrum for isolation (step 310). However, in the case of a targeted analysis, the $MS^1$ scan may be unnecessary and execution of the method 300 may proceed directly to step 310, in which a subset of the ions is then isolated for further reaction and analysis. When targeted analysis is employed, the isolation performed in step 310 may be such that ions within a certain pre-determined m/z range or possibly multiple pre-determined m/z ranges are retained for the subsequent reaction and analysis whereas ions outside the pre-determined m/z range or ranges are discarded. The pre-determined m/z range or ranges are chosen so as to correspond to preferably known m/z ratios of targeted analyte proteins or peptides whose presence or quantity is detected or monitored in the execution of the method.

Generally, the isolation of step 310 may be performed, in known fashion, by introducing the ions from the ion source into an ion trap—such as a three-dimensional ion trap, a curved ion trap (sometimes referred to as a "C-Trap") a single segment linear ion trap, multiple segmented linear ion trap, multipole ion guide or quadrupole mass filter—and then resonantly ejecting the ions whose m/z ratios are outside of the desired range by applying a supplemental AC voltage across pairs of electrodes of the ion trap or applying the appropriate RF/DC voltage ratios to isolate the ion population of interest. In some embodiments, the frequency of the supplemental voltage may be swept through various frequencies such that the ions are ejected in sequence according to their m/z ratios. In such cases, the ions may be detected as they are ejected so as to generate a mass spectrum of the original set of ions. However, since a mass spectrum may not be required at this stage, the supplemental AC voltage may be alternatively applied as a combination of superimposed frequencies that are chosen so as to cause essentially simultaneous ejection of the ions whose m/z ratios are outside of the desired range. In some embodiments, the combination of superimposed frequencies may be provided with multiple segments of missing frequencies (i.e., "notches") such that ions comprising two or more non-contiguous m/z ratio ranges are simultaneously isolated within the trap. Each one of the non-contiguous m/z ratio ranges may correspond to a preferably known m/z ratio of a respective unique targeted analyte protein or peptide. The applied RF/DC voltage ratios of a quadrupole mass filter may also be used to isolate the defined or targeted mass ranges of interest. Particular m/z ranges of the first-generation ions are selected by a single or series of fixed RF/DC voltage ratios in order to select the appropriate mass isolation windows. The instrumental configuration employed in this case may be a hybrid mass spectrometer instrument comprising a quadrupole, a C-trap, an Orbitrap™ mass analyzer, and a high energy collision cell (HCD) where the isolated ion population can be stored in either the C-trap or HCD cell for PTR experiments. The isolated population or populations of the first-generation ions are herein referred to as "precursor" ions, because these ions will be subjected to subsequent ion-ion reactions or to fragmentation.

In a preferred embodiment, the isolation of the precursor ion population may be performed in a first segment of a segmented linear ion trap. After isolation of the desired ion population, the multiply-charged protein ion population may be advantageously moved to another segment of the linear ion trap. These steps can be repeated multiple times for isolated defined ranges of precursor ions prior to the PTR process.

Next, anions are generated using either a rhenium-based filament with chemical ionization or glow discharge ionization source from a suitable high electron affinity based gaseous reagent. Ionization can be performed using nitrogen, methane, isobutane, or other known gases in the state of the art. The anion reagent may be a gas at room temperature or may be a liquid with sufficient vapor pressure to produce an excess of anions which will drive the PTR process under pseudo-first order reaction conditions. The anions are then transferred from the source region to the segmented linear trap whereby the specific anion reagent is mass isolated using supplemental AC voltages as described above. The anion source can be in-line with the electrospray source or mounted on the opposite end of the segmented linear ion trap. Alternatively, a quadrupole mass filter can perform the anion isolation as well with the subsequent PTR process occurring in the C-trap or HCD cell of the instrument.

In step 312 of the method 300 (FIG. 3A), the ions which were mass-isolated in step 310 (i.e., "precursor" ions) are subjected to a proton transfer reaction in which a reagent anion species is reacted for a specified time period with the sample precursor ions in the ion trap so as to extract protons from the precursor cations. In one embodiment, the multiply-charged precursor ion population and the singly-charged anion population are reacted by adjusting the DC voltage offsets of the segmented linear ion trap so as to store both the multiply-charged positive ions with the singly charged anions to facilitate the PTR process. The reagent anions are chosen such that, in this instance, the reagent anions behave as a Brønsted-Lowry base and such that the precursor ions behave as one or more Brønsted-Lowry acids. The reagent anions are formed by separate ionization of a suitable reagent gas/liquid with sufficient vapor pressure, that includes but is not limited to sulfur hexafluoride, perfluoro-1,3-dimethyl cyclohexane, perfluorodecalin, and perfluoroperhydrophenanthrene. After allowing the reaction to proceed for a specified time, a supplementary AC voltage is applied across electrodes of the ion trap so as to eject the reagent anions, thereby leaving product ions and, possibly, some residual precursor ions within the ion trap.

In the opposite polarity experiment, multiply-charged anions derived from proteins or other biomolecules can also be reacted with singly-charged cations. A variety of sources can be employed to generate singly-charged cations including electron, chemical, and electrospray ionization processes. These reactions follow the same reaction kinetics described previously. Typical reagent cations have included pyridine, benzo(f)quinolone, and the noble gases argon and xenon. In addition, multiply-charged proteins of opposite polarity have also been reacted as well as the multiply-charged anions from nucleic acids with the multiply-charged cations of proteins.

In step 314 of the method 300 (FIG. 3A), a mass spectrum is obtained of the product ions from the PTR process retained in the ion trap over a full range of m/z ratios of interest. The mass spectrum may be obtained, in known fashion, by detecting ions that are sequentially ejected from the 3D or linear ion trap in order of their m/z ratios. Alternatively, the ions may be directed to a different mass analyzer of the mass spectrometer, such as a Time-of-Flight (TOF) mass analyzer or an Orbitrap™-type of electrostatic trap mass analyzer, to be analyzed with greater accuracy or mass resolution then may be available by sequential scanning of the ion trap. Further, by directing the product ions to a separate analyzer, the ion trap may be re-filled with a new sample of precursor ions while the mass analysis is being performed. If the accurate mass analyzer is of a type—such as an FT-ICR mass analyzer or an Orbitrap™ mass analyzer—that detects image currents produced by cyclic ion motion within an ion trap, then the PTR reaction steps may advantageously reduce collision cross sections of targeted protein or polypeptide molecules such that these molecules remain stable in the trap for a sufficient length of time to generate high-quality mass spectra. Also, the PTR product ions will have less kinetic energy when leaving the high pressure C-trap region upon their transfer to the Orbitrap™ mass analyzer. Due to the PTR process, the resulting product ion population will be fully desolvated which will improve the quality of the resulting mass spectrum.

In step 316 of the method 300, the mass spectrum generated by the mass analysis performed in step 314 is automatically examined so as to recognize one or more individual series of related m/z ratios, wherein each m/z ratio of a series represents a respective different charge state—that is, a different degree of protonation—of a single intact protein or polypeptide molecule. For example, see FIG. 7C which depicts two different series of lines, represented by the envelope 905 and the envelope 906, respectively. After ionization as well as subsequent to the PTR reaction, each protein or polypeptide molecule, M, of mass $m_p$, is represented as at least one (and likely several different) protein or polypeptide cation species. Each such cation species of a related series formed from the particular molecule, M, may be represented by the chemical formula $(M+zH)^{z+}$, where the integer, z, is the number of protons adducted to the original molecule or is the number of protons remaining on the protein after the PTR step. In this example, considering only monoisotopic ions, the mass-to-charge ratio, $(m/z)_{ion}$, is thus given by:

$$(m/z)_{ion} \approx (m_p + z \times 1.007)/z \approx (m_p + z)/z \approx m_p/z \qquad (\text{Eq. 1})$$

where the final approximation results from the fact that $m_p \gg z$. Accordingly, such series of ion species representing only different states of protonation may be readily recognized by using automated software in real time to determine the monoisotopic ions. Once such series have been recognized, the molecular mass, $m_p$, of the parent protein or polypeptide molecule may be discerned in real time. Similar approaches can be applied to larger molecular weight molecules using average or monoisotopic mass as well. The automatic examination of the mass spectral data and recognition of one or more individual series of related m/z ratios may be performed by any one of many known mass spectral data analysis programs or software packages designed specifically for this purpose. However, for use in clinical applications or other time-critical applications, this automatic examination is preferably performed by an optimized computational method such as the computational methods that are described in detail in the appendix to this document.

The m/z values generated by the PTR process or, alternatively, the molecular weights obtained from the PTR product ions can then be searched against a database containing tabulated values of m/z values or molecular weights of proteins or polypeptides (step 402 of FIG. 3A) so as to recognize the presence of such analytes in the sample. If the sample is derived from a microorganism, then the database may relate to individual pathogen standards that contain the observed m/z values or molecular weights from known reference standards/patient samples. In such cases, by matching these m/z values or molecular weights from a database containing individual referenced pathogens, a small subset of possible pathogen identifications is obtained. The subset can be limited by determining a particular mass accuracy, weighting the intensities of the individual peak, and/or by weighting the molecular weight values by mass in a given scoring system.

In certain cases of microorganism studies, the m/z or molecular weight matches may provide a direct match to a particular pathogen identification which may be determined automatically (e.g, step 404 of FIG. 3A.). However, in all probability, the m/z molecular weight information will reduce substantially the number of possible pathogen identifications that can be unequivocally identified using tandem mass spectrometry. This process was originally described for use in conjunction with the steps 302, 304, 306, and 308-310 in international (PCT) patent application publication WO 2013/166169 A1. Additionally, Bayesian, logistic regression, or decision tree based methods can be employed to further refine the identification of the pathogen. In a preferred embodiment, this m/z or molecular weight search is performed in real time during data acquisition (i.e., as the sample is being analyzed). Alternatively, the search may be performed post-acquisition (i.e., after the sample has been analyzed) as well. The comparison of a small number of m/z values or molecular weights (3-10) of proteins to a reference database will generally be sufficient to significantly reduce the candidate number of pathogen identifications to five or less.

Optionally, execution of the method 300 may return back to any of steps 302, 308 or 310 after execution of step 402 as indicated by dashed arrows in FIG. 3A. This same option is also applicable to method 370 illustrated in FIG. 3B, the method 380 illustrated in FIG. 3C, the method 390 illustrated in FIGS. 3D-3E and the method 395 illustrated in FIG. 3F. Returning to step 302 corresponds to repeating the entirety of the method 300 in the analysis of a different sample. Returning to step 308 corresponds to introducing a different portion of a same sample into the mass spectrometer system and repeating the mass spectral analysis on the different portion. In some cases, the different portion of the same sample may comprise a different chemical fraction of the same sample (that is, it may comprise a different composition from the prior analyzed portion), if the sample is being chemically fractionated, e.g., by chromatography (step 306) or by some other chemical fractionation technique. In some cases, the different portion of the sample may comprise the same composition as the prior analyzed portion (or may be considered to comprise essentially the same composition) as the prior analyzed portion if there is no chemical fractionation step or if the rate of change of chemical composition caused by the fractionation is much slower than the rate at which the mass spectrometer system can repeat steps 312-402.

Returning to step 310 from step 402 corresponds to mass isolating a second, different predetermined m/z range or ranges of ion species in step 310 (as compared to the m/z range or ranges of ion species isolated in the prior execution of step 310) and then repeating steps 312-402 using the newly isolated ion species and their reaction products. This procedure of repeating steps 310-402 is particularly useful if it may be assumed that the sample composition has not changed between successive iterations of these steps. Under these circumstances, the repetition of steps 310-402 may provide additional information from the same sample composition. The sample may often be assumed to remain constant or negligibly different if there is no chemical fractionation prior to sample introduction into the mass spectrometer or if the rate of change of chemical composition caused by the fractionation is much slower than the rate at which the mass spectrometer system can repeat the steps 312-402.

Figure 3B:
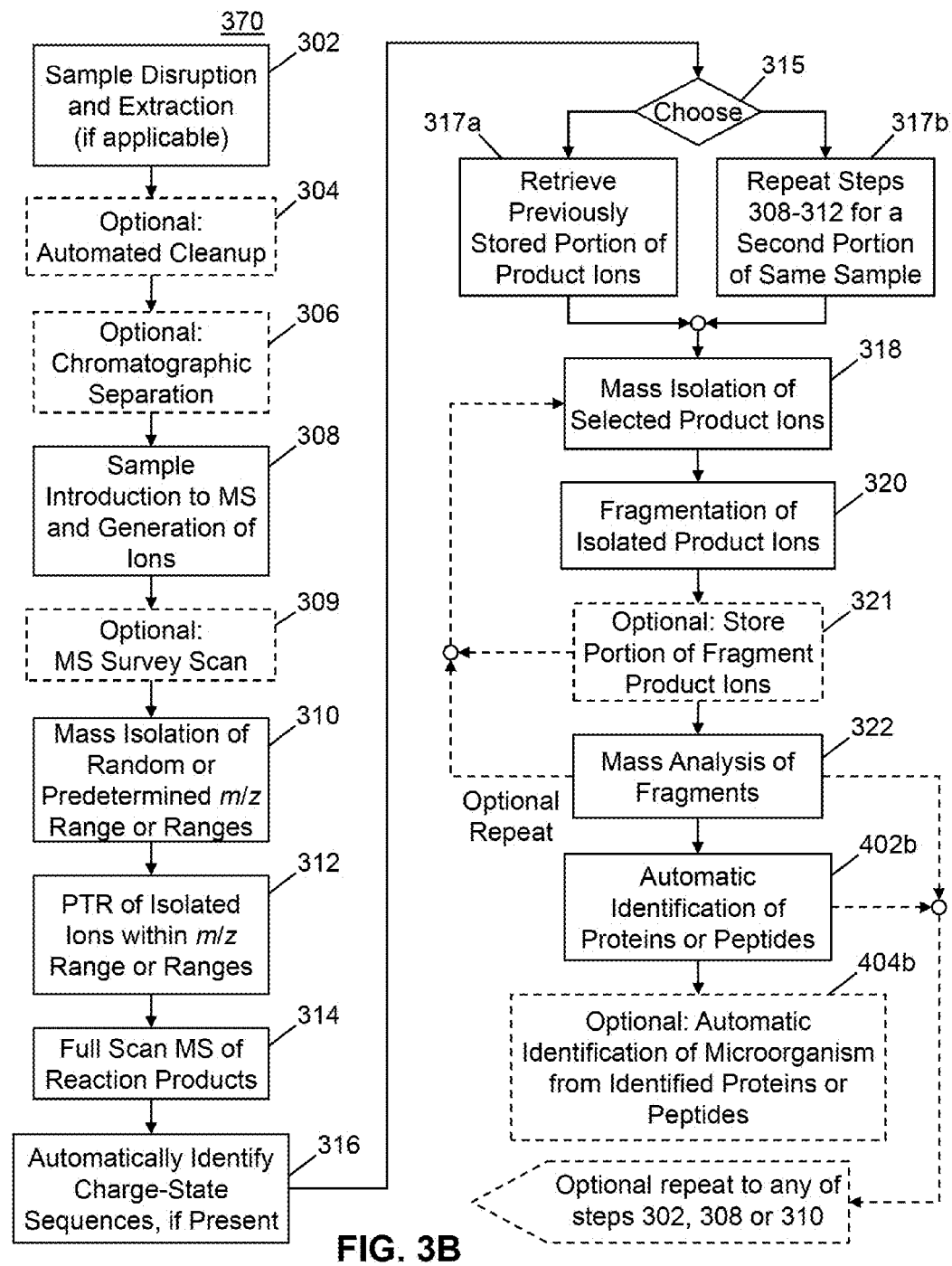
FIG. 3B is a flow diagram of an alternative method in accordance with the present teachings.

FIG. 3B schematically illustrates a flow diagram of a second exemplary method, method 370, in accordance with the present teachings. The steps 302-314 of the method 370 (FIG. 3B) are identical to the similarly numbered steps of the method 300 (FIG. 3A) and thus the description of these steps is not repeated here. The method 370 differs from the method 300 only with regard to the steps following the generation of a mass spectrum in step 314. According to the earlier-described method 300, the mass spectrum of PTR product ions is assumed to be sufficient to detect or quantify proteins and polypeptides of interest. However, in many cases, it may be necessary to perform tandem mass spectrometry (sometimes referred to as MS/MS or MS$^n$) after the generation of PTR reaction products in order to resolve remaining ambiguities in the recognition of specific protein or polypeptide molecules. In other cases, it may be necessary to perform a second stage of PTR as discussed further below. In cases in which fragmentation is required, the PTR reaction products may be considered to comprise a first generation of reaction products which are then fragmented to form a second generation of product ions. The combination of a specific m/z ratio of a first-generation reaction product with one or more specific m/z ratios of fragment ions may, in many cases, allow identification of a specific protein or polypeptide molecule associated with a given pathogen. In many instances the protein identified with a specific pathogen may also be found in other similar pathogens. In order to correctly identify a single pathogen, method 370 (specifically tandem mass spectrometry) may need to be performed on as many proteins that are present in a given PTR fraction, or multiple PTR fractions of the same sample.

In step 316 of the method 370, a computational method is performed so as to automatically analyze the mass spectral data of PTR reaction products obtained in step 314. The computational method attempts to identify charge-state sequences of proteins or polypeptides. The results of the real-time automatic computational analysis obtained in step 316 of the method 370 may be later used as a basis for making an m/z selection in the subsequent step 318, in which a subset of the PTR product ions, comprising a restricted range of m/z ratios, are selected and isolated so as to be later fragmented in step 320. Preferably, the automatic identification of charge-state sequences (step 316) is carried out by a fast computational method, such as the computational methods that are described in detail in the appendix to this document, that is optimized for such real-time data analysis.

Accordingly, steps 318-322 of method 370 (FIG. 3B) represent the application of the techniques of tandem mass spectrometry or selected reaction monitoring (SRM) as applied to the ions formed by PTR. If the particular employed mass spectrometry system permits, a portion of the PTR product ions may have already been stored (immediately after step 312) in an ion storage apparatus of the mass spectrometer system. In such cases, the branching step 315 causes execution of step 317a, in which the previously stored ions are retrieved for further processing. Otherwise, if the prior batch of PTR product ions was exhausted by the mass analysis step (step 314), then, in accordance with the alternative step 317b, the steps 308-312 may need to be re-executed in order to generate a new batch of such PTR product ions.

In step 318 of the method 370, certain of the PTR reaction-product ions (i.e., the first-generation product ions) within a particular m/z range or particular m/z ranges are mass isolated by ejecting ions whose m/z ratios are not within the range or ranges of interest. The isolated ions are subsequently fragmented in step 320. The particular chosen range or ranges will generally be responsive to the details of a particular identified charge-state sequence identified an immediately prior execution of step 316 and the choice will generally be made automatically by computer. Thus, the choice of a particular m/z range or ranges for isolation and fragmentation is an example of so-called "data-dependent analysis" (or "data-dependent acquisition", etc.).

Figure 7A:
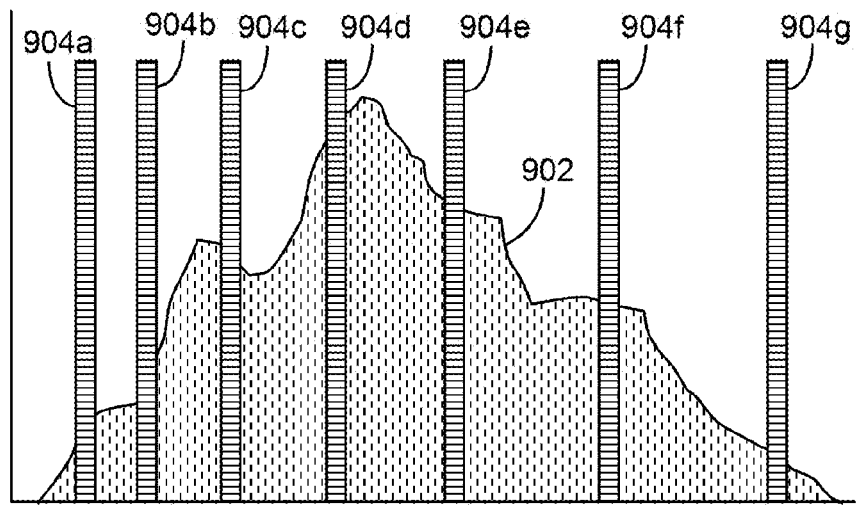
FIG. 7A is a schematic depiction of a method, in accordance with the present teachings, of improved-efficiency PTR conversion of ions of a selected analyte to an assemblage of PTR product ions by simultaneous isolation and reaction of multiple m/z ranges of electrospray-produced first-generation precursor ions.
Figure 7B:
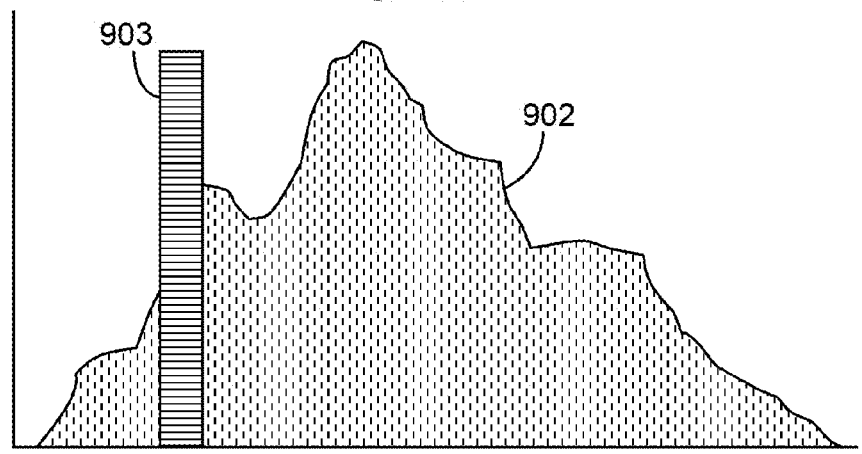
FIG. 7B is a schematic diagram of isolation of a first randomly-chosen range of electrospray-produced first-generation precursor ions for PTR reaction, as may be employed in an initial step of a method of improved-efficiency PTR conversion of ions.
Figure 7C:
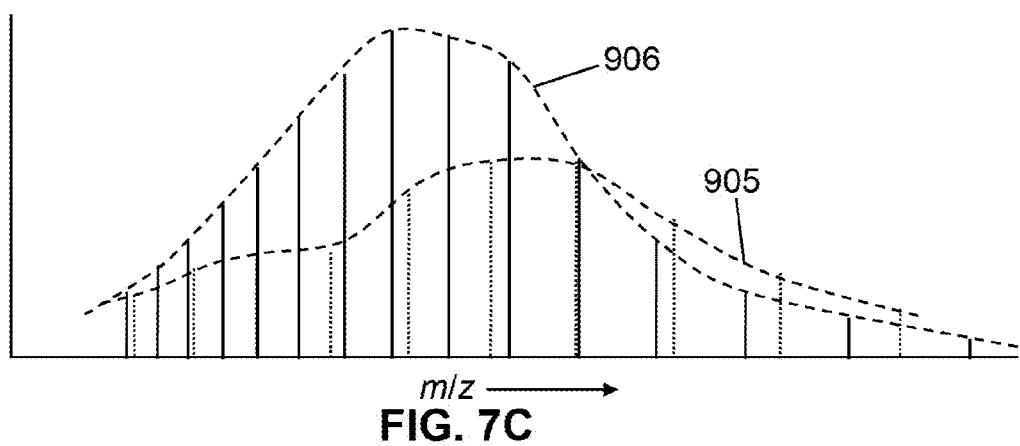
FIG. 7C is a schematic depiction of recognition of two charge-state sequences of PTR product ions corresponding to different analyte molecules, as may be employed as an intermediate step of a method of improved-efficiency PTR conversion of ions.

In most conventional MS/MS analyses, involving low-mass molecules of a few hundred to a few thousand Daltons, data-dependent fragmentation comprises choosing the "top P number of the most abundant precursors" for tandem mass analysis based on the information of a preceding $MS^1$ data acquisition, where the number P is either a constant or perhaps a variable input by a user. It has been found that this conventional form of data-dependent analysis does not perform well when used in the analysis of multicomponent samples of biopolymer analytes. For example, FIG. 7C illustrates two charge state distributions, denoted by the envelope 905 and the envelope 906, respectively. In this example, each envelope corresponds to a different respective analyte molecule species. Thus, the sets of lines encompassed by envelopes 905 and 906 may be referred to as "molecular-species-correlative charge-state distributions". Considering the lines (individual m/z values) in FIG. 7C to represent precursor ions, then if P=10, the conventional data-dependent fragmentation technique would choose the ten leftmost solid vertical lines under the envelope 906 for fragmentation. Using the conventional technique, none of the dotted lines corresponding to envelope 905 would be chosen. The conventional procedure would thus yield redundant information relating to the molecule species corresponding to envelope 906 and no information relating to the molecule species corresponding to envelope 905.

To overcome the shortcomings of conventional data-dependent fragmentation when applied to high-molecular-weight molecules, the inventors have developed the herein-used novel "top P unique analyte-specific clusters" data-dependent technique so as to replace, for application to high-molecular-weight molecules, the previous "top P number of the most abundant precursors" logic. Each molecular-species-correlative charge-state distribution is a set of related mass spectral lines (m/z values) which are interpreted, according to the novel "top P unique analyte-specific clusters" logic, to all be generated from a single unique molecule. Each molecular-species-correlative charge-state distribution groups together various charge states and isotopic clusters that are indicated to have been generated from a single molecule, prior to ionization. However, the molecular-species-correlative distribution excludes adducts, which are removed prior to data analysis. According to the novel method, fragmentation is performed only on one (or possibly more) selected representatives of a given molecular-species-correlative charge state distribution envelope thereby avoiding the redundancy noted above associated with the conventional data-dependent fragmentation method. According to the novel "top P unique analyte-specific clusters" logic, after a representative m/z ratio (or ratios) has been chosen for a first molecular-species-correlative charge-state distribution, any further fragmentation is directed to a representative m/z ratio of the next determined molecular-species-correlative charge-state distribution, and so on.

As previously described, the isolation performed in step 318 of the method 370 may be accomplished by applying a supplemental AC voltage across pairs of electrodes of an ion trap such that ions having m/z ratios that are not within the range or ranges of interest are ejected from the trap while those ions having m/z ratios that are within the range or ranges are retained within the trap. In some instances, the ion trap used for mass isolation may be identical to the mass analyzer used to conduct the full-scan mass analysis in step 314.

The supplemental AC voltage applied to the ion trap used for mass isolation may comprise a summation of superimposed frequencies such that ions within two or more non-contiguous m/z ranges are simultaneously isolated. In the subsequent step 320, the mass-isolated first-generation product ions are fragmented by a suitable ion fragmentation technique, such as collision induced dissociation (CID). The fragmentation may be accomplished by transferring the first-generation product ions (product ions formed by PTR of original precursor ions), in known fashion, to a dedicated fragmentation cell within which the transferred ions are fragmented so as to generate fragment ions, these fragment ions comprising a second generation of reaction products. Optionally, a portion of the fragment product ions may be stored for possible future additional fragmentation in optional step 321.

In step 322 of the method 370 (FIG. 3B), the fragments generated in step 320 are mass analyzed by a mass analyzer of the mass spectrometer. If the second-generation product ions are produced within a fragmentation cell that is specifically dedicated for the purpose of fragmentation, the ions must be first transferred to the mass analyzer prior to the execution of step 322. An ion trap mass analyzer may be employed to analyze the second-generation product ions in step 322, in which case the mass analyzer employed for step 322 may be identical to the mass analyzer employed to conduct the full-scan mass analysis of step 314. Alternatively, an accurate-mass analyzer capable of measuring mass-to-charge ratios to an accuracy of 10 ppm or better—such as an FT-ICR mass analyzer, a time-of-flight (TOF) mass analyzer or an Orbitrap™-type of electrostatic trap mass analyzer—may be employed for step 322.

As is known, the correlation between the m/z value of a certain selected ion species subjected to fragmentation and the m/z value (or values) of one or more fragment ion species produced by the fragmentation may be sufficient to automatically determine (in step 402b) the chemical identity of the selected ion species. In this case, the selected ion species is a PTR reaction-product species generated in step 312 that is mass-isolated in step 318. The identification of a small number (i.e., 3-10) of such proteins will generally be sufficient to uniquely identify a microorganism species (optional step 404b). However, a single stage of fragmentation may be insufficient for performing a chemical species identification. In such instances, the second generation product ions may be further fragmented so as to form a next generation of product ions, indicated by the optional repeat (indicated with dashed lines) from step 322 back to step 318 in which a selected subset of the fragment product ions are isolated, according to their m/z values, and the so-isolated fragment ions are further fragmented. More generally, a subset of the nth generation of product ions may be selected for further fragmentation by any suitable ion fragmentation method such as, but not limited to, collision-induced fragmentation, higher-energy collisional dissociation, electron transfer dissociation, electron capture dissociation, negative electron transfer dissociation, electron-detachment dissociation, surface-induced dissociation, or photodissociation, whereby an $(n+1)^{th}$ generation of product ions is formed. The results of the mass analysis step 322 may form the basis of an automated decision as to whether or not each additional fragmentation is required and, if so, which m/z values correspond to the ion species to be fragmented.

In the above discussion, the optional repeat from step 322 back to step 318 of the method 370 was described as for the purpose of further fragmenting previously-generated fragment ions. However, in some embodiments, the second or subsequent execution of step 318 may be for the purpose of choosing a second, different ion species of the PTR reaction products (generated and possibly stored in step 312) for fragmentation, based on the automatic identification of charge state sequences previously performed in step 316. The possible need for a second PTR step may be understood with reference now to FIG. 12C. As an example, a first execution of the mass isolation step (step 318 of method 370) may isolate an ion species corresponding to a mass spectral line belonging to charge state envelope A208, whereas a second execution of step 318 may isolate an ion species corresponding to one of the mass spectral lines belonging to charge state envelope A206. As described in the appendix to this document, each such set of mass spectral lines (the set belonging to envelope A208 or the set belonging to envelope A206). The novel "Top P Unique Analyte-Specific Clusters" workflow described in the appendix is specifically adapted to recognize such clusters corresponding to different respective potential analyte molecules. According to such a workflow procedure, the second execution of the isolation step (step 318) and the fragmentation step (step 320) of the method 370 are performed so as to exclude isolation and fragmentation of the ion species corresponding to the envelope A208 (assuming one such ion species was isolated and fragmented during an earlier execution of these steps), even though they may be of greater intensity than the ion species corresponding to envelope A206. In this way, fragment information about different potential analytes is obtained during each iteration of the optional loop comprising steps 318-322.

The method 300 diagramed in FIG. 3A, which was discussed above, provides a relatively simple and straightforward method of sample analysis that may be applicable for samples of relatively low complexity as, for example, when highly-resolved chromatographic separation (step 306) has been performed prior to introduction of a chromatographic fraction into a mass spectrometer (step 308). However, the simple method 300 may not be appropriate for more complex samples and the analysis of such samples may present a number of challenges. Firstly, the proteins present in a complex mixture have a wide range of molecular weights. Secondly, the large number of charge states that result from the presence of a large number of lysine, arginine, histidine residues may result in multiple overlapping sets of peaks, each set of peak corresponding to a different chemical species. Thirdly, if the mass analysis (step 314) is of sufficiently high resolution, the presence of resolved peaks of an isotopic distribution for any given charge state can confound most data processing algorithms. Finally, the distribution of available ions among multiple charge states and, possibly, among multiple isotopic states necessarily reduces the signal intensity of any resolved peak in the mass analysis.

Figure 3C:
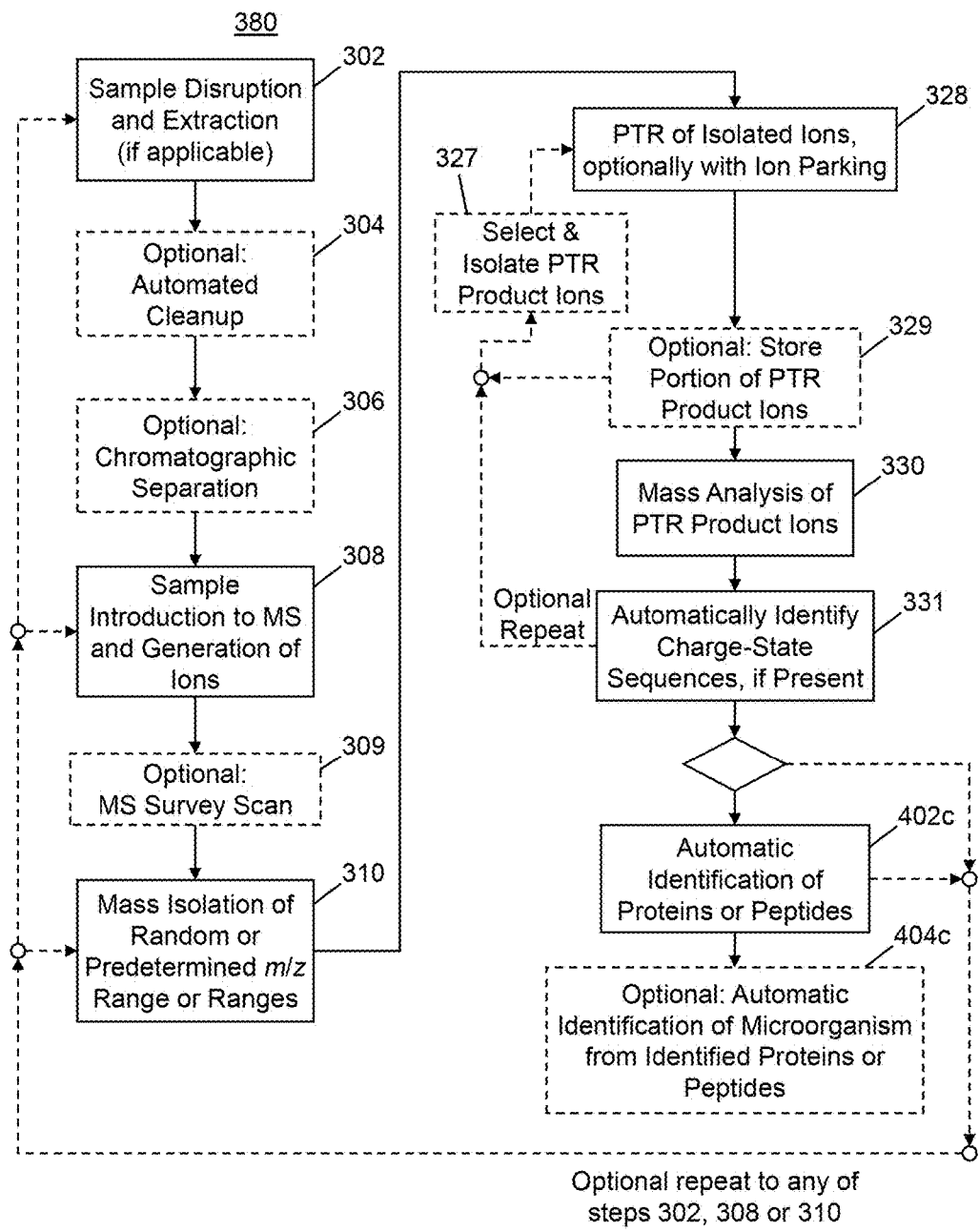
FIG. 3C is a flow diagram of another alternative method in accordance with the present teachings.

In order to address the above-noted challenges in the analysis of complex samples, the method 380, for which a schematic flow diagram is illustrated in FIG. 3C, provides the opportunity for conducting multiple PTR stages. Under the earlier-described method 300, it is assumed that the mass spectrum obtained (in step 314) of the first-generation PTR reaction products (generated in step 312) exhibits sufficient improvement in signal-to-noise ratio and sufficient reduction in isobaric interferences such that charge-state sequences may be recognized and that proteins or polypeptides may be identified. If such improvement in mass spectral quality remains inadequate for such purposes after a first PTR reaction event, then the additional refinement steps 327-330 of the method 380 (FIG. 3C) may be performed. Further, one or more of the PTR stages may utilize the known technique of "ion parking" in order to simplify the charge state distribution, as noted in the previous paragraph. Ion parking is a technique whereby specific selected ion/ion reactions within an ion trap are inhibited. In practice, a resonance excitation waveform is applied across electrode pairs of an ion trap, ion guide or other ion storage device in an amplitude that is insufficient to cause ion ejection but sufficient to increase the velocities of ions having selected m/z values. This excitation process increases the relative velocity between the excited ions (cations, for purposes of the present discussion) and reagent anions and it is believed that this relative velocity increase causes a reduction in the rates of reaction between the excited cations and reagent anions.

During the PTR process, the rate of reaction between cations and reagent anions varies as the square of the charge number of the various cations with the anion charge on the reagent ions equal to −1. Thus, in the absence of ion parking, the PTR process leads to a rapid reduction in the number of highly charged cations. Over the course of the reaction, the distribution of charge states of cations derived from a single molecular species, M (a protein or polypeptide molecule having mass $m_p$), shifts towards lower charge states. The population of each ion species having an intermediate charge state will first increase as the more-highly-charged precursor ions lose protons and then decrease as each respective species loses more protons then it gains from the diminishing quantity of more-highly-charged cations. The ultimate result, if the PTR reaction is allowed to proceed to completion, is complete neutralization of all such cations and total loss of all mass spectrometric signal.

When the ion parking technique is applied during the PTR reaction, then the charge reduction process is essentially stopped at the charge state, $z_1$, corresponding to the particular mass-to-charge ratio (for example, $m_p/z_1$) of the ions which are resonantly excited by the applied AC waveform. Those precursor cations derived from the molecular species, M, with initial charge states, z, such that $z > z_1$ will lose protons until their charge states are reduced to $z_1$, after which further reaction and proton loss will be inhibitied. Those precursor cations derived from the molecular species, M, with initial charge states, z, such that $z < z_1$ will be completely neutralized. Accordingly, after PTR reaction with ion parking, a significant portion of the original protonated molecular ions (i.e., precursor ions) of molecule M will be represented, in a mass spectrum, by the single ionic species having charge state, $z_1$. This "concentration" of the molecule species, M, into a single charge state can advantageously amplify the mass-spectrometric signal associated with that species, thereby improving signal-to-noise ratio and reducing the lower limit of detection and, optionally, the lower limit of quantification of the species. Further, many isotopic variants of ions generated from molecule species, M, will have m/z values outside of the range of values corresponding to the applied AC resonant excitation waveform. Such isotopic variants will be neutralized so as to not interfere with the mass spectrometric identification of ions of interest. Other isotopic variants comprise m/z values that are within the range of values corresponding to the applied AC resonant excitation waveform. The isotopic distribution pattern of such isotopically variant ions will be greatly simplified relative to the isotopic distribution observed in the original precursor ions because they will mostly relate to the single charge state, $z_1$ of ions generated from molecule, M.

Returning to the discussion of the method 380 outlined in FIG. 3C, it is to be noted that the steps 302-310 of the method 380 are identical to the similarly numbered steps of the method 300 (FIG. 3A) and are not re-described here. Subsequently, in step 328, precursor ions are subjected to PTR, optionally as modified by the ion parking technique. As previously noted, step 328 is executed by applying a supplemental AC excitation waveform across a pair of electrodes of an ion trap within which sample-derived cations are reacted with reagent anions for a predetermined time period. As described above, the employment of this "ion parking" procedure will concentrate the distribution of ions derived from any particular protein or polypeptide into a particular restricted range of m/z values. This will generally restrict the ions derived from any particular protein or polypeptide into a particular charge state, thereby simplifying a resulting mass spectrum and increasing the intensity of any mass spectral peaks corresponding to the particular protein or polypeptide. The particular range of m/z values into which the ions are restricted may comprise ions of different respective charge states derived from different respective molecular species. In some embodiments, the applied AC waveform used to effect the ion parking may comprise a summation of waveforms of different respective frequencies such that the summed waveform causes the PTR reaction to yield a final population of PTR product ions corresponding to two or more non-contiguous m/z ranges.

In the subsequent step 330, the population of PTR product ions produced in step 328 is mass analyzed by a mass analyzer and, in step 331, an automatic computation may be performed on the data produced in the mass analysis so as to automatically identify any charge-state sequences that may be represented in the data, where each such charge state sequence corresponds to a different potential protein or polypeptide analyte. Prior to the mass analysis of step 330, a portion of the PTR product ions may be stored (step 329) in preparation for possible subsequent PTR reaction. Depending upon the results of the automatic identification of charge state sequences (step 331), an automatic decision may be made to subject the PTR product ions to such further PTR reaction, as indicated by the dashed line optional pathways shown in FIG. 3C. The decision may also be made, based on the results of the automatic identification of charge state sequences, to only subject a selected subset of the PTR product ions to subsequent PTR reaction. In such cases, step 327 is executed. Thus, according to some embodiments, the steps 327-331 may comprise an iterated loop wherein, at each iteration of the loop, a different respective ion species, corresponding to a different respective protein or polypeptide is selected and isolated for further purification by the PTR process. The ion species that are selected in this fashion may be determined in step 331 from in accordance with the novel "Top P Unique Analyte-Specific Clusters" workflow described in the appendix to this document.

If the mass analyzer employed in step 330 is of a type that detects image currents produced by cyclic ion motion within an ion trap or other ion storage device—such as an FT-ICR mass analyzer or an Orbitrap™ mass analyzer—then the PTR reaction steps may advantageously reduce collision profiles of targeted protein or polypeptide molecules such that these molecules remain stable in the trap for a sufficient length of time to generate high-quality mass spectra. After a sufficient number of PTR reaction steps, the chemical identity of the protein or polypeptide may then be rapidly discerned (in step 402c) by matching to databases of known molecular masses. The identification of a small number of (3-10) of proteins will generally be sufficient to uniquely identify a microorganism species (optional step 404c). Identification can also be accomplished via the use of classifiers applied to the PTR data as discussed previously that includes but is not limited to Bayesian, logistic regression or decision tree based approaches.

Figure 3D:
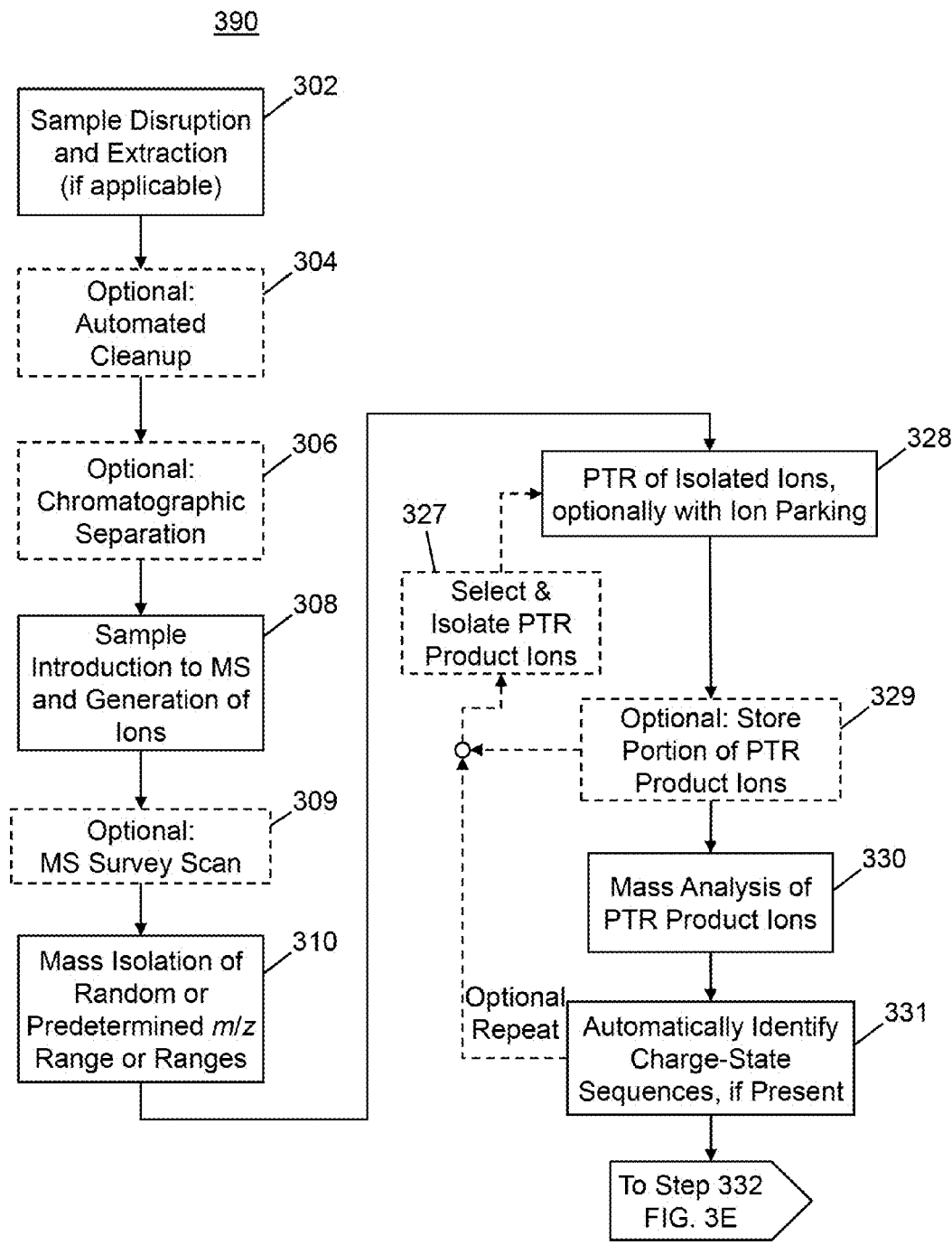
FIG. 3D and FIG. 3E illustrate a flow diagram of yet another alternative method in accordance with the present teachings.
Figure 3E:
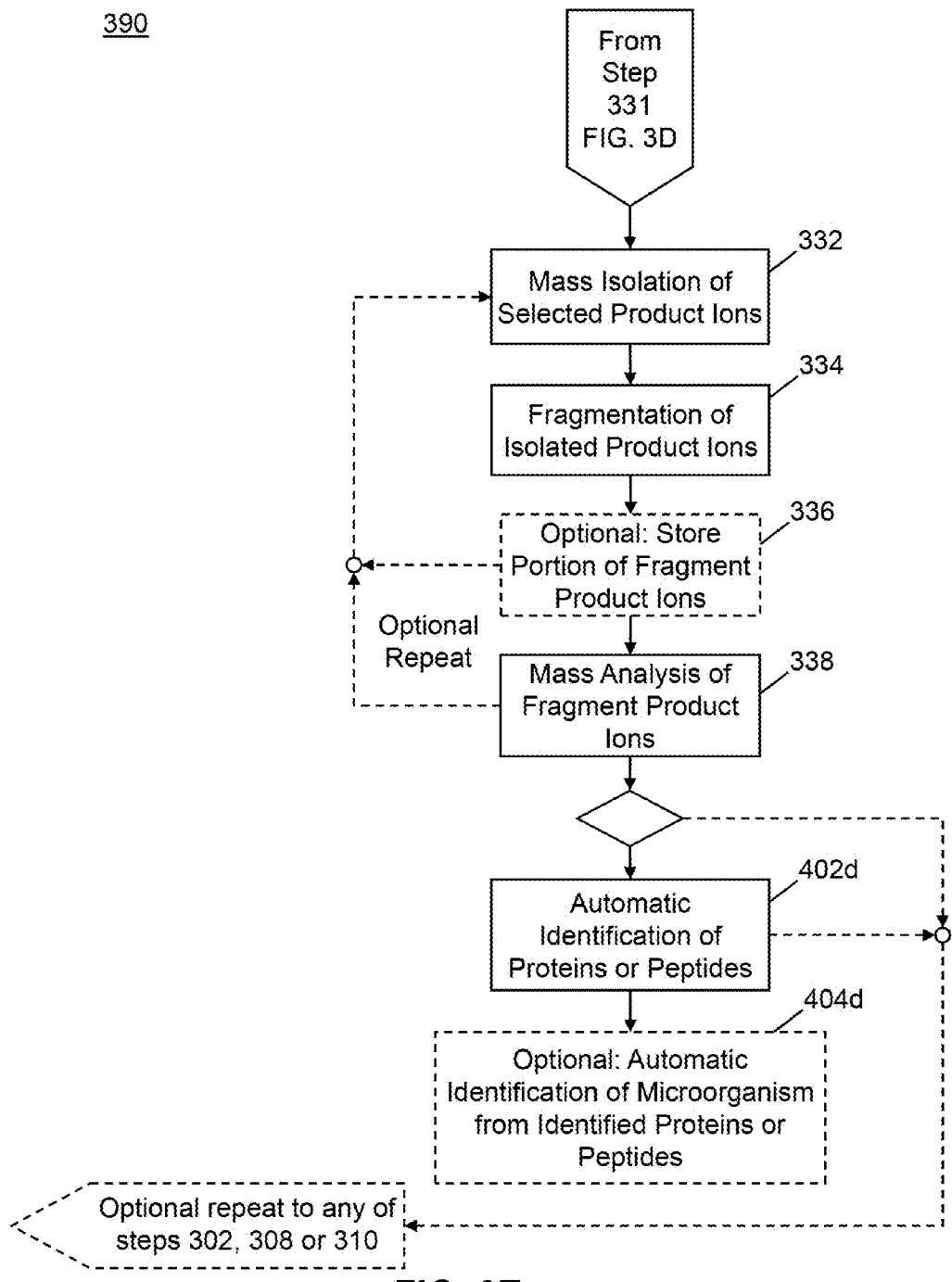

FIGS. 3D-3E illustrate, in flow diagram form, another method, method 390, in accordance with the present teachings. The steps 302-331 of the method 390 are shown in FIG. 3D and are identical to the previously-discussed similarly-numbered steps of the method 380 (FIG. 3C); thus, these steps are not re-described here. Instead of proceeding to the identification step 402d directly from step 330 (as in the method 380 of FIG. 3C), execution of the method 390 (FIGS. 3D-3E) proceeds from step 330 to a mass selection and isolation step 332. In step 332, a subset of the PTR product ions—generated by one or more applications of the PTR procedure—are isolated according to selected m/z ratios. Decisions regarding the specific m/z ratios to be isolated during this step may be automatically performed based on the mass spectrometric results obtained in step 330 or, with respect to an optional subsequent mass isolation and fragmentation (see optional repeat branch of FIG. 3E), based on the results of a mass analysis of the fragment ions themselves (step 338). The steps 332-338 illustrated in FIG. 3E represent an ion fragmentation procedure which may be iterated (see optional repeat branch) so as to produce multiple generations of fragmentation product ions. These steps 332-338 are similar to the steps 318-322 of the method 370 illustrated in FIG. 3B and are thus not discussed in detail.

After execution of the fragmentation and mass analysis steps, the peptide identification step 402d of the method 390 (FIG. 3E) is executed. Whereas the identification step 402a of the method 300 (FIG. 3A) makes use only of the m/z ratios (or molecular weights) of ion species comprising protonated or multiply-protonated analyte molecules, the identification step 402d of the method 390 also takes into account the m/z ratios of the fragments—possibly of multiple generations—of these ion species. Thus, in the case of complex mixtures of proteins or polypeptides, a greater confidence may be associated with the results of the identifications made using the method 390. Control of the experiments may be performed in real time according to some embodiments by making use of real-time data deconvolution as noted above. The identification of a small number of (3-10) of proteins species in step 402d will generally be sufficient to uniquely identify a microorganism species in step 404d.

Figure 3F:
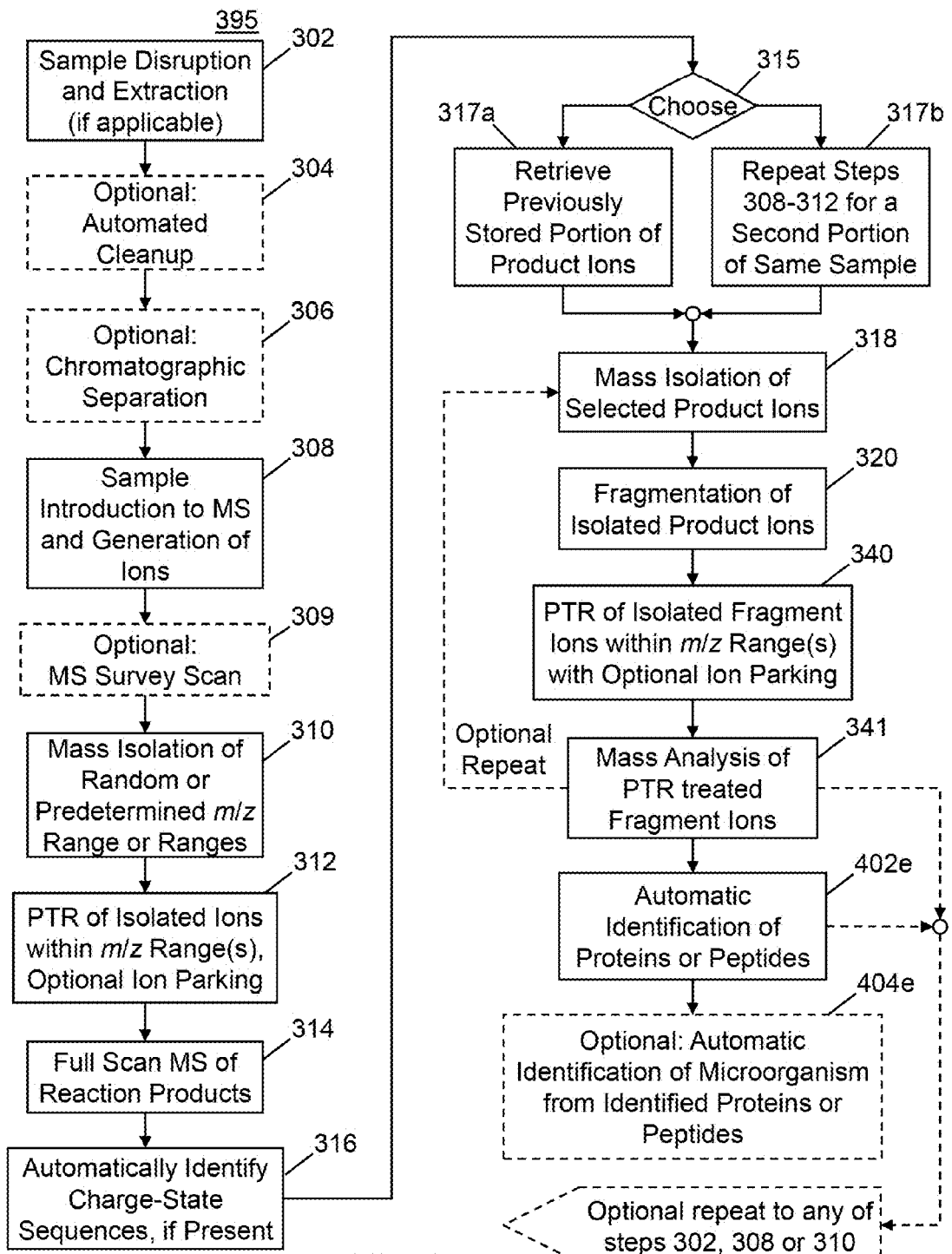
FIG. 3F is a flow diagram of still yet another alternative method in accordance with the present teachings.

FIG. 3F diagrammatically illustrates, in flow diagram form, another method, method 395, in accordance with the present teachings. Most of the steps in the method 395 (FIG. 3F) are similar to similarly numbered steps in the method 370 (FIG. 3B) and these steps are not re-described in detail. Similarly to the method 370, the method 395 includes a step (step 312) of subjecting original precursor ions to PTR charge reduction followed by steps (steps 318 and 320) of isolating selected PTR product ion species and subjecting the isolated ion species to fragmentation so as to form fragment product ion species. The method 395 differs from method 370 through the provision of an additional step, step 340, of subjecting the fragment ions to PTR charge reduction. Since the various PTR product ion species generated from the original precursor ions may be multiply-charged and may be distributed among species with various degrees of protonation, the fragment ions formed from them may themselves be distributed among multiple protonation states. The PTR charge reduction of the fragment ion species in step 340 can simplify the charge state distributions of the fragment ions prior to their mass analysis in step 341. Optionally, any of the PTR steps (step 312 and step 340) may employ ion parking. An optional repeat from step 341 back to step 318 so as to repeat the steps 318-341 may be performed for the purpose of choosing a second, different ion species of the PTR reaction products (generated and possibly stored in step 312) for fragmentation, based on the automatic identification of charge state sequences previously performed in step 316. As previously discussed with respect to the method 370 (FIG. 3B), the second, different ion species may belong to a set of lines of a second charge state envelope that is different from the charge state envelope to which a prior isolated and fragmented ion species belongs (see also FIG. 12C). The novel "Top P Unique Analyte-Specific Clusters" workflow described in the appendix is specifically adapted to recognize such clusters corresponding to different respective potential analyte molecules. In this way, fragment information about different potential analytes is obtained during each iteration of the optional loop comprising steps 318-341 of the method 395.

Example A

Figure 4A:
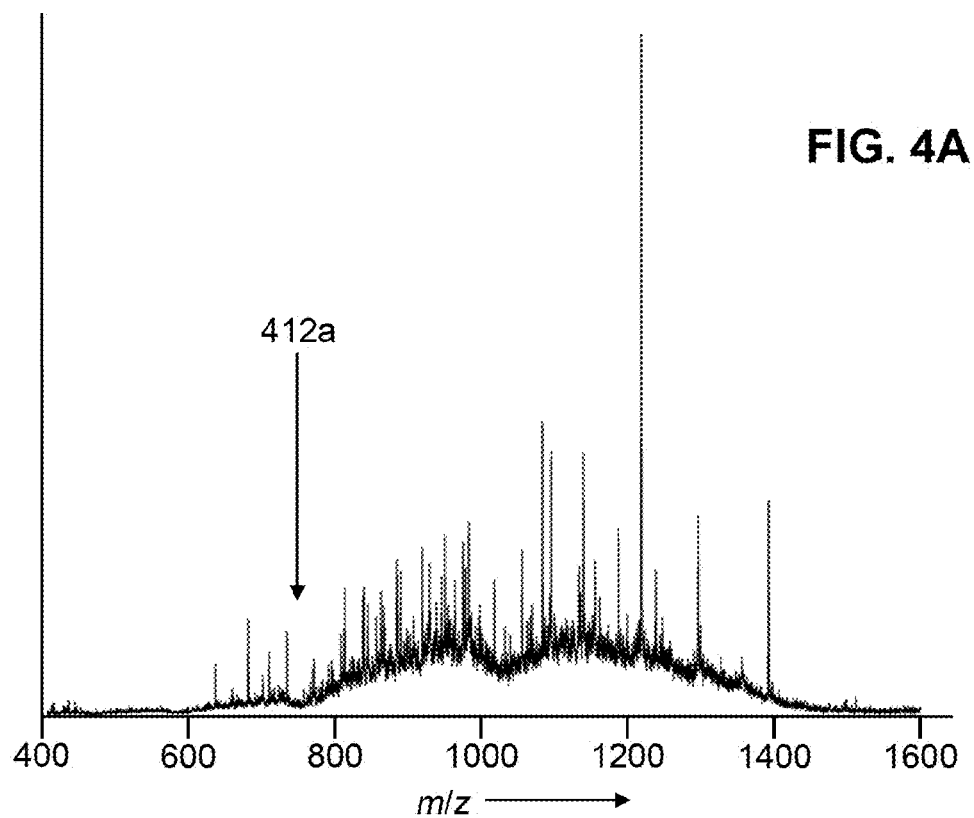
FIG. 4A is an ESI mass spectrum via direct infusion of a typical $E.\ coli$ extract.
Figure 4B:
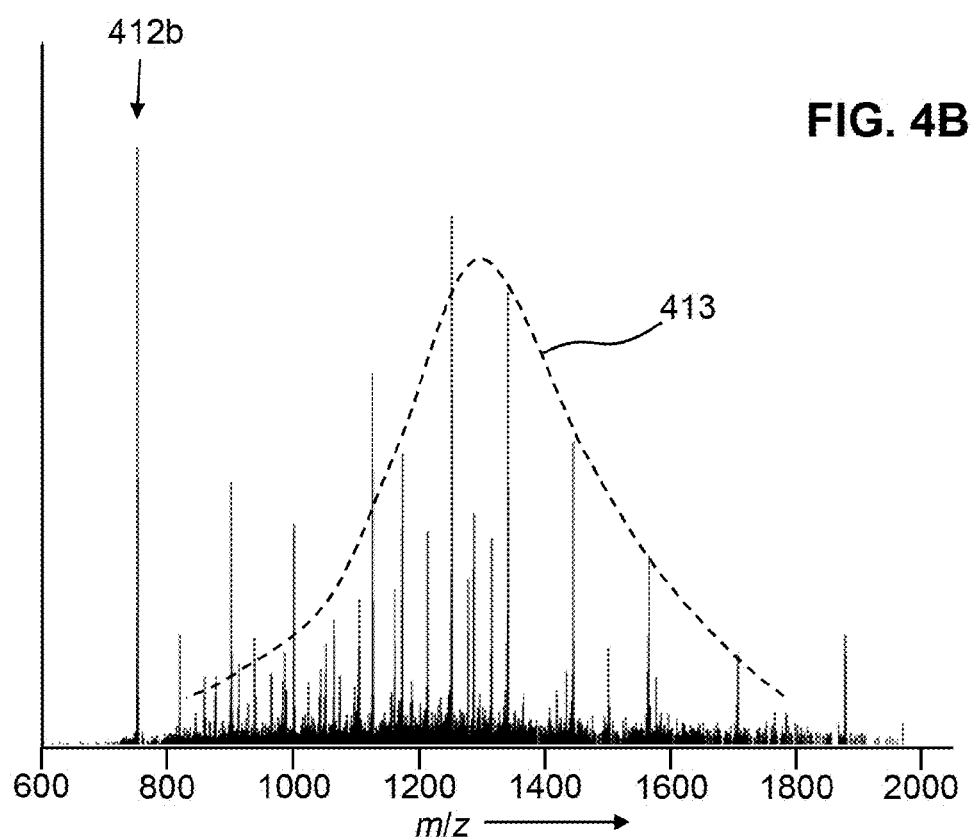
FIG. 4B is a PTR product-ion mass spectrum generated by isolating ions of the $E.\ coli$ extract of FIG. 4A within a 2 Th mass window centered at m/z=750 Th and reacting the isolated ions with PTR reagent anions.

FIGS. 4A and 4B provide an example of mass spectroscopic signal enhancement provided by a single PTR reaction step (e.g., as in the method 300 shown in FIG. 3A). In a first application (FIGS. 4A, 4B), an extract from the pathogen E. coli was analyzed via direct infusion; the mass spectrum of the first-generation electrospray-generated ions is shown in FIG. 4A. As expected, there are many proteins present that overlap at various m/z values leading to the presence of a broad spectral region between approximately m/z=780 and m/z=1420 within which many ions are detected but with very little usable information in terms of discernible protein charge state distributions. Next, an m/z "window" of the first-generation ions of width 2 Th and centered at m/z=750 was isolated and the resulting isolated ion population was subjected to PTR reaction. The m/z position 412a shown in FIG. 4A indicates the center position of the isolation window.

FIG. 4B shows a mass spectrum of the PTR reaction products of precursor ions of the E. coli extract. The PTR reactions were carried out with reagent anions derived from 3 ppm of sulfur hexafluoride ($SF_6$) in a nitrogen gas stream delivered to a glow discharge reagent ion source contained within the ion optics of a mass spectrometer of the same general configuration as illustrated in FIG. 2. As with most PTR product-ion spectra, the mass spectrum shown in FIG. 4B exhibits a relatively intense isolated peak at the position (indicated as position 412b) of the original first-generation-ion isolation window. Such peaks at the position of the isolation window generally indicate the presence of residual singly-charged first-generation ions—generally not of interest—that fortuitously occur at the position of the isolation. Other peaks in the spectrum of FIG. 4B represent product ions generated from the PTR reaction. These product ions generally comprise overlapping sets of related ions, each set corresponding to ions comprising a distribution of charge states from an original multiply-charged precursor ion within the original isolation window. One such potential charge-state distribution pattern is approximately indicated by the envelope 413. The results shown in FIGS. 4A and 4B show that the PTR reaction process generally significantly simplifies the spectrum and reduces background interference. Nonetheless, since many protein-derived or peptide-derived precursor ions may be present in the original isolation window, the charge-state distribution patterns may overlap. Mathematical decomposition (sometimes referred to as "deconvolution") may be required to recognize the individual patterns.

Example B

Figure 5A:
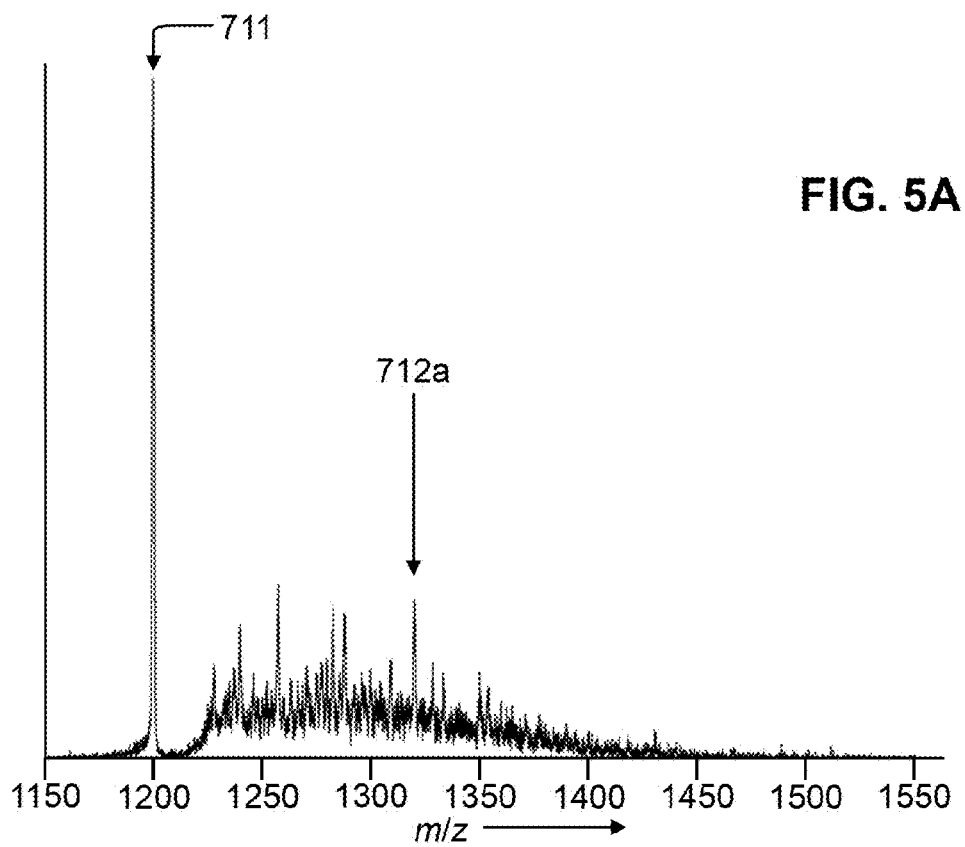
FIG. 5A is a mass spectrum of first-generation PTR product ions generated by isolating ions of an $E.\ coli$ extract within a mass window of width 5 Th centered at 1200 Th and reacting the isolated ions with PTR reagent anions.
Figure 5B:
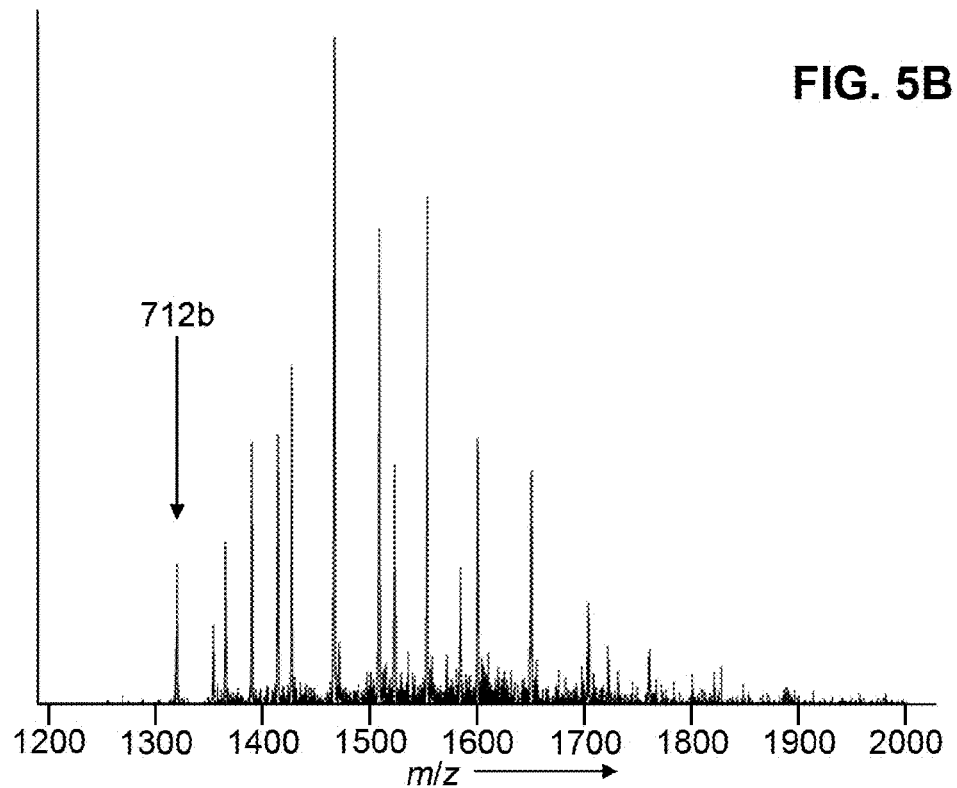
FIG. 5B is a mass spectrum of second-generation PTR product ions generated by isolating ions of the first-generation PTR product ions of FIG. 5A within a mass window of width 5 Th centered at 1320 Th and reacting the isolated first-generation product ions with PTR reagent anions a second time.

FIGS. 5A and 5B illustrate an example of analysis of an E. Coli extract that is performed by a procedure that includes two stages of PTR reaction (for example, see steps 327, 328, 329 and 330 of method 380 in FIG. 3C). FIG. 5A illustrates a PTR product ion spectrum generated isolated first-generation precursor ions from within a 5 Th mass window centered at m/z=1200, indicated by position 711 in FIG. 5A. In this instance, the initial PTR spectrum does not include peaks that are sufficiently well resolved to enable identification of any proteins in the sample. Therefore, a subset of the first-generation PTR product ions were isolated for a second stage of PTR from within a 5 Th mass window centered at m/z=1320, indicated by position 712a in FIG. 5A and position 712b in FIG. 5B. The second-generation PTR product ions, which occur at m/z ratios greater than 1320 in FIG. 5B show clear charge-state distribution patterns that may be successfully used for identification of proteins in the sample.

Figure 6A:
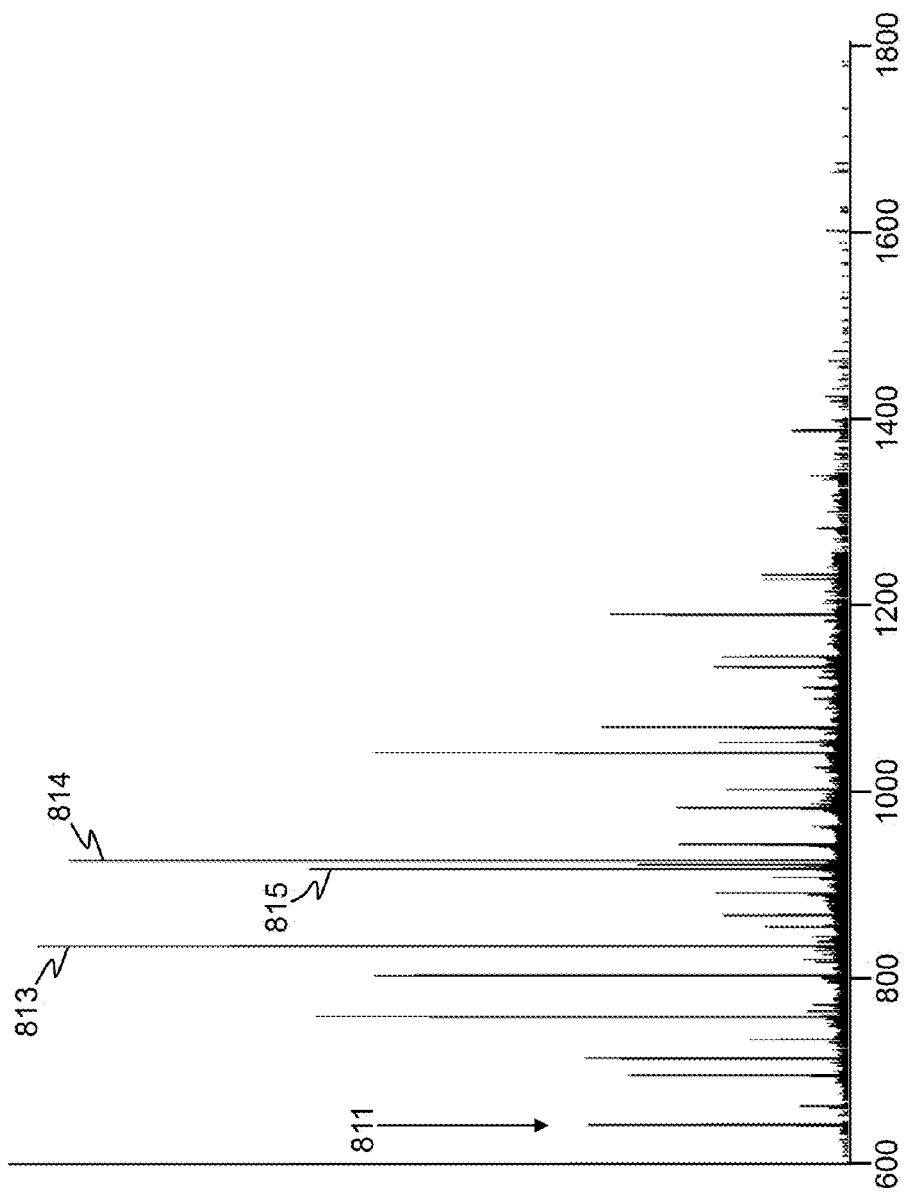
FIG. 6A is a mass spectrum of PTR product ions generated by isolating ions of an $E.\ coli$ extract within a mass window of width 5 Th centered at 640 Th and reacting the isolated ions with PTR reagent anions.
Figure 6B:
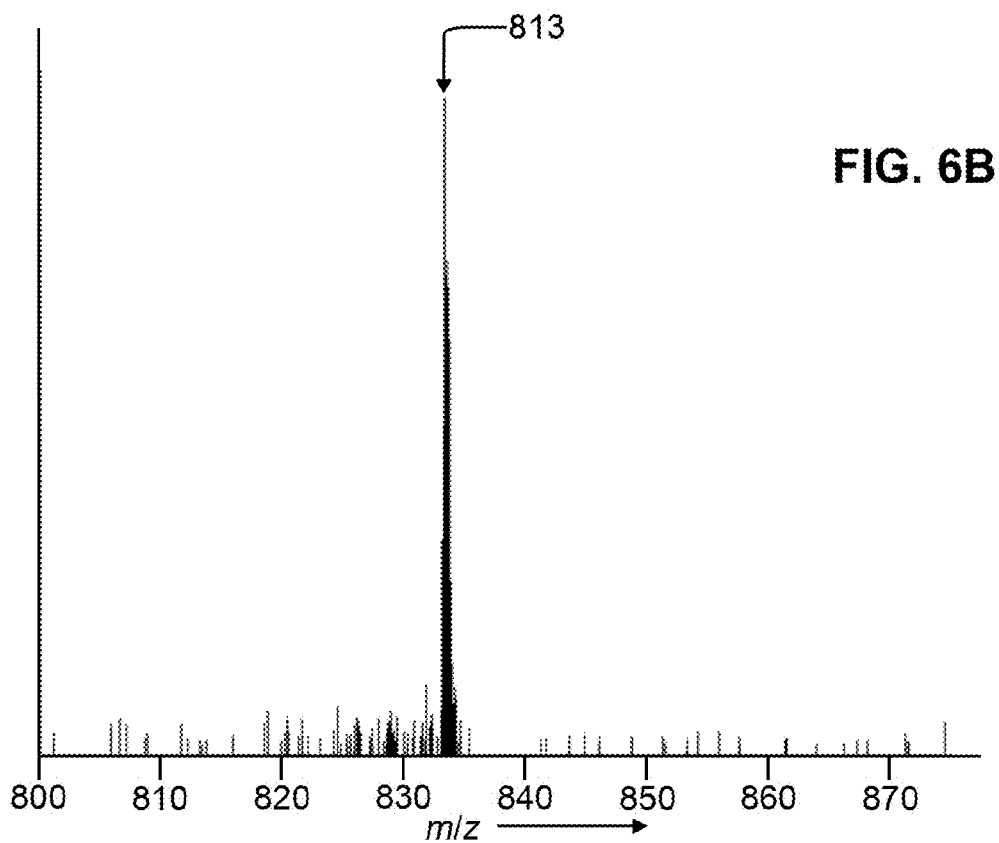
FIG. 6B is a mass spectrum of an isolated PTR product ion species selected from the product ion assemblage of FIG. 6A and having an m/z ratio of 833 Th.
Figure 6C:
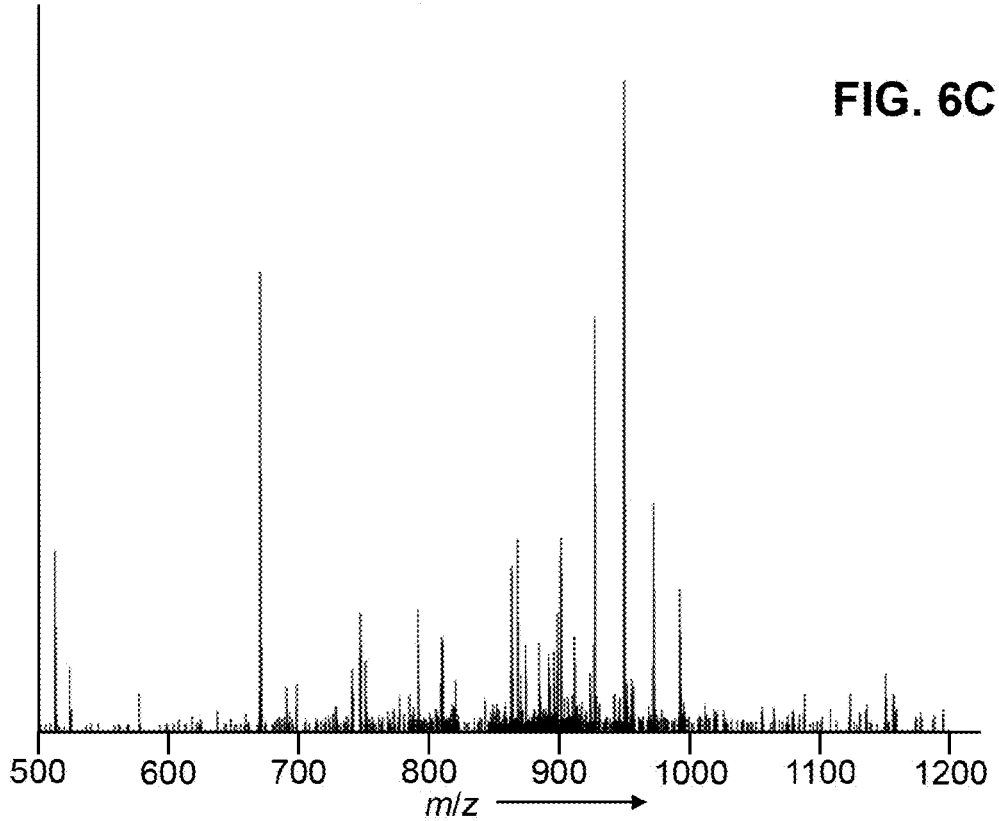
FIG. 6C is a mass spectrum of second-generation product ions generated by collision-induced dissociation (CID) of the isolated PTR product ion species of FIG. 6B.
Figure 6D:
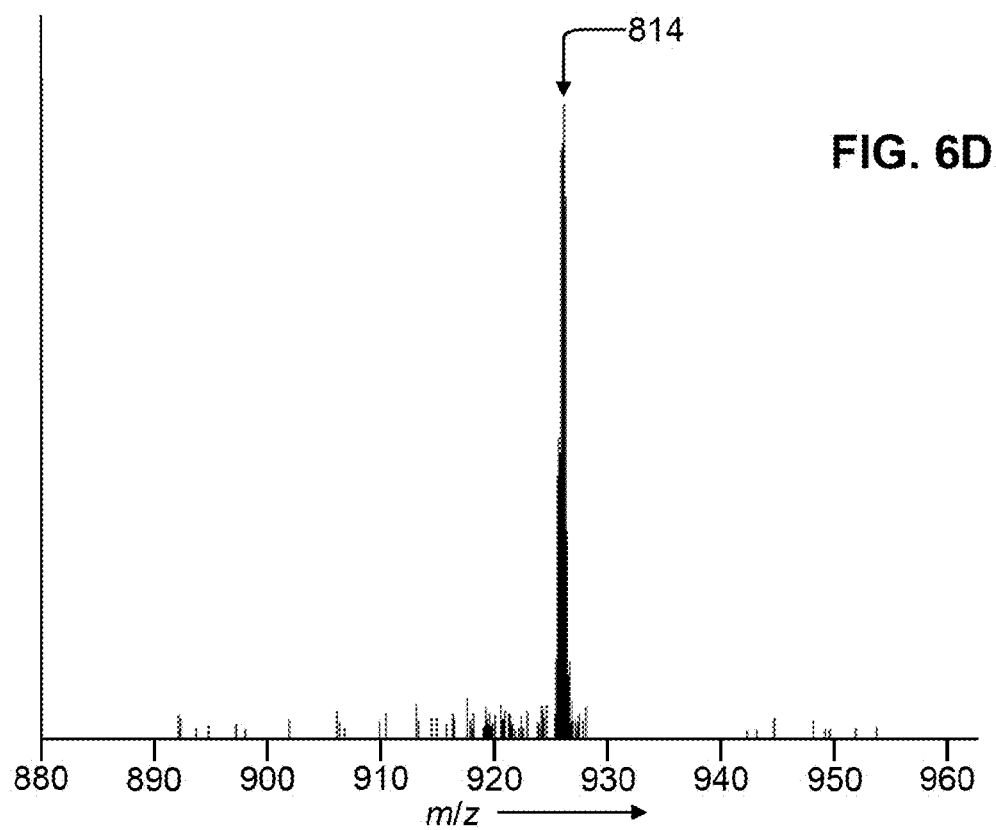
FIG. 6D is a mass spectrum of an isolated PTR product ion species selected from the product ion assemblage of FIG. 6A and having an m/z ratio of 926 Th.
Figure 6E:
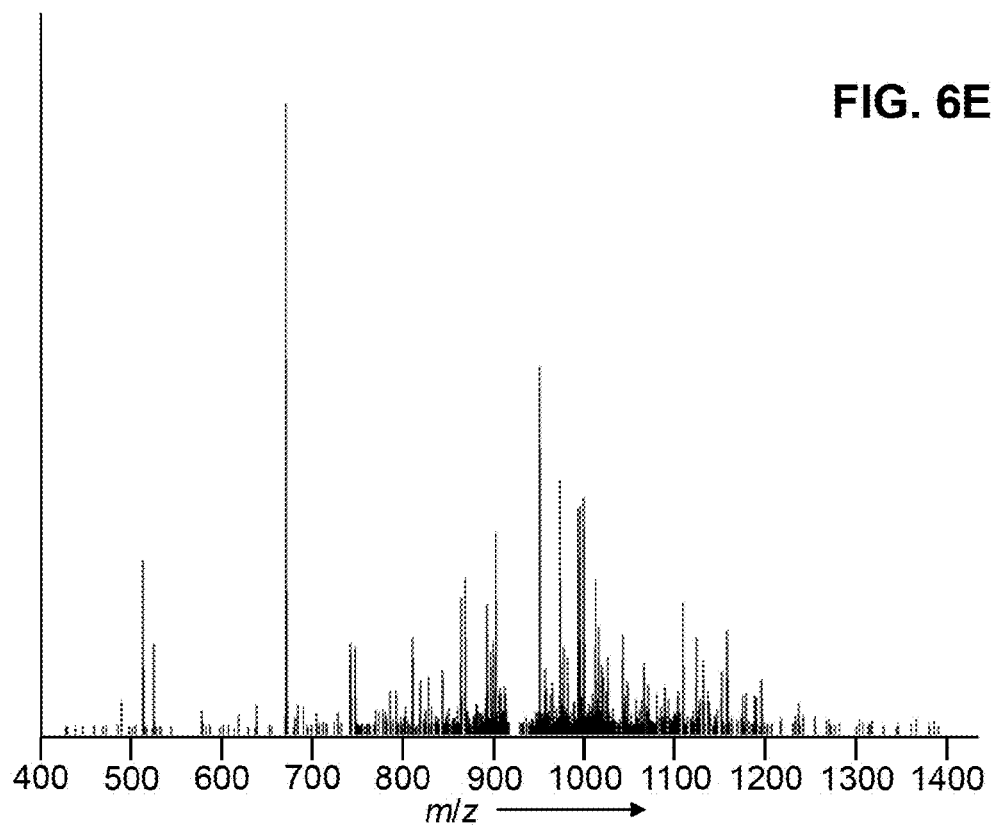
FIG. 6E is a mass spectrum of second-generation product ions generated by collision-induced dissociation of the isolated PTR product ion species of FIG. 6D.
Figure 6F:
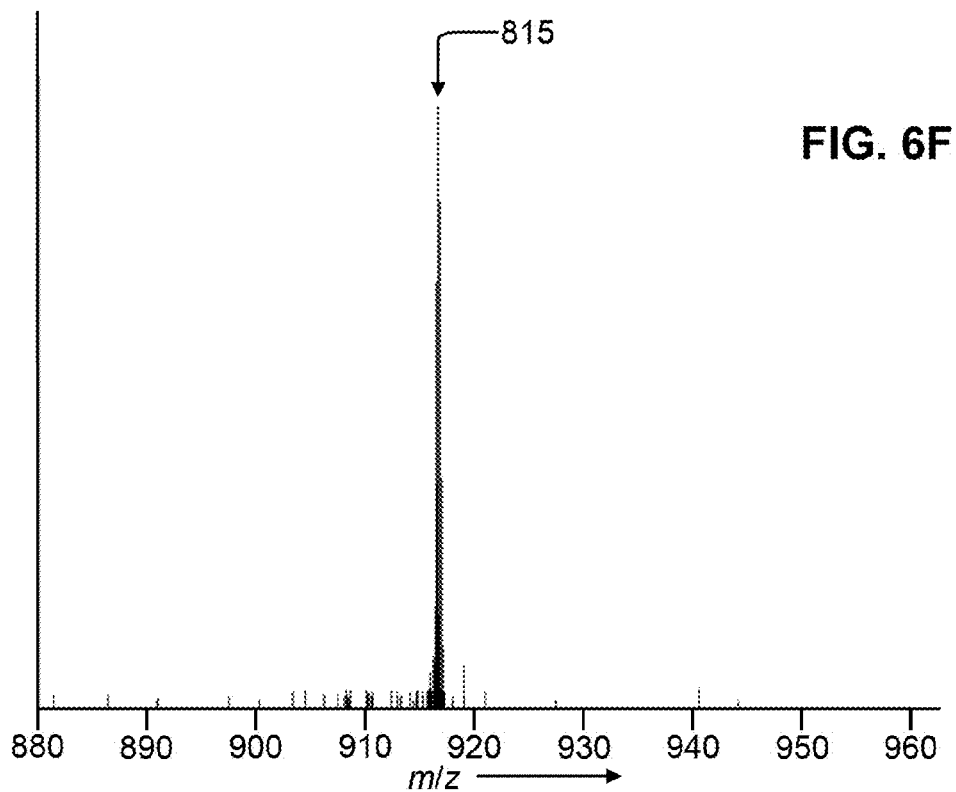
FIG. 6F is a mass spectrum of an isolated PTR product ion species selected from the product ion assemblage of FIG. 6A and having an m/z ratio of 917 Th.
Figure 6G:
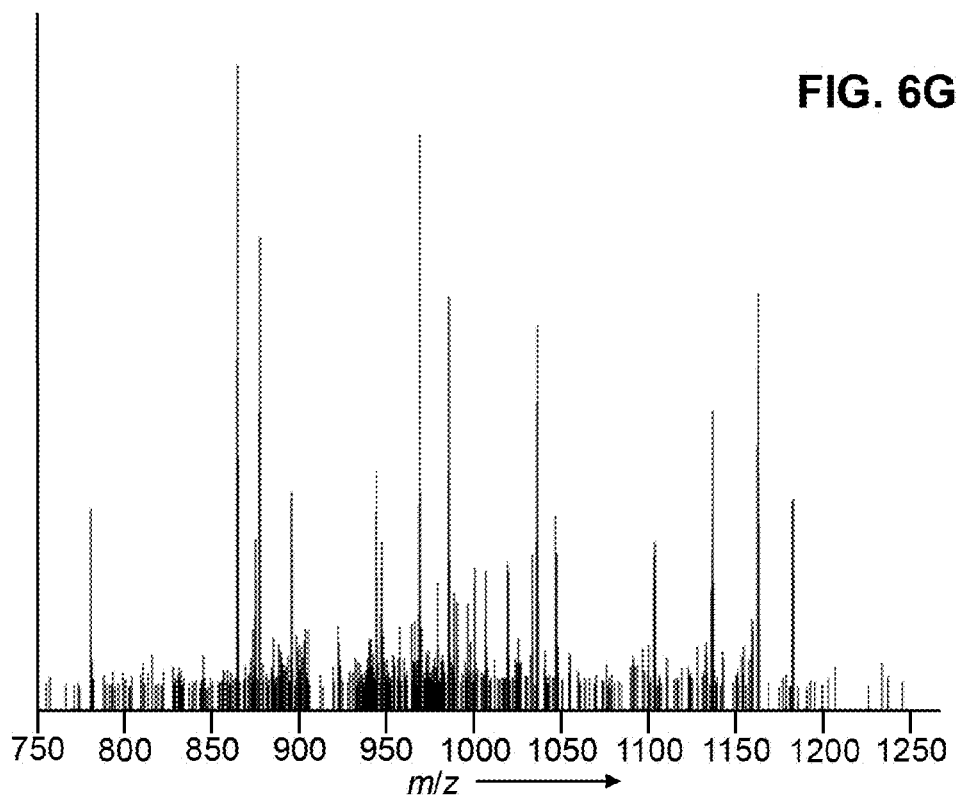
FIG. 6G is a mass spectrum of second-generation product ions generated by collision-induced dissociation of the isolated PTR product ion species of FIG. 6F.

FIGS. 6A-6G illustrate an example of analysis of an *E. coli* extract that is performed by a procedure that includes a first stage of product ion formation by PTR reaction followed by subsequent stages of CID of the PTR reaction product ions (for example, see steps 312 through 322 method 370 in FIG. 3B). FIG. 6A illustrates a PTR product ion spectrum generated isolated first-generation precursor ions from within a 5 Th mass window centered at m/z=640, indicated by position 811 in FIG. 6A. The PTR product ions occur at m/z ratios greater than that indicated by position 811 in FIG. 6A. The three most intense PTR product ions, located at m/z ratios of 833, 926 and 917 and indicated by mass spectral peaks 813, 814 and 815, respectively, in FIG. 6A, were then individually isolated and separately subjected to collision-induced dissociation so as to produce three sets of second-generation product ions. FIGS. 6B and 6C respectively depict the isolated PTR product ion at m/z=833 and the second generation product ions (fragment ions) generated by CID of the isolated PTR product ion. Likewise, FIGS. 6D and 6E respectively depict the isolated PTR product ion at m/z=926 and the second generation product ions generated by CID of the isolated PTR product ion at m/z=926. Likewise, FIGS. 6F and 6G respectively depict the isolated PTR product ion at m/z=917 and the second generation product ions generated by CID of the isolated PTR product ion at m/z=917.

Example C

As should be evident from the previous discussions, positive ion electrospray ionization of any protein or polypeptide molecule will produce a plurality of ions comprising different respective charge states (i.e., number of charges) as a result of different degrees of protonation of the original molecule. Charge states of +50 or more or possible and each charge state will be represented by multiple mass spectral lines representing different degrees of natural isotopic substitution. A further complication arises from the fact that for most natural biological samples, numerous different proteins of polypeptide molecules may be represented in a mass spectrum. A yet further complication arises from the fact that many other molecules—not necessarily of interest—may be present in a sample.

In many basic-research-oriented studies, the above-noted complicating factors of multiple analytes and multiple interfering species may be partially or wholly resolved by performing chromatic separation prior to introducing each separated compound individually into a mass spectrometer. However, clinical analyses may often be performed under tight time constraints that do not allow for traditional time-consuming chromatographic separation. The clinical time constraints may only allow for an incomplete or partial separation using either solid-phase extraction (SPE), size-exclusion chromatography, or the method of Fast Partial Chromatographic Separation (FPCS) described above. Thus, when such partial separation procedures are employed, the mass spectral signature of any particular protein or polypeptide may be spread out over a wide mass-to-charge ratio and may be complexly overlapped with the mass spectral signatures of other compounds. Since the available charge, as provided by an electrospray apparatus, will be spread out over many different types of ions, most of the observed mass spectral lines will coexist with and possibly be hidden within a general densely populated and low-intensity or ill-defined spectral "background" indicated schematically by spectral envelope 902 in FIGS. 7A-7B.

The inventors have realized that the mass spectral signature of any particular protein, polypeptide or other biologically relevant high-molecular-weight analyte may be hypothetically amplified by simultaneously isolating multiple charge states of the same original molecule and then reacting the assemblage of multiple charge states with PTR reagent ions so as to simultaneously reduce the assemblage to a small number of charge states distributed over a few charge-state values, these charge-state values being reduced relative to the original charge states. This concept is illustrated by the vertical boxes 904a-904g shown overlaid over the general charge-state envelope 902 in FIG. 7A. Each such vertical box represents a particular precursor ion species and represents a small range of m/z values chosen to correspond to a particular charge state (and possibly including a few isotopic variants) of a particular analyte. Hypothetically, if all ions outside of the ranges corresponding to the vertical boxes could be excluded and only the ions from within the indicated ranges mixed together, then subsequent PTR would essentially provide a summation of the signals from the various original plurality of charge states. The use of such multi-species isolation of a plurality of precursor ion species can increase the sensitivity of the analysis up to N-fold, where N is the number of m/z ranges selected and simultaneously isolated.

Such multiple-species isolation is fairly easy to achieve when isolation is performed in a linear ion trap (such as the low-pressure linear trap cell 217b illustrated in FIG. 2), because resonance-excitation waveforms, which are used to eject unwanted ions, may be constructed with multiple notches. Each such notch corresponds to a different respective m/z window within which ions will not be ejected (and thus isolated). Thus, the co-isolating of a plurality of electrospray-generated (first-generation) precursor ion species may be performed, in some embodiments, by simultaneously isolating all of the plurality of precursor ion species. One way of doing this is by applying a broadband resonance ejection frequency waveform to an ion trap into which ions received from an electrospray source have been introduced, wherein the waveform comprises multiple summed sinusoidal frequency components, wherein included frequency components corresponding to the m/z ranges of ions that one desires to eject from the trap and excluded frequency components correspond to the m/z range of ions that one desires to retain within the trap. In this procedure, the omitted frequencies define one or more frequency notches in the ejection frequency waveform. The frequency components may be calculated by first choosing a desired multi-notch waveform and then calculating an inverse Fourier Transform of the desired waveform.

Alternatively, the co-isolating of the plurality of precursor ion species may be performed by isolating individual precursor ion species in a conventional sense, one ion species at a time using a respective single-notch waveform applied to an ion trap. The individually isolated precursor ion species may be transferred, one at a time, to an ion storage component (such as the multipole ion guide 214 illustrated in FIG. 2) in which the various selected and isolated ion species are accumulated over time. As a yet-further alternative, the co-isolating of the plurality of precursor ion species may be performed by passing a plurality of ions received from an electrospray source through a quadrupole mass filter while the bandpass of the quadrupole mass filter is sequentially tuned to preferentially transmit, in turn, each m/z range corresponding to a particular precursor ion species. The filtered ions that pass through the quadrupole mass filter are then passed into an ion storage component that accumulates the ions from all the preferentially transmitted m/z ranges. For example, in the mass spectrometer 150a illustrated in FIG. 2, the quadrupole mass filter 208 may perform the sequence of filtering steps and the ions of each transmitted m/z range may be transmitted into and accumulated within the multipole ion guide 214. The accumulated precursor ion species may then be transferred back to the low-pressure cell 217b for PTR reaction.

The above-described procedure employing simultaneous multi-species isolation assumes that appropriate isolation ranges 904a-904g a priori known. Such knowledge about the correct isolation ranges to employ may be available in certain instances of targeted analysis, when the identity of (and other information pertaining to) an analyte that is to be searched for is already known and the purpose of the analysis is to determine the presence or absence of the analyte or to determine the quantity or concentration of the analyte. However, the above assumption may be invalid in the case of survey analyses, in which the identities of analytes may not be known in advance. In such latter cases, an initial random survey may be performed by isolating a random mass range 903 of the first-generation ions, as schematically depicted in FIG. 7B, and then reacting the isolated ions with a PTR reagent anion. As previously illustrated in FIGS. 4A and 4B, such a procedure can provide resolved, interpretable mass spectral lines relating to charge state distributions of one or more analytes. In many instances, a set of related lines may be recognized with by the mutual consistency of their m/z values with Eq. 1 for a certain sequence of consecutive integers, z. The degree of consistency of the line positions may be performed automatically, by computer analysis, such that overlapping sets of such related lines may be mathematically decomposed and recognized.

As an example of the above type of analysis, mathematical decomposition of the PTR product ion lines generated by isolation and reaction of precursor ions within m/z range 903 may lead to recognition of two overlapping sets of lines, depicted by envelope 905 and envelope 906, as illustrated in FIG. 7C. With the information provided by this initial survey procedure, an appropriate and consistent set of m/z values may be chosen, which may be employed in a subsequent simultaneous multi-species isolation and reaction procedure. For example, the m/z values of certain resolved instances of the lines under envelope 905 may be chosen, perhaps automatically. Subsequent multi-species isolation and PTR reaction of precursor ions corresponding to these chosen m/z values will then provide an amplified spectrum that may be employed to determine a quantity or concentration of the particular molecule represented by the envelope 905. This procedure may later be repeated using the associated with envelope 906 so as to determine a quantity or concentration of another molecule. The determined quantities or concentrations may not be accurate, in an absolute sense, but the ratios of the determined quantities or concentrations may provide useful information relating to relative quantities or concentrations. This entire procedure outlined above may be repeated multiple times using different randomly chosen m/z ranges 903, thereby providing determinations of relative quantities or concentrations of several compounds. As stated previously, control of such experiments can be accomplished in a data-dependent fashion utilizing the results of real-time spectral deconvolution.

Figure 8:
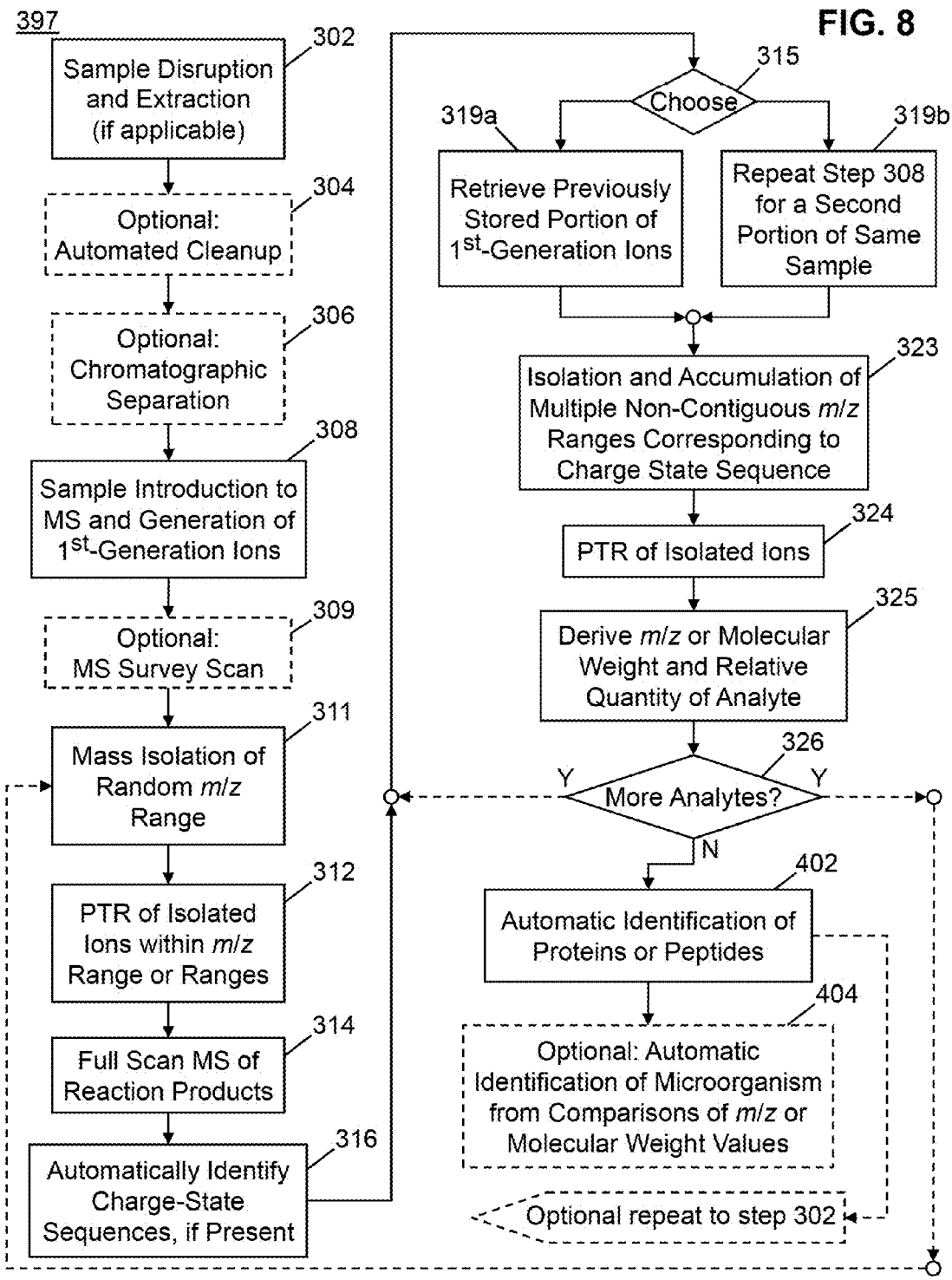
FIG. 8 is a flow diagram of a method, in accordance with the present teachings, of improved-efficiency PTR conversion of ions of a selected analyte to an assemblage of PTR product ions.

FIG. 8 provides a general flow diagram of an exemplary method, method 397, of survey analysis using the above-outlined PTR signal amplification by reaction of PTR reagent ions with first-generation ions from multiple non-contiguous m/z ranges. Steps 302, 304, 306, 308, 309, 312, 314, 316, 402 and 404 of the method 397 are identical to the similarly numbered steps of the method 300 illustrated in FIG. 3A and are thus not re-described here. Also, the new step 311 is similar to the previously described step 310 of method 300, except that step 311 refers only to mass isolation of a random m/z range (such as the range 903 depicted in FIG. 7C) of first-generation ions, instead of to a "random or predetermined m/z range or ranges" as described for the prior method 300. After the initial survey PTR reaction (step 312) and identification of charge-state sequences (step 316), the latter of which is preferably performed by the computational methods described in the appendix to this document, the step 323 is executed, in which multiple non-contiguous m/z ranges of the first-generation ions are isolated and accumulated, wherein the non-contiguous m/z ranges correspond to an identified charge state sequence. The first-generation ions may be obtained from a previously stored batch of such ions (prior step 319a) or, alternatively (prior step 319b), the sample introduction and electrospray ion generation step may need to be repeated.

After the isolation and accumulation of multiple non-contiguous m/z ranges of the first-generation ions (step 323), the accumulated ions are reacted with PTR reagent ions (step 324). The resulting amplified spectra will generally be of high quality thereby facilitating the derivation (step 325) of, for example, an accurate molecular weight of the molecule corresponding the multiple non-contiguous m/z ranges or an accurate quantity, concentration, or relative abundance of such molecule. If an immediately prior execution of step 316 identified more than one set of related m/z ratios, then step 319a or 319b and steps 323-325 may be executed again (following the leftmost "Y" branch of step 326) using a new set of non-contiguous m/z ranges that correspond to a different identified charge state sequence. If a search for possible additional analytes is to be continued, then execution may return to step 311 (following the rightmost "Y" branch of step 326) at which a different random m/z range is chosen.

Example D

According to another method for reduction of sample complexity utilizing proton transfer reactions in accordance with the present teachings, mass spectrometric analysis employing PTR can be coupled directly with chromatography in order to simplify and detect additional proteins that would otherwise be missed. In this embodiment, a full scan mass spectrum is taken and the protein molecular weights are calculated using a real-time deconvolution program. Next, an isolation window is chosen of a defined width and the subset of m/z values in the window are subjected to PTR reactions.

Figure 9B:
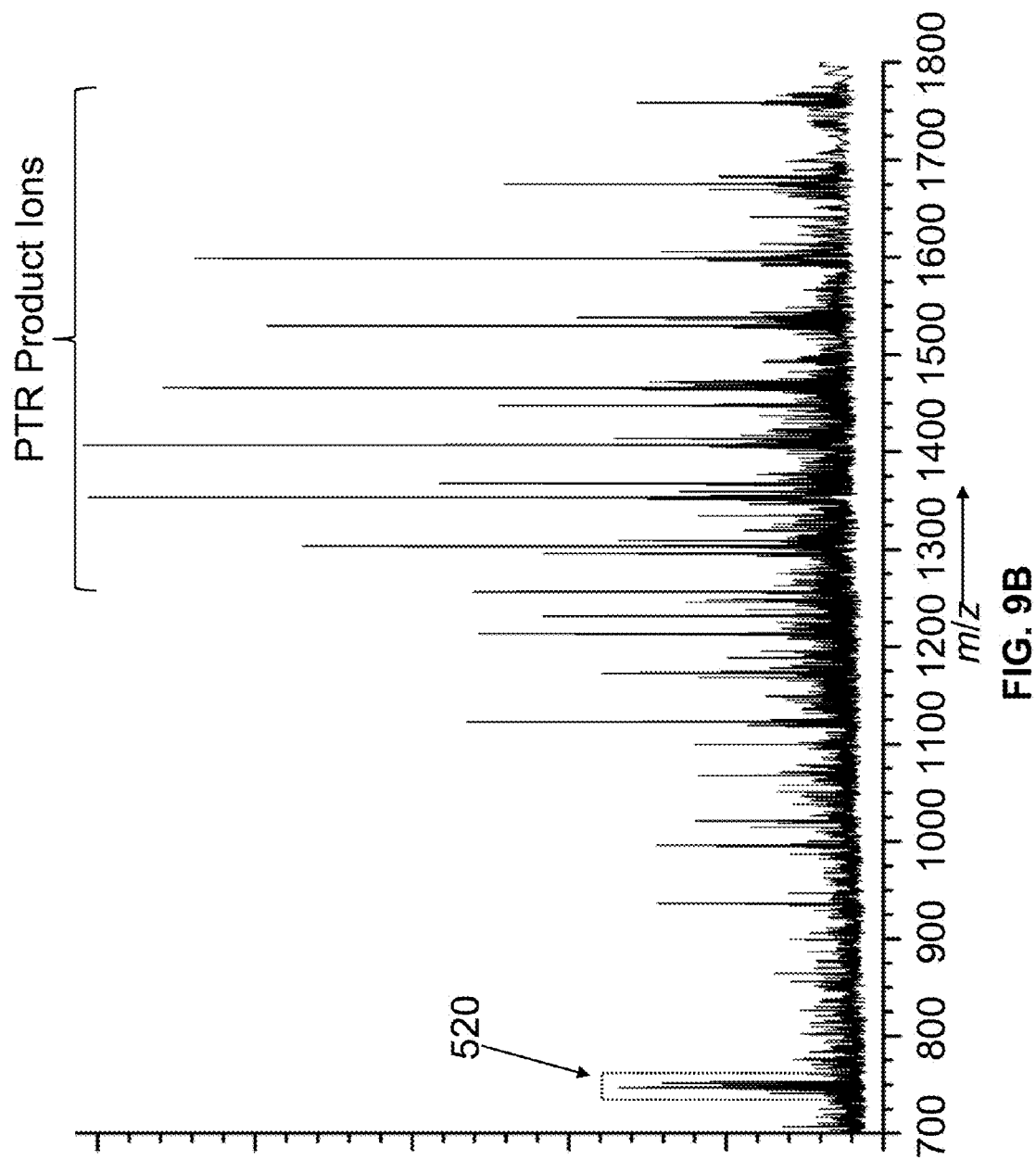
FIG. 9B is a PTR product ion spectrum generated by reacting sulfur hexafluoride for 10 ms with an isolated population of ions of the sample of FIG. 9A within a 10 Th wide isolation window centered at 750 Th.

For example, FIG. 9A shows a full scan mass spectrum of first-generation ions generated from eluate at a retention time of 10 min. and 30 s. during the course of a ten-minute gradient reverse-phase liquid chromatography separation of an E. coli extract. As indicated by the braces in FIG. 9A, this full-scan mass spectrum exhibits the distinct spectral signatures of two proteins having approximate molecular weights of 35.1 and 31.1 kDa respectively. For the next step, a population of ions having m/z values within an m/z isolation window 510 of 10 Th width and centered at 750 Th were isolated. The isolated ion population was then subjected to PTR reactions with the anionic reagent sulfur hexafluoride for 10 ms. The resulting product ion mass spectrum, shown in FIG. 9B, exhibits the mass spectral signatures of two additional proteins not seen in the full-scan mass spectrum having molecular weights of 11220.07 Da and 24599.56 Da. In addition, the 35.1 kDa protein component previously observed in the full-scan mass spectrum also exhibits a spectral signature in the PTR product ion spectrum which includes a line, outlined in box 520, corresponding to a +47 charge state at a nominal m/z value of 749. The line at 749 Th represents charge reduction of even-more-highly-charged states of the 35.1 kDa protein. The proteins observed at 11.2 and 24.6 kDa would not otherwise be identified in the absence of the PTR step in this example of a reverse-phase chromatographic run as a result of complex spectral overlap and interfering noise from an abundance of singly-charged background ions.

Figure 10A:
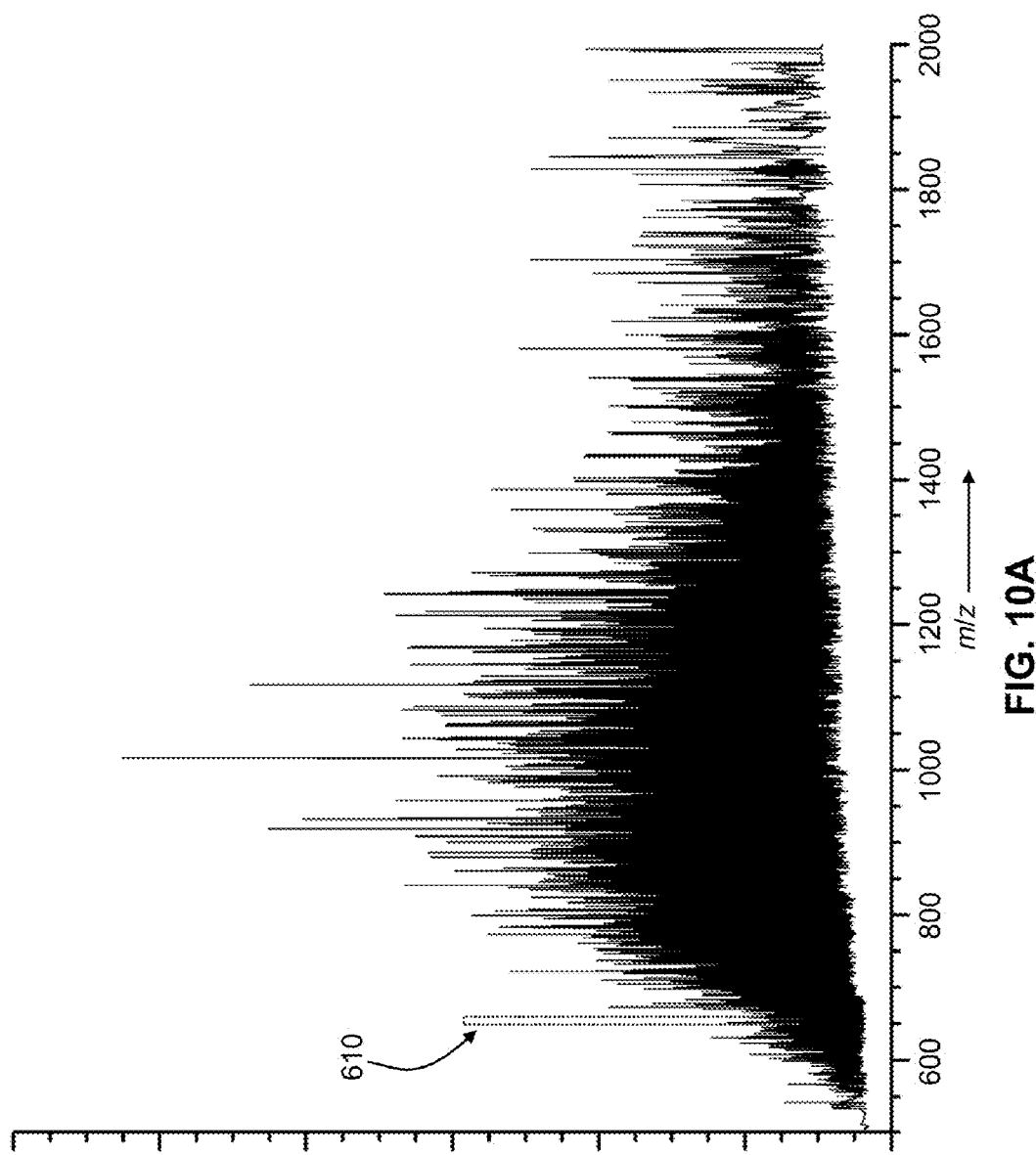
FIG. 10A is a full scan mass spectrum of first-generation ions generated from eluate at a retention time of 42 min. and 30 s. during the course of a sixty-minute gradient reverse-phase liquid chromatography separation of an *E. coli* extract.
Figure 10B:
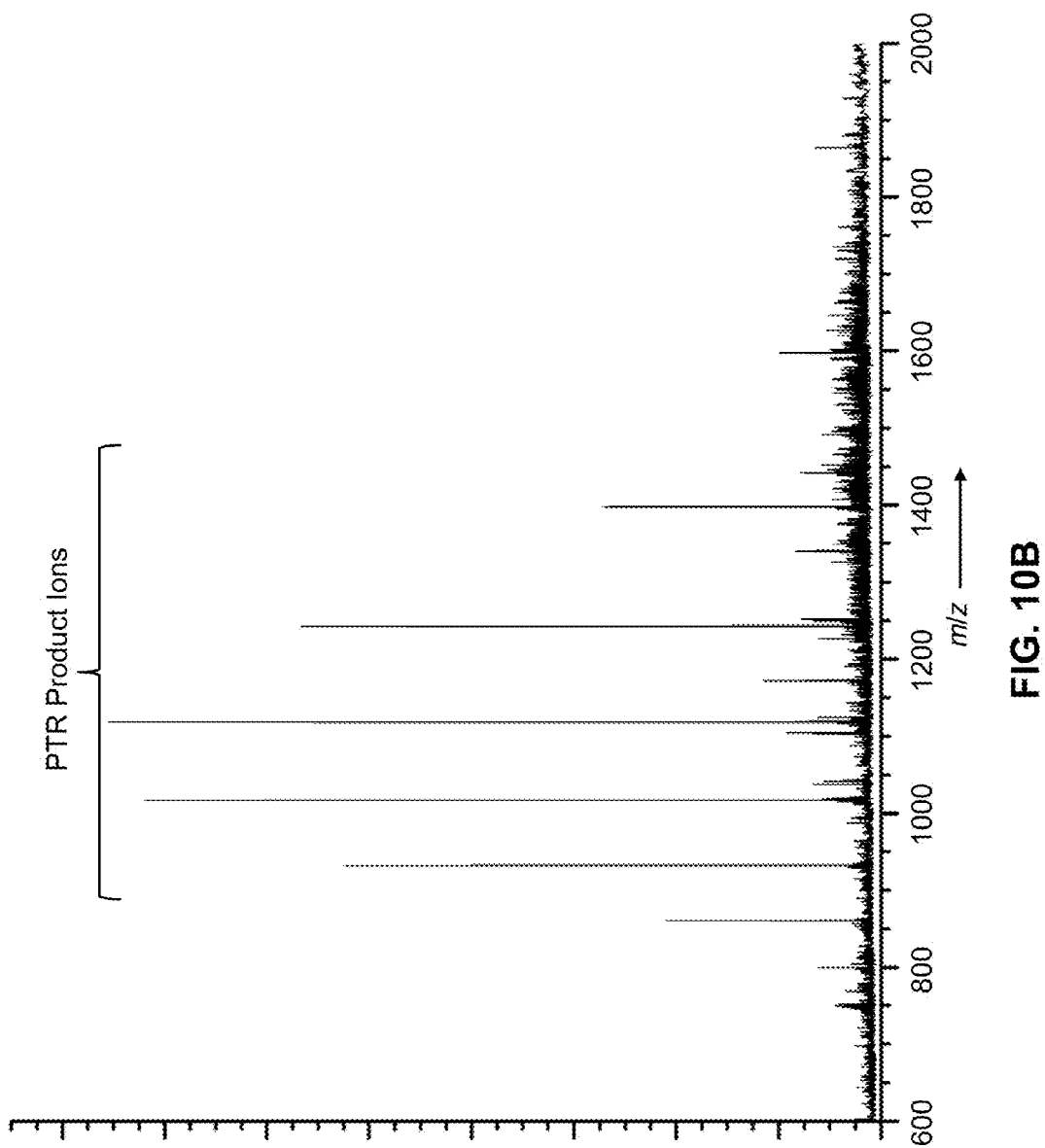
FIG. 10B is a PTR product ion spectrum generated by reacting sulfur hexafluoride for 10 ms with an isolated population of ions of the sample of FIG. 10A within a 10 Th wide isolation window centered at 750 Th.

FIGS. 10A and 10B show the results of a similar chromatography/MS experiment obtained from eluate at a retention time of 42 min. and 30 s. from a sixty-minute gradient elution run. As shown in FIG. 10A, a high background at this elution time causes difficulty in identifying analyte peaks in the full-scan spectrum. However, the PTR product ion spectrum plotted in FIG. 10B is much more amenable to interpretation and mass spectral deconvolution. The PTR product ion spectrum exhibits the mass spectral signatures of three distinct proteins—specifically having molecular weights 11165.92 Da, 13480.28 Da and 18727.23 Da—that would not otherwise be observed. In this instance, the PTR product ions were generated from isolated precursor ions generated from the mass spectral window, indicated by box 610 in FIG. 10A, of 10 Th width centered at m/z 750. By performing this type of analysis upon eluates that elute at various different retention times during the course of a single experiment, a sufficient number of sample peptides may be recognized so as to enable identification of a microorganism to the species, subspecies, or strain level. As also indicated by the results shown in FIGS. 9A-9B, if there is m/z overlap of protein ions from the full mass spectrum within the isolation window, then the protein will also be seen in the PTR product ion mass spectrum.

Figure 11A:
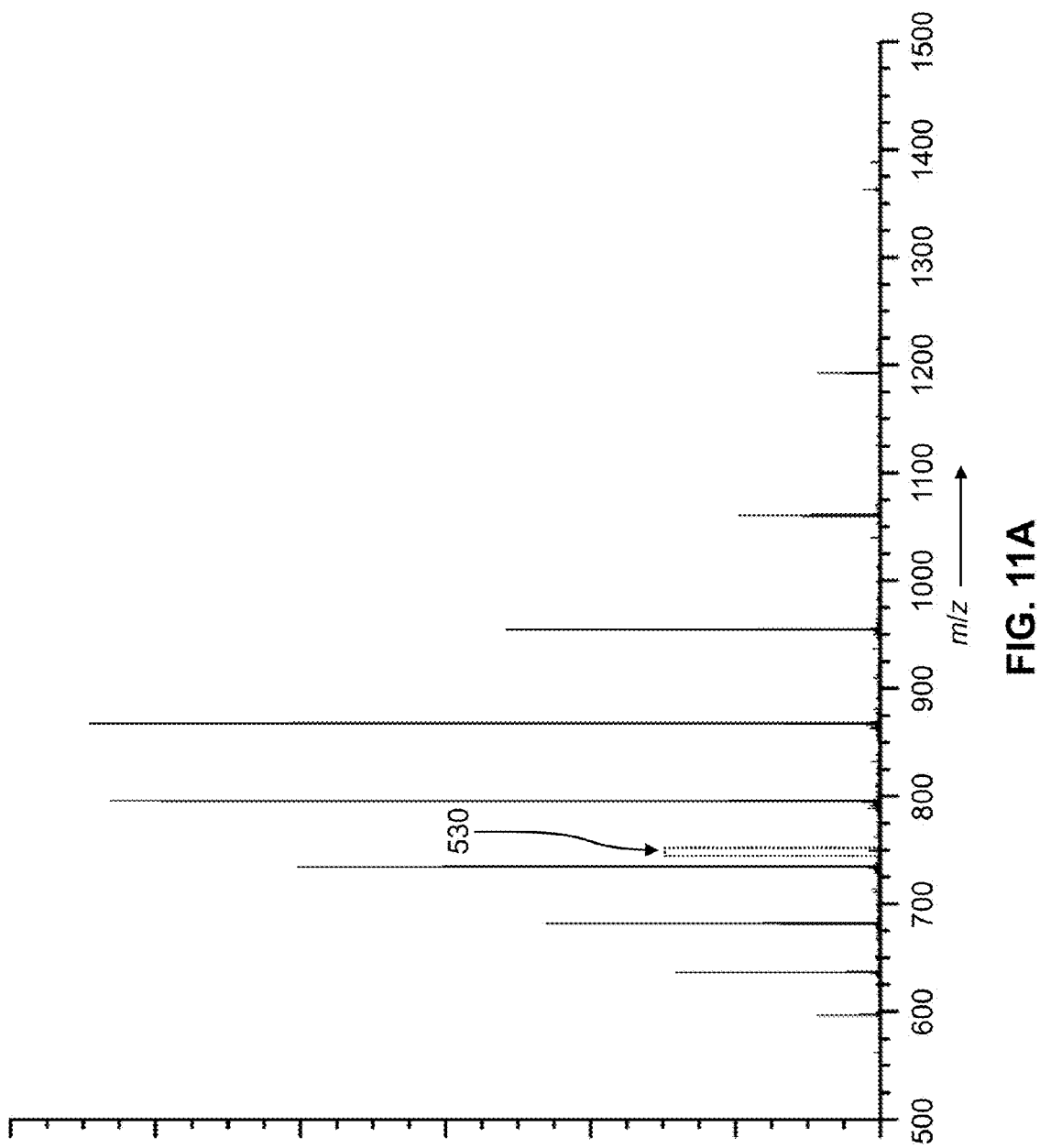
FIG. 11A is a full scan mass spectrum of first-generation ions generated from eluate at a retention time of 18 min. and 9 s. during the course of a thirty-minute gradient reverse-phase liquid chromatography separation.
Figure 11B:
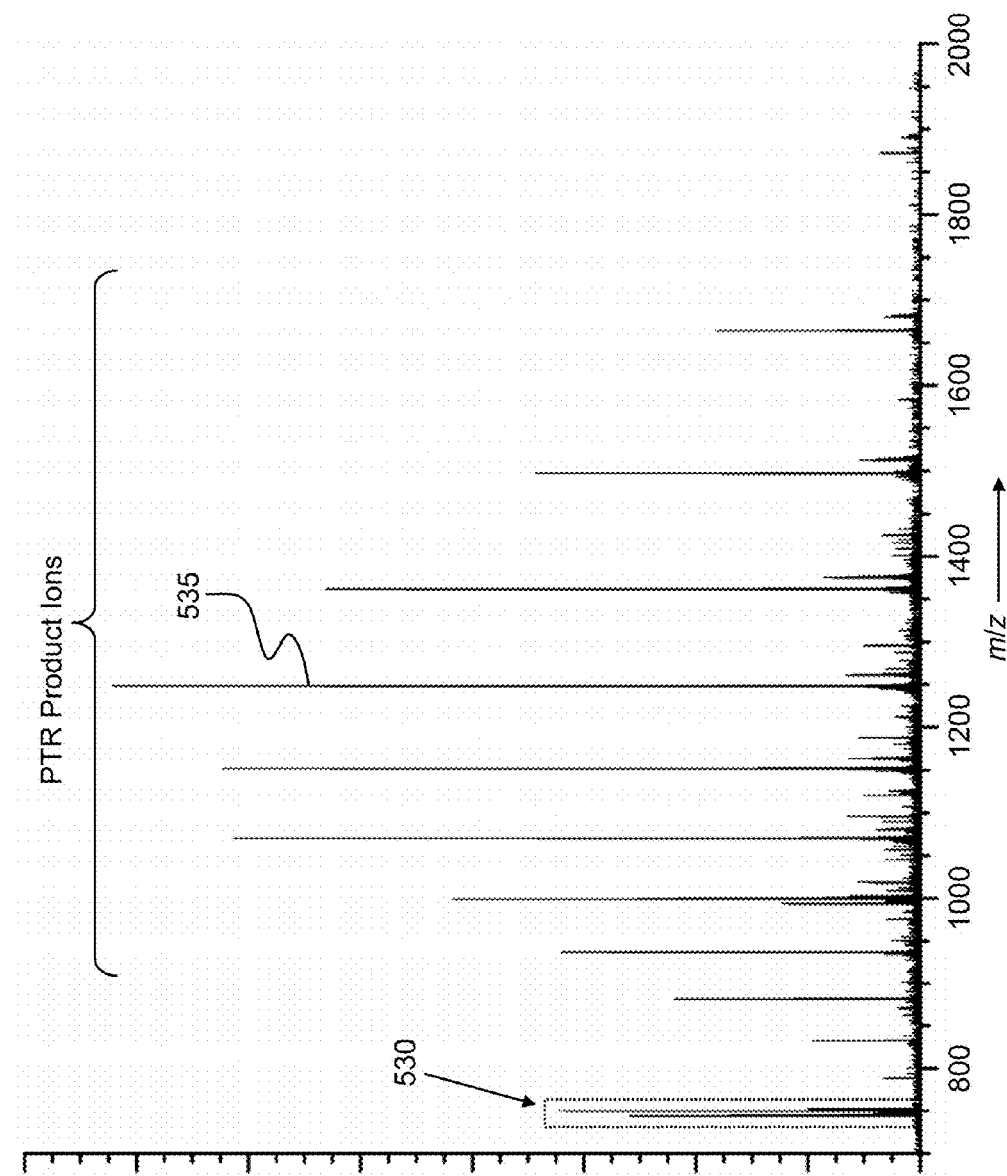
FIG. 11B is a PTR product ion spectrum generated by reaction of PTR reagent ions with an isolated population of ions of the sample of FIG. 11A within a 10 Th wide isolation window centered at 750 Th.
Figure 11C:
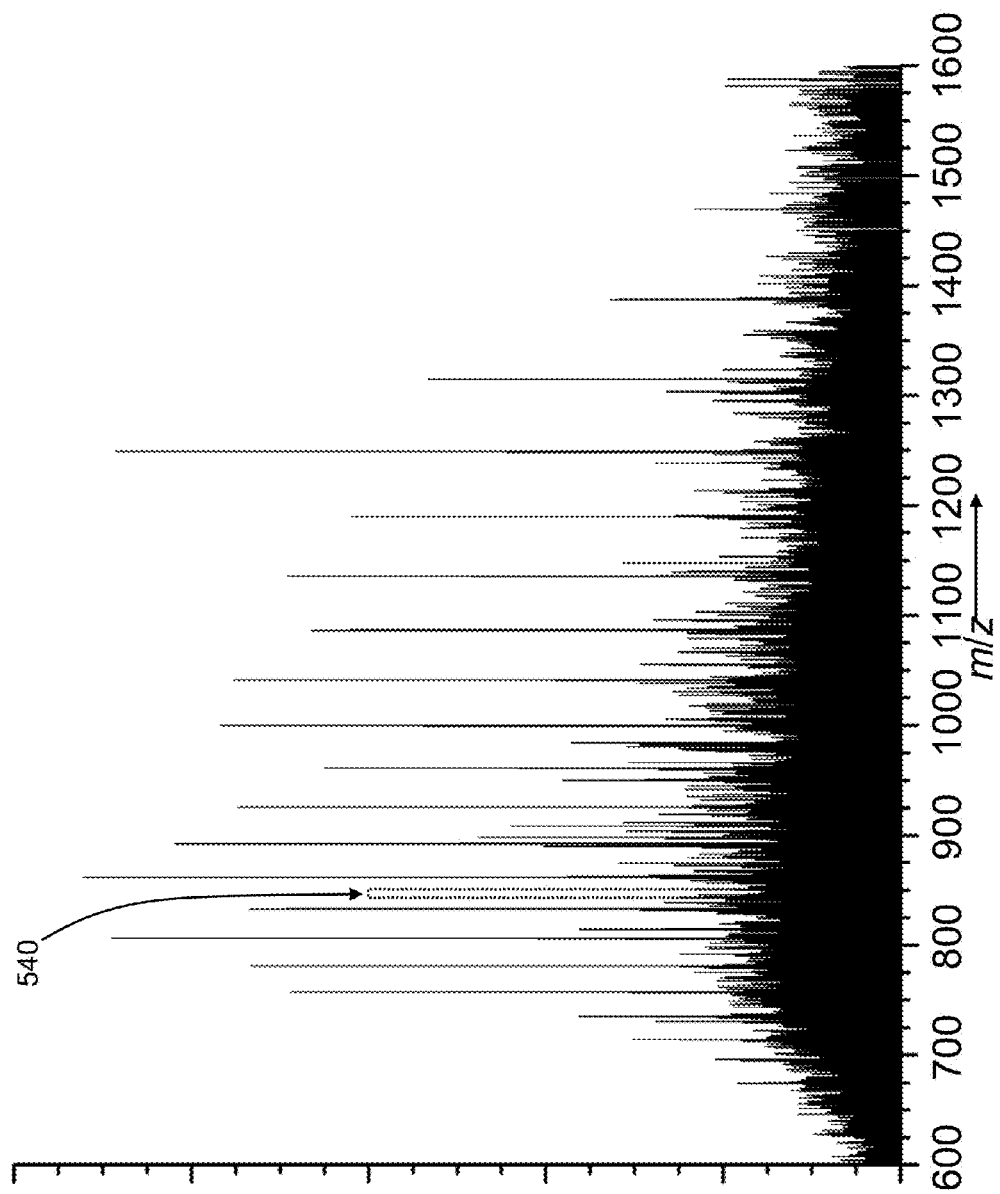
FIG. 11C is a full scan mass spectrum of first-generation ions generated from eluate at a retention time of 22 min. and 27 s. during the course of the same thirty-minute gradient reverse-phase liquid chromatography separation of which the earlier elution results are plotted in FIG. 11A.

Interestingly, the full scan mass spectrum and PTR product-ion mass spectrum can provide complementary information, as illustrated in FIGS. 11A and 11B which represent mass spectral results obtained from eluate eluting at a retention time of 18 min. and 9 s. over the course of a thirty-minute chromatographic separation. In this example, the full-scan mass spectrum (FIG. 11A) exhibits a strong mass spectral signature of essentially a single protein having a molecular weight of 9534.3 Da, However, when a PTR product ion spectrum is generated from ions isolated within a 10 Th wide window centered around m/z 750 Th (box 530), the mass spectral signature comprises a strong signal from a protein having a molecular weight of 14965.5 Da (best represented by the peak 535 of the +12 charge state at approximately 1247 Th) along with five other minor proteins having molecular weights of 12669.8 Da, 14150.0 Da, 14236.1 Da, 14965.5 Da, and 15117.5 Da. FIG. 11C is a full-scan mass spectrum obtained from eluate eluting during the same chromatographic separation at a retention time of 22 min. and 27 s. The spectrum includes peaks indicating the presence of a protein having a molecular weight of 24961.3 Da. Upon PTR reaction of ions isolated within the isolation window 540, the PTR product ion spectrum shown in FIG. 11D was obtained. The mass spectral signature in the PTR product ion spectrum includes a relatively strong signal from a protein having a molecular weight of 28461.5 Da (best represented by the peak 545 of the +22 charge state at approximately 1294 Th) as well as two other proteins having molecular weights of 18590.5 Da and 20168.0 Da. Thus, from just the data at these two retention times, it is possible to detect the presence and the molecular weights of eleven different proteins. Additional Examples The following paragraphs list additional specific examples of various specific embodiments in accordance with the present teachings.

Example 1

A method for identifying the presence or absence of a protein or polypeptide analyte compound within a liquid sample comprising a mixture of compounds that includes a plurality of protein compounds or a plurality of polypeptide compounds or pluralities of both protein and polypeptide compounds, the method comprising:
  (a) introducing a portion of the liquid sample into an electrospray ionization source of a mass spectrometer;
  (b) forming positively charged ions of the mixture of compounds of the portion of the liquid sample by electrospray ionization, the positively charged ions comprising a plurality of ion species;
  (c) isolating a first subset of the ion species comprising a first mass-to-charge (m/z) ratio range that includes an m/z ratio of a particular predetermined multiply-protonated molecular species of the analyte compound;
  (d) generating a plurality of first-generation product ion species from the isolated first subset of ion species by causing the isolated first subset of ion species to be reacted, for a predetermined time duration, with reagent anions that, upon reaction, extract protons from each of one or more ion species that comprises a protonated molecular species of a protein or polypeptide compound;
  (e) generating a mass spectrum, using a mass analyzer, of either the first-generation product ion species or of second-generation product ion species generated from the first-generation product ion species;
  (f) conducting a search of the mass spectrum of either the first-generation or the second-generation product ion species for a set of one or more m/z ratios that are diagnostic of the protein or polypeptide analyte compound; and
  (g) identifying the presence of the analyte compound within the sample if the set of one or more m/z ratios is identified in the mass spectrum.

Example 2

A method as recited in Example 1, further comprising repeating the steps (a) through (e) a second time, wherein the steps (f) and (g) are performed during or prior to the second performing of the steps (a) through (e).

Example 3

A method as recited in Example 1, further comprising repeatedly performing steps (a) through (g) a plurality of times, wherein each repetition of step (a) comprises introducing, into the electrospray ionization source, an eluate from a chromatographic column corresponding to a respective retention time.

Example 4

A method as recited in Example 1, wherein the step (f) comprises conducting a search of the mass spectrum of the first-generation product ion species for a series of m/z ratios that correspond to a sequence of multiply-protonated ion species of the analyte compound that are progressively charge-reduced with respect to the charge state of the particular predetermined multiply-protonated molecular species.

Example 5

A method as recited in Example 1, wherein: the step (c) comprises further isolating a second subset of the ion species comprising a second m/z ratio range that includes an m/z ratio of a particular predetermined multiply-protonated molecular species of a second protein or polypeptide analyte compound;
the step (f) comprises conducting an additional search of the mass spectrum of either the first-generation or the second-generation product ion species for a second set of one or more m/z ratios that are diagnostic of the second protein or polypeptide analyte compound; and the step (g) comprises identifying the presence of the second analyte compound within the sample if the second set of m/z ratios is identified in the mass spectrum.

Example 6

A method as recited in Example 5, wherein the first m/z ratio range is identical to the second m/z ratio range.

Example 7

A method as recited in Example 5, wherein the step (c) comprises simultaneously isolating the first subset of the ion species comprising the first m/z ratio and the second subset of the ion species comprising the second m/z ratio range such that the first and second m/z ratio ranges are non-contiguous.

Example 8

A method as recited in Example 1, wherein the step (d) of generating a plurality of first-generation product ion species comprises causing the isolated first subset of ion species and reagent anions to be reacted for a time duration that causes the product ion species to be stable against decomposition during the subsequent generation of the mass spectrum in step (e).

Example 9

A method as recited in Example 8, wherein the step (e) comprises generating a mass spectrum of the first-generation product ion species using a mass analyzer that generates the mass spectrum by detecting image currents caused by motions of the ions of the product ion species within an ion trap.

Example 10

A method as recited in Example 1, wherein the step (d) of generating a plurality of first-generation product ion species includes applying a supplemental AC voltage across electrodes of an ion trap within which the isolated first subset of ion species are reacted with reagent anions, wherein a frequency of the supplemental AC voltage is such that ion-ion reaction between the reagent anions and selected first-generation product ion species is inhibited.

Example 11

A method as recited in Example 10, wherein the frequency of the supplemental AC voltage is such that, subsequent to the execution of step (d), product ions formed from the analyte compound exist substantially as a single ion species having a particular charge state.

Example 12

A method as recited in Example 11, wherein: the step (e) comprises generating a mass spectrum of the first-generation product ion species; and wherein the mass of the single ion species is greater than 20,000 Da and the charge state of the single ion species is sufficiently great such that ions of the single ion species may be detected, during the generation of the mass spectrum, by either a quadrupole mass analyzer, a Fourier transform ion cyclotron resonance mass spectrometer or an electrostatic trap mass analyzer.

Example 13

A method as recited in Example 1, wherein the step (e) of generating a mass spectrum comprises generating a mass spectrum of second-generation product ion species, wherein the second-generation product ion species are generated by the steps of: isolating a subset of the first-generation product ion species comprising a particular product-ion m/z ratio range; and fragmenting the isolated subset of the first-generation product ion species so as to form fragment ion species, wherein the fragment ion species comprise the second-generation product ion species.

Example 14

A method as recited in Example 1, wherein the step (e) of generating a mass spectrum comprises generating a mass spectrum of second-generation product ion species, wherein the second-generation product ion species are generated by:
causing the first-generation product ion species to be reacted, for a second predetermined time duration, with the reagent anions, wherein products of reaction between the first-generation product ion species and the reagent anions comprise the second-generation product ion species.

Example 15

A method as recited in Example 14, wherein a supplemental AC voltage is applied across electrodes of an ion trap within which the first-generation product ion species are reacted with the reagent anions, wherein a frequency of the supplemental AC voltage is such that ion-ion reaction between the reagent anions and selected product ion species is inhibited.

Example 16

A method as recited in any one of Examples 1-15, further comprising generating the liquid sample comprising the mixture of compounds by a procedure comprising:
(i) culturing microorganisms or cells;
(ii) lysing the cultured microorganisms or cells; and
(iii) extracting proteins from the lysate of cultured microorganisms or cells.

Example 17

A method as recited in Example 16, wherein the step (iii) of extracting the liquid sample from the lysate includes passing the lysate through a solid-phase-extraction apparatus.

Example 18

A method of identifying the presence or absence of a microorganism type in a sample, comprising:
(i) identifying a list of analyte compounds whose simultaneous presence in the sample is diagnostic of the presence of the microorganism type in the sample, said list of analyte compounds comprising protein compounds, polypeptide compounds or both protein and polypeptide compounds;
(ii) extracting, from the sample, a liquid solution comprising a mixture of sample-derived proteins and polypeptides;
(iii) for each respective analyte compound in the list, performing the steps of:
  (a) introducing a portion of the liquid solution into an electrospray ionization source of a mass spectrometer;
  (b) forming positively charged ions of the mixture of compounds of the portion of the liquid solution by electrospray ionization, the positively charged ions comprising a plurality of ion species;
  (c) isolating a first subset of the ion species comprising a first mass-to-charge (m/z) ratio range that includes an m/z ratio of a particular predetermined multiply-protonated molecular species of the respective analyte compound;
  (d) generating a plurality of first-generation product ion species from the isolated first subset of ion species by causing the isolated first subset of ion species to be reacted, for a predetermined time duration, with reagent anions that, upon reaction, extract protons from each of one or more ion species that comprises a protonated molecular species of a protein or polypeptide compound;
  (e) generating a mass spectrum, using a mass analyzer, of either the first-generation product ion species or of second-generation product ion species generated from the first-generation product ion species;
  (f) conducting a search of the mass spectrum of either the first-generation or the second-generation product ion species for a set of one or more m/z ratios that are diagnostic of the respective analyte compound; and
  (g) identifying the presence of the respective analyte compound within the liquid solution if the set of one or more m/z ratios is identified in the mass spectrum; and
(iv) identifying the presence of the microorganism type within the sample if the presence of each and every analyte compound of the list of analyte compounds is identified within the liquid solution.

Example 19

A method of identifying the presence or absence of a microorganism type in a sample, comprising:
(i) identifying a list of analyte compounds whose simultaneous presence in the sample is diagnostic of the presence of the microorganism type in the sample, said list of analyte compounds comprising protein compounds, polypeptide compounds or both protein and polypeptide compounds;
(ii) extracting, from the sample, a liquid solution comprising a mixture of sample-derived proteins and polypeptides;
(iii) introducing at least a first portion of the liquid solution into an ionization source of a mass spectrometer;
(iv) generating, from the at least first portion of the liquid solution at the ionization source, positively charged ions of the mixture of compounds, the positively charged ions comprising a plurality of ion species;
(v) isolating at least a first subset of the plurality of ion species, each isolated subset of the at least a first isolated subset comprising a respective mass-to-charge (m/z) ratio range;
(vi) generating a plurality of first-generation product ion species from each isolated subset of ion species by causing each said isolated subset of ion species to be reacted, for a predetermined time duration, with reagent anions that, upon reaction, extract protons from each of one or more ion species of said isolated subset of ion species that comprises a protonated molecular species of a protein or polypeptide compound;
(vii) generating at least one mass spectrum, using a mass analyzer of the mass spectrometer, of either first-generation product ion species or second-generation product ion species generated by further reaction of the first-generation product ion species;
(viii) for each respective analyte compound in the list, performing the steps of:
  (a) conducting a search of the at least one mass spectrum of either the first-generation or the second-generation product ion species for a set of one or more m/z ratios that are diagnostic of the respective analyte compound; and
  (b) identifying the presence of the respective analyte compound within the liquid solution if the set of one or more m/z ratios is identified in the mass spectrum; and
(ix) identifying the presence of the microorganism type within the sample if the presence of each and every analyte compound of the list of analyte compounds is identified within the liquid solution.

Example 20

A method as recited in Example 19, wherein a performing of the steps (a) and (b) is performed concurrently with the performing of one or more of the steps (iii) through (vii).

Example 21

A method as recited in Example 19, wherein the microorganism type is defined as a particular genus of bacteria and the list of analyte compounds includes a sufficient number of analyte compounds that are diagnostic of the particular genus of bacteria to enable identification of the presence or absence of the particular genus of bacteria in the sample.

Example 22

A method as recited in Example 19, wherein the microorganism type is defined as a particular species of bacteria and the list of analyte compounds includes a sufficient number of analyte compounds that are diagnostic of the particular species of bacteria to enable identification of the presence or absence of the particular species of bacteria in the sample.

Example 23

A method as recited in Example 19, wherein the microorganism type is defined as a particular sub-species of bacteria and the list of analyte compounds includes a sufficient number of analyte compounds that are diagnostic of the particular sub-species of bacteria to enable identification of the presence or absence of the particular sub-species of bacteria in the sample.

Example 24

A method as recited in Example 19, wherein the microorganism type is defined as a particular strain of virus and the list of analyte compounds includes a sufficient number of analyte compounds that are diagnostic of the particular viral strain to enable identification of the presence or absence of the particular viral strain in the sample.

Example 25

A method as recited in Example 19, wherein the microorganism type is defined as a particular strain of virus and the list of analyte compounds includes a sufficient number of analyte compounds that are diagnostic of the particular viral strain to enable identification of the presence or absence of the particular viral strain in the sample.

Example 26

A method for identifying the presence or absence of a protein or polypeptide analyte compound within a sample comprising a mixture of compounds that includes a plurality of protein compounds or a plurality of polypeptide compounds or pluralities of both protein and polypeptide compounds, the method comprising:
  (a) introducing a portion of the liquid sample into an electrospray ionization source of a mass spectrometer;
  (b) forming positively charged ions of the mixture of compounds of the portion of the liquid sample by electrospray ionization, the positively charged ions comprising a plurality of first-generation ion species;
  (c) isolating a plurality of subsets of the first-generation ion species comprising respective mass-to-charge (m/z) ratio ranges, wherein each m/z ratio range includes an m/z ratio of an ion species comprising a respective protonation state of the analyte compound;
  (d) generating a plurality of first-generation product ion species from the isolated plurality of subsets of the first-generation ion species by causing the isolated plurality of subsets of the first-generation ion species to be reacted, for a predetermined time duration, with reagent anions that, upon reaction, extract protons from each ion species that comprises a respective protonation state of the analyte compound;
  (e) generating a mass spectrum of the first-generation product ion species; and
  (f) identifying either the presence of the analyte compound within the sample if the mass spectrum comprises one or more lines at respective predetermined m/z ratios that comprise respective intensities above a predetermined threshold or the absence of the analyte compound within the sample otherwise.

Example 27

A method as recited in Example 26, further comprising repeatedly performing steps (a) through (f) a plurality of times, wherein each repetition of step (a) comprises introducing, into the electrospray ionization source, an eluate from a chromatographic column corresponding to a respective retention time.

Example 28

A method as recited in Example 26, wherein the step (f) further comprises determining, if the mass spectrum comprises one or more lines at respective predetermined m/z ratios that comprise respective intensities above a predetermined threshold, a quantity or concentration of the analyte compound within the sample based on the one or more intensities.

Example 29

A method as recited in Example 26, further comprising, after the step (b) of forming positively charged ions and prior to the step (c) of isolating a plurality of subsets of the first-generation ion species, the steps of:
  (b1) isolating a subset of the first-generation ion species comprising a randomly-selected mass-to-charge (m/z) ratio range;
  (b2) generating a plurality of product ion species from the isolated subsets of the first-generation ion species by causing the isolated subset of the first-generation ion species to be reacted with reagent anions that, upon reaction, extract protons from each ion species that comprises a respective protonation state of the analyte compound or a respective protonation state of another protein or polypeptide compound;
  (b3) generating a mass spectrum of the product ion species; and
  (b4) automatically determining the m/z ratio ranges to be used in the subsequent step (c), based on the mass spectrum of the product ions.

Example 30

A method as recited in Example 28, wherein the step (b4) comprises automatically determining, from the mass spectrum, a set of m/z ratios corresponding to multiply-protonated ion species of the other protein or polypeptide compound.

Example 31

A method of identifying the presence of absence of a microorganism in a sample, comprising:
  making an extract of the sample;
  repeatedly executing the method recited in Example 26 so as to, at each execution, identify the presence or absence of a different respective protein or polypeptide analyte compound within the sample extract; and
  identifying the presence of the microorganism within the sample if the presence of each respective protein or polypeptide analyte compound within the sample extract or the absence of the microorganism within the sample otherwise.

CONCLUSIONS

The use of PTR-type of ion-ion reactions as taught in this document has several advantages for analysis of complex mixtures of protein or polypeptide ions. A first significant advantage is provided by the greatly improved signal-to-noise ratio as may be readily observed by comparing FIG. 3 with FIG. 4. Even though some charge is lost (i.e., complete neutralization) as a result of the PTR process, a significant signal-to-noise ratio is gained as a result of the reaction of multiply-charged proteins with singly charged anions. The rate of such a reaction is proportional to the square of the product of the charges. Thus, the originally highly-charged analyte ions are converted into less-charged PTR product ions whose mass spectral signatures appear at significantly greater mass-to-charge ratios. By contrast, low-charge-state chemical background ions are less significantly affected by the PTR process during a typical experimental reaction period because of the low rates of reaction of such ions. This process essentially removes the mass spectral signatures of the proteins and polypeptides from the low-mass, low-charge-state chemical background "noise". For example, as shown in FIG. 4, the background ions are represented by the large singly-charged peak that is "left behind" at m/z≈642. It is also believed that adducts or water molecules still adhered to large proteins are removed as a result of the exothermic heat of reaction (at least 125 kcal/mol) deposited by the PTR reaction. The transformation of such ions into simple protonated molecules may further enhance signal-to-noise characteristics. Potentially, the number of protein identifications obtained via this approach could exceed current complex top-down methods utilizing some form of separation technology.

A second important advantage associated with methods in accordance with the present teachings is provided by greatly improved charge state assignment. For example, the inventors have experimentally determined that approximately 75% of the charge state assignments for individual charge states may be correctly assigned by employing methods in accordance with the present teachings. This improved ability to recognize charge states results from the significantly improved signal-to-noise ratio. In turn, this provides more accurate determination of the molecular weight of the protein or polypeptide. This comparison applies to the current Patterson-FFT charge state algorithm that is frequently used for real-time charge state determination. Another important advantage associated with methods in accordance with the present teachings is provided by the ability to perform rapid throughput analyses. When combined with the Fast Partial Chromatographic Separation technique applied above, these methods allow for analyses of samples in a high throughput fashion on a time scale of one minute or less.

The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. Thus, the reader should be aware that the specific discussion may not explicitly describe all embodiments possible; many alternatives are implicit. Accordingly, many modifications may be made by one of ordinary skill in the art without departing from the scope of the invention as described by the claims. Neither the description nor the terminology is intended to limit the scope of the invention. Any patents, patent applications, patent application publications or other literature mentioned herein are hereby incorporated by reference herein in their respective entirety as if fully set forth herein.

APPENDIX—MATHEMATICAL COMPUTATIONAL METHODS

1. Introduction

Structural elucidation of ionized molecules of complex structure, such as proteins, is often carried out using a tandem mass spectrometer that is coupled to a liquid chromatograph. The general technique of conducting mass spectrometry (MS) analysis of ions generated from compounds separated by liquid chromatography (LC) may be referred to as "LC-MS". If the mass spectrometry analysis is conducted as tandem mass spectrometry (MS/MS), then the above-described procedure may be referred to as "LC-MS/MS". In conventional LC-MS/MS experiments a sample is initially analyzed by mass spectrometry to determine mass-to-charge ratios (m/z) corresponding to the peaks of interest. The sample is then analyzed further by performing product ion MS/MS scans on the selected peak(s). Specifically, in a first stage of analysis, frequently referred to as "$MS^1$", a full-scan mass spectrum, comprising an initial survey scan, is obtained. This full-scan spectrum is the followed by the selection (from the results obtained) of one or more precursor ion species. The precursor ions of the selected species are subjected to reaction, generally fragmentation such as may be accomplished employing a collision cell or employing another form of fragmentation cell such as those employing surface-induced dissociation, electron-transfer dissociation or photon dissociation. In a second stage, the resulting fragment (product) ions are detected for further analysis (frequently referred to as either "MS/MS" or "$MS^2$") using either the same or a second mass analyzer. A resulting product spectrum exhibits a set of fragmentation peaks (a fragment set) which, in many instances, may be used as a means to derive structural information relating to the precursor peptide or protein or other biochemical oligomer. It should be noted that, using the fragment ions as a starting population, the process of ion selection and subsequent fragmentation may be repeated yet again, thereby yielding an "$MS^3$" spectrum. In the general case, a mass spectrum obtained after (n−1) iterated stages of selection and fragmentation may be referred to as an "$MS^n$" spectrum. This is a time-consuming process because the sample needs to be analyzed at least twice and the MS/MS data is only recorded for a limited number of components.

Most presently available mass spectrometers capable of tandem analysis are equipped with an automatic data-dependent function whereby, when selecting the precursor ion for $MS^2$ analysis from the ion peaks in $MS^1$, the ion precursors are selected in decreasing intensities. In a simple data-dependent experiment shown in FIG. 12A, a detector continuously measures total current attributable to ions entering a mass spectrometer detector. A threshold intensity level A8 of the total ion current is set below which only $MS^1$ data is acquired. As a first component—detected as peak A10—elutes, the total ion current intensity crosses the threshold A8 at time t1. When this occurs, an on-board processor or other controller of the mass spectrometer determines the most intense ion in the $MS^1$ spectra and immediately initiates an MS/MS scan with regard to the most intense ion. Subsequently, the leading edge of another elution peak A12 is detected. When the total ion current once again breaches the threshold intensity A8 at time t3, an MS/MS scan is initiated with regard to the most intense ion detected after time t3. Generally, the peak A12 will correspond to the elution of a different chemical component and, thus, the most abundant ion detected after time t3 will be different from the ion for which MS/MS analysis was conducted during the elution peak A10. In this way, both MS and MS/MS spectra are acquired on each component as it elutes.

Figure 12A:
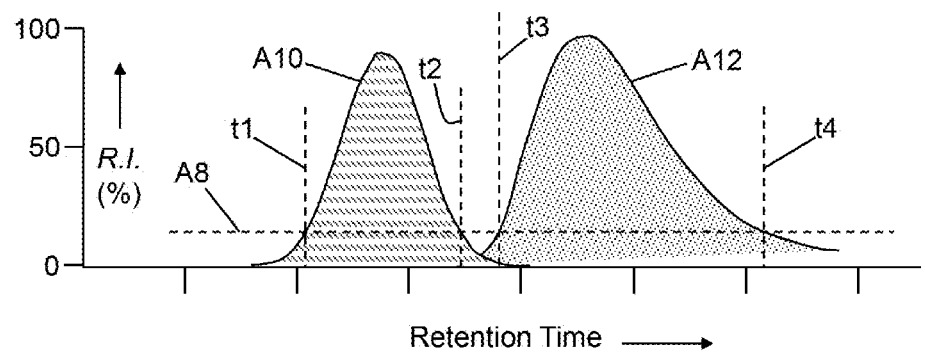
FIG. 12A is a schematic illustration of simple intensity-threshold-based data dependent mass spectral analysis of two analytes exhibiting well-resolved chromatographic peaks.

The simple data dependent experiment described above works well with chromatographically resolved or partially resolved components, as are illustrated in FIG. 12A. However, in a very complex mixture there may be components whose elution peaks completely overlap, as illustrated in the graph of ion current intensity versus retention time in FIG. 12B. In this example elution peak A11 represents the ion current attributable to ion m11, and elution peak A13 represents the ion current attributable to ion m13, the masses of these ions being schematically illustrated in the mass spectrum representation in inset box A16. In the hypothetical situation shown in FIG. 12B, there is almost perfect overlap of the elution of the compounds that give rise to ions m11 and m13, with the mass spectral intensity of ion m11 always being greater than that of ion m13 during the course of the elution. Under these conditions, the simple data-dependent technique discussed above with reference to FIG. 12A will fail to ever initiate MS/MS analysis of ion m13 (and possibly other important ions), since only the most intense component (m11) will be selected for MS/MS.

Figure 12B:
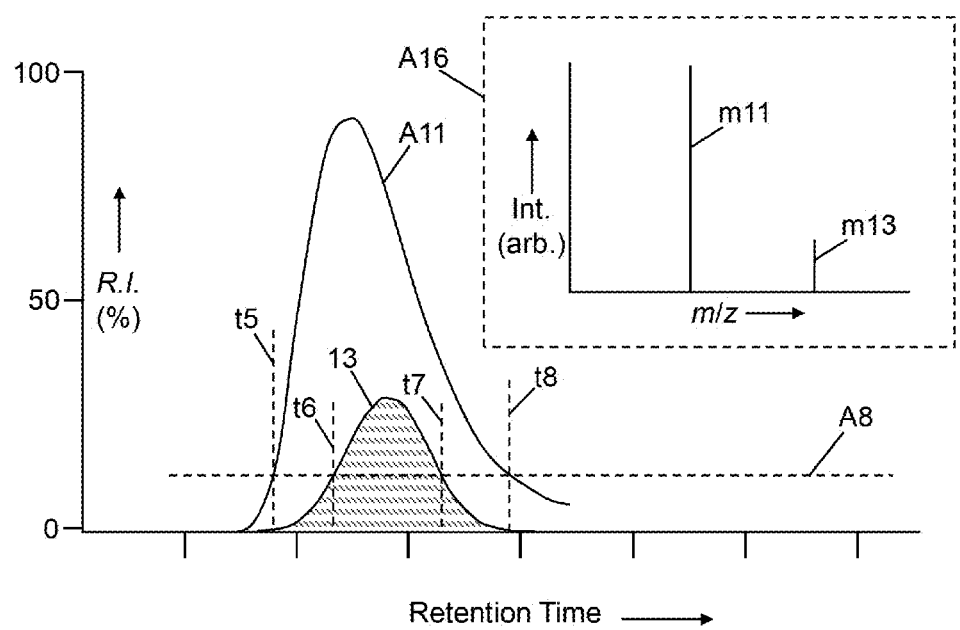
FIG. 12B is a schematic illustration of a portion of a chromatogram with highly overlapping elution peaks, both of which are above an analytical threshold.
Figure 12C:
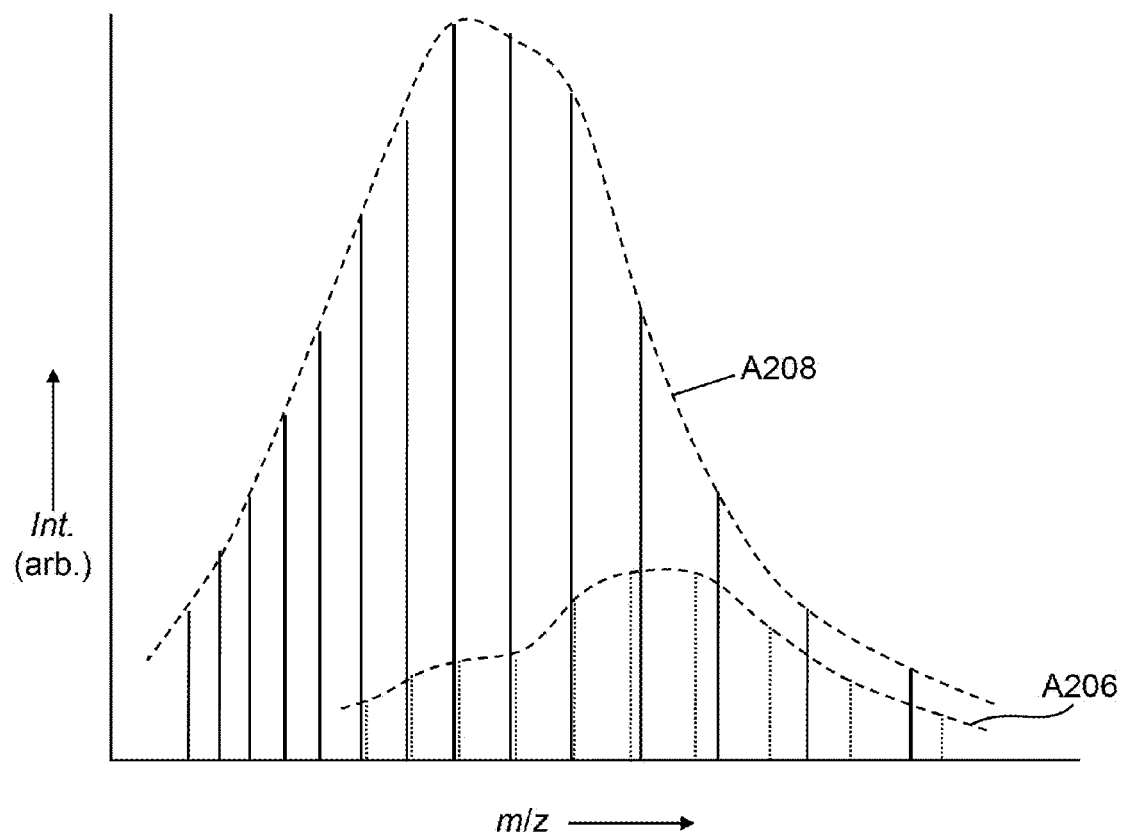
FIG. 12C is an illustration of multiple interleaved mass spectral peaks of two simultaneously eluting biopolymer analytes.

The hypothetical two-ion situation illustrated in FIG. 12B is a simplified example. Most modern mass spectrometer instruments are capable of performing a series of MS/MS analyses with regard to each respective one of several abundant ions detected in an $MS^1$ analysis. Typically, instead of choosing just a single most-abundant precursor, modern instruments will select the "top P number of the most abundant precursors" for tandem mass analysis based on the information of a preceding $MS^1$ data acquisition, where the number P is either a constant or perhaps a variable input by a user. Nonetheless, the basic issue demonstrated by FIG. 12B remains, especially for multicomponent samples of biopolymer analytes which may give rise to tens to hundreds of mass spectral peaks in a single mass spectrum. Regardless of how such a sample is introduced into a mass spectrometer (for example, by chromatographic separation, flow injection, or capillary electrophoresis; as a chemical separate delivered from a lab-on-a-chip device, by infusion or other method), more than one analyte may be represented in a single mass spectrum from a single time point, and each such analyte may give rise to many ions, as illustrated in hypothetical mass spectrum illustrated in FIG. 12C. In FIG. 12C, solid vertical lines outlined by envelope A208 represent centroids of a first set of mass spectral peaks generated from a first analyte compound and dotted vertical lines outlined by envelope A206 represent centroids of a second set of mass spectral peaks generated from a second co-eluting analyte compound. It is evident that, even if the number, P, of most-abundant peaks to be analyzed is equal to 10, for example, than only the ions of only one of the analyte compounds will be selected for MS/MS analysis using the traditional data dependent methods described above. Information relating to the second analyte will be lost. Further, the data so obtained will comprise redundant information on the same component.

To more successfully address the complexities of mass spectral analysis of co-eluting compounds, many mass spectral instruments also employ the so-called "Dynamic Exclusion" principle by which a mass-to-charge ratio is temporarily put into an exclusion list after its $MS^n$ spectrum is acquired. The excluded mass-to-charge ratio is not analyzed by $MS^n$ again until a certain time duration has elapsed after the prior $MS^n$ spectrum acquisition. This technique minimizes a chance of fragmenting the same precursor ion in several subsequent scans, and allows a mass spectrometer to collect $MS^n$ spectra on other components having less intense peaks which would otherwise not be examined. After a selected period of time the excluded ion will be removed from the list so that any other compounds with the same mass-to-charge ratio can be analyzed. This time duration during which the ion species is on the exclusion list is generally estimated based on an average or estimated chromatographic peak width. Thus, use of the Dynamic Exclusion principle allows more data to be obtained on more components in complex mixtures.

Unfortunately, existing dynamic exclusion techniques may perform poorly for analyzing mass spectra of mixtures of complex biomolecules. For example, consider once again the hypothetical situation illustrated in FIG. 12C. If the ions depicted in FIG. 12C are analyzed using the dynamic exclusion principle, then at least 10 ion species derived from a single analyte (outlined by envelope A208) will be analyzed, in decreasing order of their intensities in the illustrated $MS^1$ spectrum, by $MS^n$ analysis prior to any peaks from the less abundant analyte (outlined by envelope A206) being considered. This sequence will occur regardless of the fact that each precursor each ions species is placed onto an exclusion list after its respective analysis. The amount of time consumed performing ten unnecessarily redundant $MS^n$ analyses may then lead to expiration of the exclusion time of the most abundant ion (or may lead to exhaustion of the time available to fully analyze a small number of most abundant ions), after which the entire sequence may of $MS^n$ analyses may be repeated.

A further complicating factor in the application of the dynamic exclusion principle to mass analysis of mixtures of complex biomolecules derives from the fact that the elution profiles of the various compounds are highly variable and difficult to predict. Different biopolymer compounds may exhibit different elution profiles as a result of complex interactions between a chromatographic stationary phase and a biopolymer with multiple molecular interaction sites. Moreover, the time profiles of various ions generated from even a single such compound may fail to correlate with the elution profile of the un-ionized compound or with the profiles of one another as a result of ionization suppression within an ionization source of a mass spectrometer.

As an example of the elution profile variability that may be encountered, FIG. 13 illustrates a set of chromatograms collected from a single liquid chromatography-mass spectrometry experimental run of an *E. Coli* extract. Total ion current is shown in the topmost chromatogram (curve A40) and various extracted ion chromatograms, illustrating the ion current that is contributed by respective m/z-ratio ranges are shown in the lowermost five plots (curves A50, A60, A70, A80 and A90). Curve A50 represents the m/z range 660.0-660.5 Da. Similarly, curves A60, A70, A80 and A90 represent m/z ranges 700.5-701.5 Da, 1114.5-1114.5 Da, 942.5-943.5 Da and 540.5-540.5 Da. Peaks A1, A2 and A3 are examples of peaks with broad chromatographic profiles. Peaks A4 and A5 are examples of narrow profiles. Peak A6 shows an extremely broad peak. The peak widths span over an order of magnitude, therefore severely limiting the applicability of an exclusion list having a pre-defined exclusion time duration. To address the above computational difficulties, the following describes an improved optimized computational method for making charge state assignments and for real-time recognition of multiplexed charge state distributions, this method referred to as the method of "Top P Unique Analyte-Specific Clusters".

2. Key Features of Self Consistent Map Charge Assignment Algorithm 2.1. Use of Centroids Exclusively.

Standard mass spectral charge assignment algorithms (e.g., Senko et al., 1995) use full profile data of the lines in a mass spectrum. By contrast, the novel approach which is employed in the present methods uses centroids. The key advantage of using centroids over line profiles is data reduction. Typically the number of profile data points is about an order of magnitude larger than that of the centroids. Any algorithm that uses centroids will gain a significant advantage in computational efficiency over that standard assignment method. For applications that demand real-time charge assignment, it is preferable to design an algorithm that only requires centroid data. The main disadvantage to using centroids is imprecision of the m/z values. Factors such as mass accuracy, resolution and peak picking efficiency all tend to compromise the quality of the centroid data. But these concerns can be mostly mitigated by factoring in the m/z imprecision into the algorithm which employs centroid data.

2.2. Intensity is Binary.

Another key departure from most existing algorithms is the encoding of intensities as binary (or Boolean) variables (true/false or present/absent) according to the present methods. The present methods only take into consideration whether a centroid intensity is above a threshold or not. If the intensity value meets a user-settable criterion based on signal intensity or signal-to-noise ratio or both, then that intensity value assumes a Boolean "True" value, otherwise a value of "False" is assigned, regardless of the actual numerical value of the intensity. Again the encoding of a numerical value as a simple binary value results in a significant data reduction. In many programming languages, a double-precision value uses eight bytes of memory storage whereas a binary (or Boolean) value uses just a single byte. Also, comparing Booleans is intrinsically much faster than comparing double-precision variables. A well-known disadvantage of using a Boolean value is the loss of information. However, if one has an abundance of data points to work with—for example, thousands of centroids in a typical high resolution spectrum, the loss of intensity information is more than compensated for by the sheer number of Boolean variables. Accordingly, the inventors' approach and, consequentially, the algorithms taught herein, exploit this data abundance to achieve both efficiency and accuracy.

Nonetheless, additional accuracy without significant computational speed loss can be realized by using approximate intensity values rather than just a Boolean true/false variable. For example, one can envision the situation where only peaks of similar heights are compared to each other. One can easily accommodate the added information by discretizing the intensity values into a small number of low-resolution bins (e.g., "low", "medium", "high" and "very high"). Such binning can achieve a good balance of having "height information" without sacrificing the computational simplicity of a very simplified representation of intensities.

2.3. Mass-to-Charge Values are Transformed and Assembled into Low-Resolution Bins and Relative Charge State Intervals are Pre-Computed Once and Cached for Efficiency.

Another innovation of the approach taught in the present disclosure is in transformation of m/z values of mass spectral lines from their normal linear scale in Daltons into a more natural dimensionless logarithmic representation. As may be seen from the detailed discussion following, this transformation greatly simplifies the computation of m/z values for any peaks that belong to the same protein, for example, but represent potentially different charge states. This transformation involves no compromise in precision. When performing calculations with the transformed variables, one can take advantage of cached relative m/z values to improve the computational efficiency.

2.4. Simple Counting-Based Scoring and Statistical Selection Criterion.

Combining the encoding of centroid intensities as Boolean values, and the transformation of m/z values, the present approach encodes the whole content of any mass spectrum in question into a single Boolean-valued array. The scoring of charge states reduces to just a simple counting of yes or no (true or false) of the Boolean variables at transformed m/z positions appropriate to the charge states being queried. Again, this approach bypasses computationally expensive operations involving double-precision variables. Once the scores are compiled for a range of potential charge states, the optimal value can easily be picked out by a simple statistical procedure. Using a statistical criterion is more rigorous and reliable than using an arbitrary score cutoff or just picking the highest scoring charge state.

2.5. Iterative Process to Achieve Optimality and Defined by Complete Self Consistency of Charge Assignment.

The final key feature of the present novel approach is the use of an appropriate optimality condition that leads the charge-assignment towards a solution. The optimal condition is simply defined to be most consistent assignment of charges of all centroids of the spectra. Underlying this condition is the reasoning that the charge state assigned to each centroid should be consistent with those assigned to other centroids in the spectrum. The present algorithm implements an iterative procedure to generate the charge state assignments as guided by the above optimality condition. This procedure conforms to accepted norms of an optimization procedure. That is, an appropriate optimality condition is first defined and then an algorithm is designed to meet this condition and, finally, one can then judge the effectiveness of the algorithm by how well it satisfies the optimality condition. Most existing approaches lack this logical framework, and their theoretical merits are therefore difficult to assess objectively.

3. Details of Decomposition Algorithm

Figure 14:
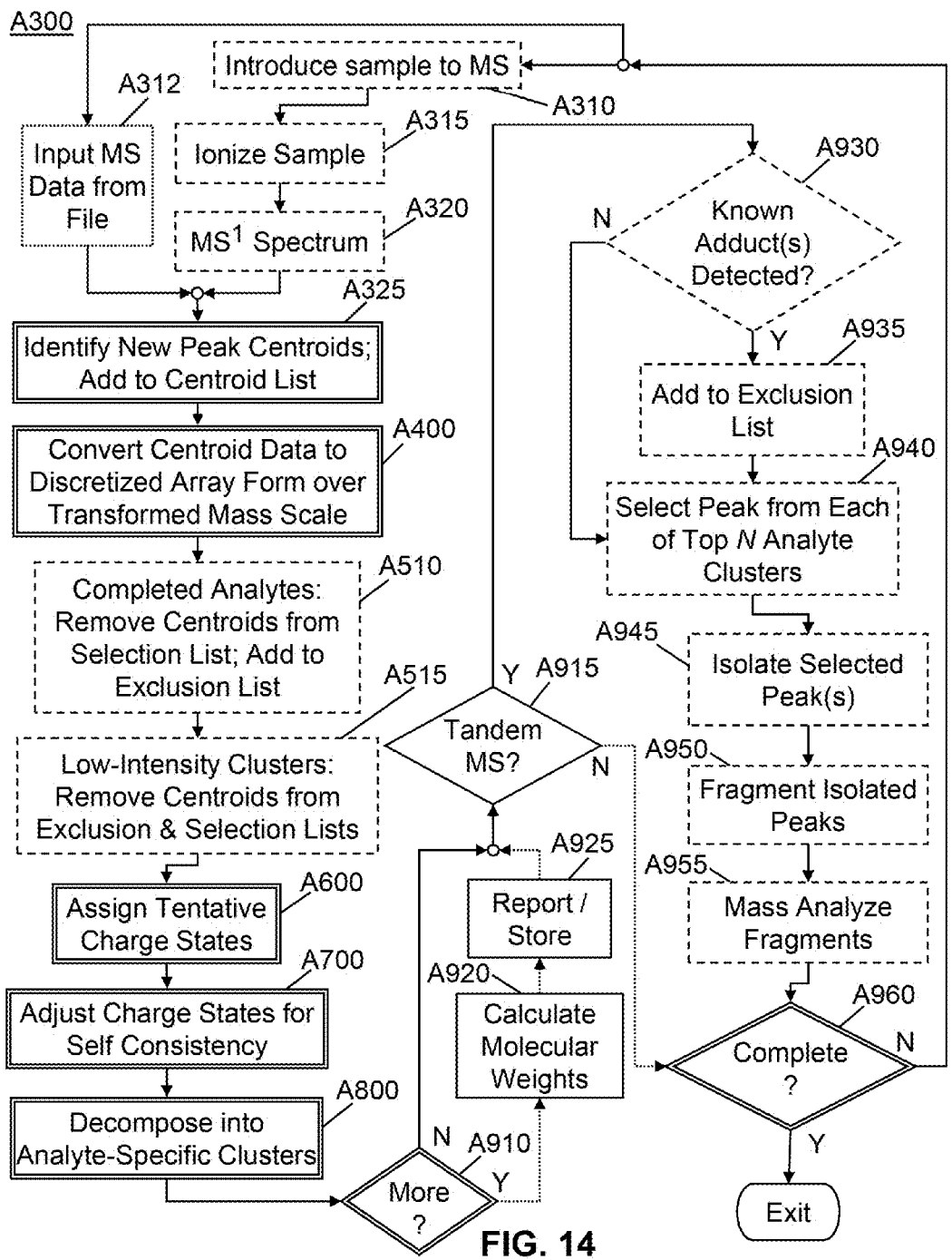
FIG. 14 is a flowchart of a general set of steps employed by various methods in accordance with the present teachings.

The inventors have developed methods that, inter alia, are capable of assigning self-consistent charge states to mass spectral lines and decomposing complex mass spectra comprising overlapping information pertaining to several analytes into multiple sets of lines, wherein each set of lines corresponds to a respective analyte. FIG. 14 is an overview flowchart of a general set of steps in accordance with the present teachings for accomplishing these results. Several operations listed in FIG. 14 are illustrated in greater detail in other flow diagrams of the accompanying set of drawings.

3.1. High-Level Methods.

As shown, FIG. 14 depicts at least two general execution or workflow pathways. According to a first general execution pathway or workflow—here termed "File-Deconvolution Workflow" only for purposes of reference—the methods of the present teachings are employed for the purposes of analyzing and possibly interpreting previously collected and stored mass spectral data. According to a second general execution pathway or workflow—here termed "Data-Dependent-Acquisition Workflow" only for purposes of reference—the methods of the present teachings are employed in a "real-time" or "online" fashion at the time that mass spectral data is being acquired and at least some aspects of the course of data acquisition are determined or controlled based on the results of computations or algorithms in accordance with the invention. Some steps illustrated in FIG. 14 are common to both of the above-defined execution pathways and are denoted in FIG. 14 by boxes defined by double lines. Other steps are exclusive to the Data-Dependent-Acquisition Workflow pathway and are denoted by boxes defined by dashed lines. At least one step—step A312—is exclusive to the File-Deconvolution Workflow pathway and is denoted by a box defined by a dotted line. Finally, steps A920 and A925, which are depicted by boxes with single solid lines, are optional with regard to the Data-Dependent-Acquisition Workflow but will generally be performed in conjunction with the File-Deconvolution Workflow. The File-Deconvolution Workflow will typically follow the general pathway indicated by dotted arrows at the lower portion of FIG. 14.

Still with reference to FIG. 14, the File-Deconvolution Workflow commences at step A312, in which previously acquired and stored mass spectral data in the form of at least one mass spectrum is input from an electronic storage device and made available for use in subsequent analysis. The mass spectrum may be an $MS^1$ spectrum, an $MS^2$ spectrum or, generally, any form of $MS^n$ spectrum. By contrast, the Data-Dependent-Acquisition Workflow begins at step A310 in which a sample is introduced into a mass spectrometer and is subsequently ionized in step A315. The sample introduction may be from a chromatograph, by means of injection or by other means. An $MS^1$ spectrum of the ions is generated in step A320. It is assumed that steps similar to steps A310, A315 and A320 would have been performed in the generation of the data that is input in the alternative pathway that includes step A312.

In step A325, new peak centroids (i.e., centroids not previously identified during the experiment in question or in a prior $MS^1$ spectrum of the input data); are identified and added to a list of centroids. In the next step A400, the m/z values of the centroids are transformed and the intensity data is converted to a Boolean-valued data array in which bins are assigned over the transformed m/z scale. The step A400 comprises a first substep A420 of constructing and populating a Boolean occupancy array and a second substep A460 of constructing and populating a relative separation matrix (see FIG. 15). The details of these substeps are described in greater detail in a subsequent section of this disclosure.

In step A510, which only applies to the Data-Dependent-Acquisition Workflow, centroids of analytes for which $MS^n$ analysis has been completed are removed from a "selection list" and may be added to an "exclusion list", if mass analysis is being performed on a sample whose composition is time varying, such as upon an effluent from a chromatographic column. The selection list includes one or more mass-to-charge (m/z) values or value ranges which are to be analyzed or which are being analyzed by the mass spectrometer by tandem mass analysis (MS/MS analysis) or possibly by $MS^n$ analysis, each such m/z value or range corresponding to a chemical component of the sample as identified by the methods of the present teachings. The exclusion list includes one or more mass-to-charge (m/z) values or value ranges which are to be excluded from future analysis either for the duration of an experiment or for a temporary time period during the experiment. The temporary time period, if employed, may be determined according to methods of the present teachings, as described in a subsequent portion of this disclosure. Alternatively for direct infusion or flow injection analysis, the one or more mass-to-charge values or value ranges which are to be excluded from future analysis can be performed on signal rank basis. Centroids depicting low-intensity mass spectral lines are removed from the exclusion and selection lists in step A515. The removed m/z values or ranges may be later added to the selection list if the corresponding mass spectral signal intensities subsequently increase during an experimental run.

Figure 18:
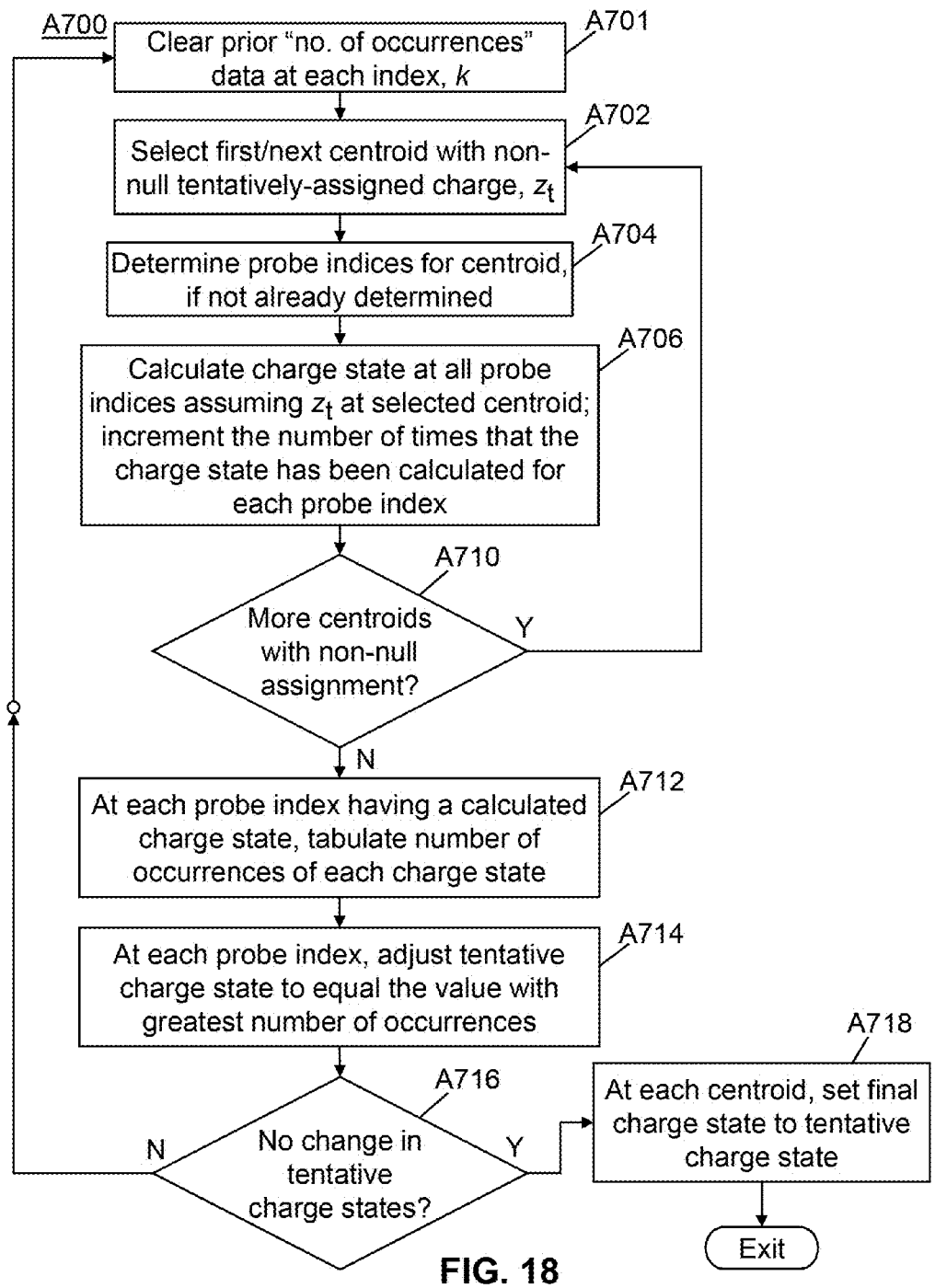
FIG. 18 is a flowchart of a method in accordance with the present teachings for adjusting a set of previously tentatively assigned charge states such that the resulting final assigned charge states are self-consistent.
Figure 19:
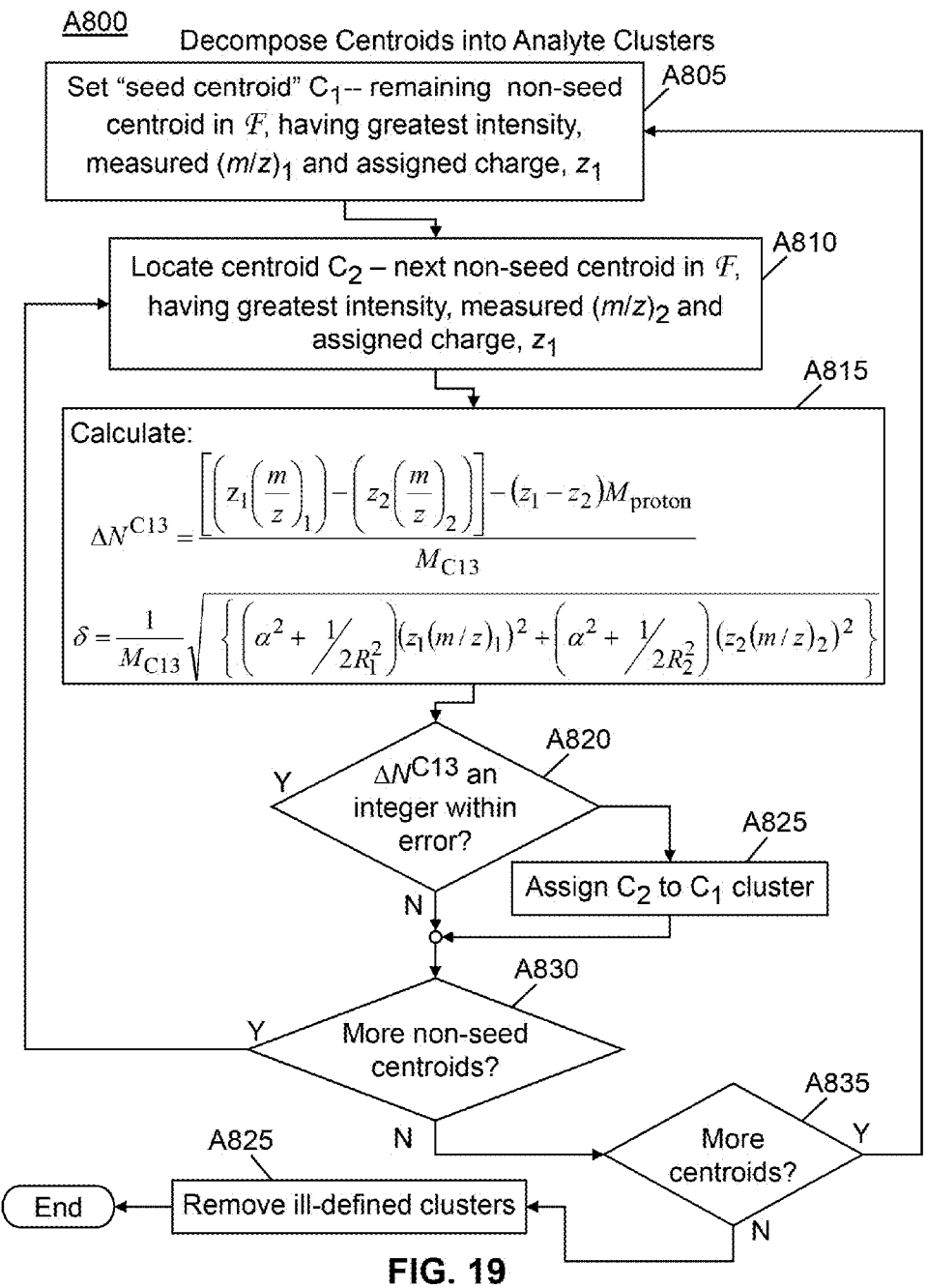
FIG. 19 is a flowchart of a method in accordance with the present teachings for decomposing a set of experimentally determined centroids having assigned charge states into analyte-specific clusters.

In step A600 tentative charge states assignments are made as outlined in FIG. 17 and further discussed below with reference to that figure. Then, in step A700, the tentatively assigned charge states are adjusted and final charge state assignments are made using requirements for self-consistency. The details of this process are outlined in FIG. 18 and further discussed below with reference to that figure. Once the final charge state assignments have been made, the experimentally observed centroids are decomposed into analyte-specific clusters in step A800 using information derived from the spacing of isotopic clusters. The details of step A800 are illustrated in FIG. 19 and described further with reference to that figure.

The execution of the method A300 may branch at step A910 along one of two possible execution paths indicated by solid-line arrows and dotted-line arrows, respectively. If real-time tandem mass spectrometry is being controlled by the results of the prior data analysis, then the method execution may follow the "N" branch (denoted by solid lines) from step A910 directly to step A915, thereby skipping steps A920 and A925. Alternatively, if more data analysis operations are to be conducted upon $MS^1$ data measured in step A320 or if data was previously input in step A312, then the "Y" branch of step A910 is followed whereafter molecular weights may be calculated or analyte species identified (step A920) and the results of the calculations may be reported or stored (step A925). As determined at step A915, if tandem mass spectrometry is to be performed, as will generally be true if the Data-Dependent-Acquisition Workflow execution path is being followed, then the method branches along the "Y" branch to step A930. Otherwise, execution proceeds, along the "N" branch to step A960.

Considering, now, the "online" execution path illustrated on the right-hand side of FIG. 14, a determination is made in step A930 if centroids attributable to known adducts are present in the considered set of centroids. Is so (the "Y" branch of step A930) then the centroids corresponding to adduct species or to otherwise-modified species (for instance, species generated from loss of a neutral molecule) are added to the exclusion list in step A935. Otherwise, step A935 is bypassed. Step A940 is the commencement of top-down analysis in which a representative peak is selected for fragmentation from each of top P analyte-specific clusters determined in step A800. The following steps A945, A950 and A955 are conventional steps of, respectively, isolating ions of the m/z ratios corresponding to the selected centroids, fragmenting the isolated ions and performing a mass analysis ($MS^2$) of the product ions.

Execution of the method A300 may end after step A960, if either the mass spectral experimentation or the data analysis is complete. Otherwise, execution passes back to either step A310 at which the next portion of sample is introduced to the mass spectrometer or to step A312 at which the next portion of mass spectral data is input.

3.2. Building a Boolean-Valued Occupancy Array.

Figure 16:
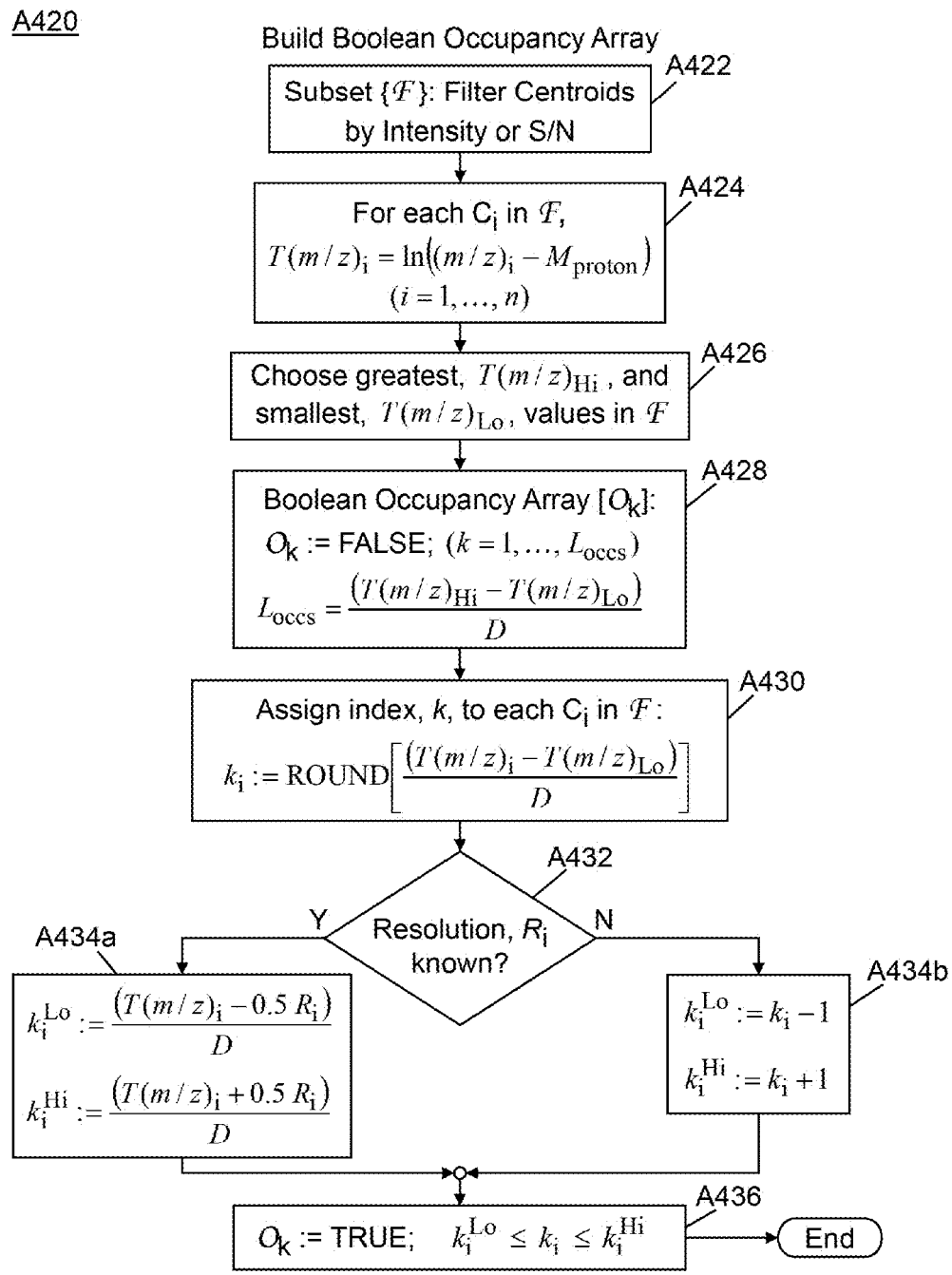
FIG. 16 is a flowchart of a method in accordance with the present teachings for constructing a Boolean occupancy array within a mathematically transformed mass-to-charge space from experimentally determined mass spectral centroid data.

FIG. 16 shows the details of the step A420 of building an occupancy array, $[O_k]$. The values of the array are Boolean variables and the indices of the array correspond to the discretized transformed mass/charge values. The step A420 takes, as input, a collection of centroids, $C_i$ ($1 \leq i \leq L$) where L is an observed number of mass spectral lines. Each $C_i$ is characterized by its mass/charge $(m/z)_i$, its intensity $I_i$, its signal-to-noise ratio $(S/N)_i$ and its resolution $R_i$. Next, a filtering of the centroids is performed (step A422) by collecting the subset $\{\mathcal{F}\}$ of centroids which pass a user settable criterion of intensity and signal to noise thresholds. Next, in step A424, a mass/charge transformation is performed on each $C_i$ in $\{\mathcal{F}\}$ by taking the natural log of the mass/charge value minus that of the mass of a proton, $M_{proton}$ as in Eq. 1.

$$T(m/z)_i = \ln((m/z)_i - M_{proton}) \qquad \text{Eq. (1)}$$

After this transformation, each centroid, $C_i$ in the subset $\{\mathcal{F}\}$ is characterized by $T(m/z)_i$, $I_i$, $(S/N)_i$ and $R_i$. The greatest, $T(m/z)_{High}$, and the smallest, $T(m/z)_{low}$, values of the T(m/z) values from subset $\{\mathcal{F}\}$ are noted in step A426. This information is then used to create the array $[O_k]$ of values, where each element of the array is a Boolean-valued "occupancy" which maintains a record of whether or not a "signal" is deemed to occur at the respective transformed mass-to-charge value, $T(m/z)_k$, associated with the array element. Upon creation, each element, $O_k$, of the array is initialized to the Boolean value "FALSE". The number of discrete elements in the array, or "length" of the array $[O_k]$ is denoted as $L_{occs}$, which is determined as $$L_{occs} = \frac{(T(m/z)_{high} - T(m/z)_{low})}{D} \qquad \text{Eq. (2)}$$

where D is the width of each bin in the array and is $D = MA/10^6$, where MA, typically 10, denotes a user settable parameter of the mass accuracy of the spectrum of interest.

After creation and initialization, the array $[O_k]$ must be populated (performed in step A436) with meaningful values. The elements of the occupancy array $[O_k]$ are indexed by the variable, $k$ ($1 \leq k \leq L_{occs}$) whereas the elements of the filtered centroid subset $\{\mathcal{F}\}$ are indexed by the variable, i. The latter indices are converted into corresponding k-values in step A430, in which, for each centroid, $C_i$, in the subset $\{\mathcal{F}\}$, the corresponding index, $k_i$, is determined as follows:

$$k_i = \frac{(T(m/z)_i - T(m/z)_{low})}{D} \qquad \text{Eq. (3)}$$

and is rounded to the nearest integer (the rounding operation is indicated by the operator "ROUND[ ]" in FIG. 16. If the resolution, $R_i$, of the centroid $C_i$ is available (some spectra such as those collected in the centroid mode, may not have this defined), then the "Y" branch of the decision step A432 is followed, in which the additional indices $k_i^{Lo}$ and $k_i^{Hi}$ are calculated in step A434a as follows $$k_i^{Lo} = \frac{(T(m/z)_i - 0.5(R_i))}{D} \qquad \text{Eq. (4a)}$$

$$k_i^{Hi} = \frac{(T(m/z)_i + 0.5(R_i))}{D} \qquad \text{Eq. (4b)}$$

with values rounded to the nearest integer. In cases in which $R_i$ is not available, these indices are instead set to $k_i - 1$ and $k_i + 1$, respectively, in step A434b. Finally, in step A436, array values are all set to the Boolean value "TRUE" for indices ranging from $k_i^{Lo}$ to $k_i^{Hi}$, namely $$O_k := \text{TRUE}; k_i^{Lo} \leq k \leq k_i^{Hi} \qquad \text{Eq. (5)}$$

3.3. Building a Relative Separation Matrix (RSM).

Figure 15:
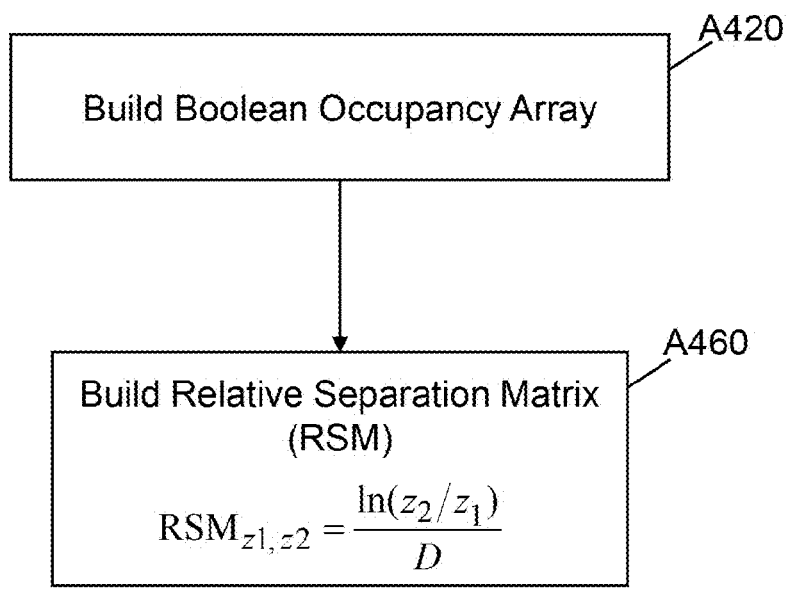
FIG. 15 is a flowchart of a method to convert experimentally measured mass spectral centroids to an occupancy array, with the indices that are related to one another by different charge states encapsulated in a matrix, in accordance with the present teachings.

As shown in FIG. 15, step A460 is the step of constructing a relative separation matrix and is the second sub-step of the general step A400. The creation of a relative separation matrix is motivated by observation that, given two centroids $C_1$ and $C_2$, then, if they belong to the same protein isotopic peak but differ just in charge states, then their mass/charge values are related as $$|z_1| \times ((m/z)_1 - M_{proton}) = |z_2| \times ((m/z)_2 - M_{proton}) \qquad \text{Eq. (6)}$$

in which $z_1$ and $z_2$ are the charge state of the centroids $C_1$ and $C_2$ respectively, and $M_{proton}$ is the mass of a proton. The charge state values, $z_1$ and $z_2$, will generally be either all positive or all negative depending on the mode of ionization used in the mass spectrometer instrument conducting the analyses. Performing the transformation as described in Eq. (1) yields the relationship that $$T(m/z)_1 = T(m/z)_2 + \ln|z_2/z_1| \qquad \text{Eq. (7)}$$

The important property of Eq. (7) is that the transformed $T(m/z)_i$ values at different charge states are related by an additive factor that is independent of the transformed values. Thus one can pre-compute and cache the quantities $\ln(z_2/z_1)$ as a matrix that can be reused in subsequent calculations by simple look-ups by pre-computing the RSM. The absolute values of the charge states will generally range between unity and some maximum value, $|Z_{max}|$ or, more specifically, $1 \leq z_1, z_2 \leq |Z_{max}|$. The last step is to discretize the $\ln|z_2/z_1|$ matrix by dividing by D as in Eq. (4):

$$RSM_{z1,z2} = \frac{\ln|z_2/z_1|}{D} \qquad \text{Eq. (8)}$$

The limits of the matrix, determined by $Z_{max}$, may be set by a user anticipating the maximum and minimum charge states that will be encountered in a set of spectra. Alternatively, $Z_{max}$ may be a pre-determined or pre-calculated value. Typically, the absolute values of the charge states range from 1 to 50 for a top down experiment. So in such a case, RSM will be a 50×50 anti-symmetric matrix.

3.4. Building a Scoring Distribution for Each Centroid and Using it to Assign Tentative charge States.

Figure 17A:
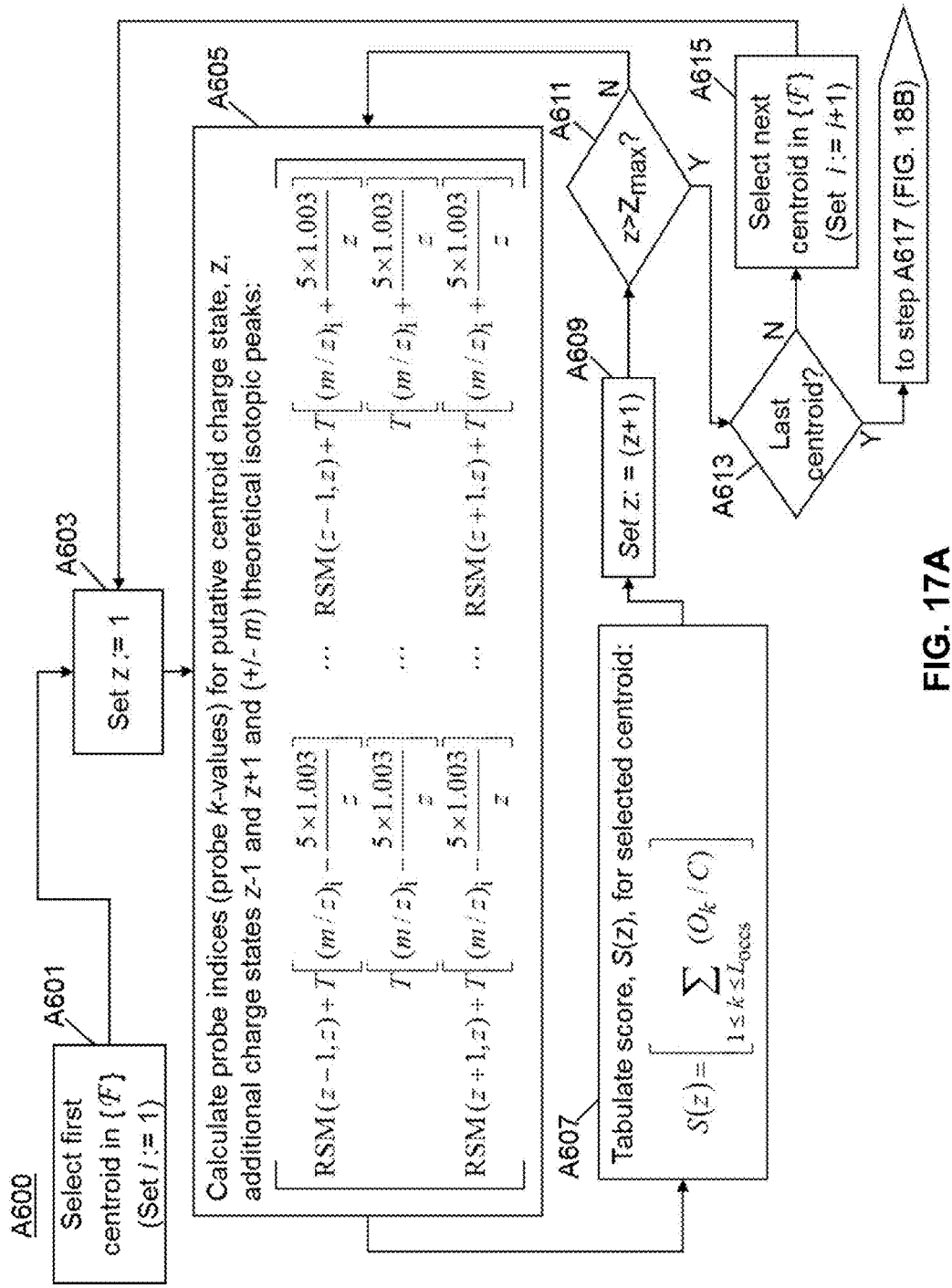
FIG. 17A and continuation
Figure 17B:
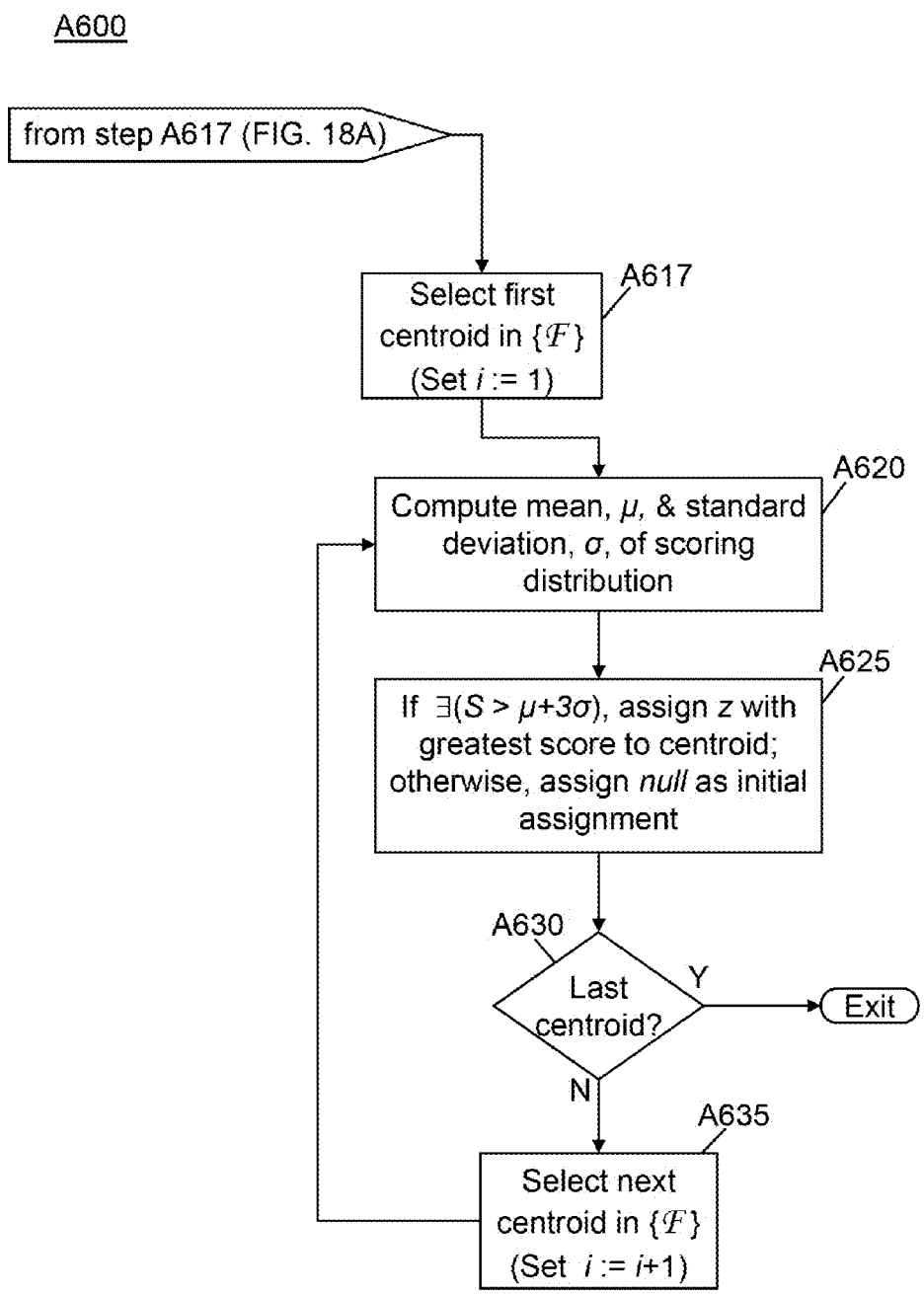
FIG. 17B, is a flowchart of a method in accordance with the present teachings for assigning tentative charge states for a plurality of experimentally determined mass spectral centroids.

Before a self-consistent set of charge assignments may be determined by iteration (in step A700, FIG. 18), a reasonable initial set of tentative charge assignments must be formulated. The step A600, the details of which are shown in FIGS. 17A and 17B, generates this initial set of by assigning a likely charge state to various of the centroids of subset $\{F\}$. Steps A601-A615 consider each such centroid, in turn, and, for each considered centroid, step through various putative values of putative charge state, z, from a minimum charge state value, $Z_{min}$ up to a maximum charge state value, $Z_{max}$. For example, putative charge states from z=1 through z=50 might be considered for each centroid. For each combination of a centroid, $C_i$ (as selected in step A601 or step A615) and a putative charge state $z_i$, (as set in either step A603 of A609), a set of "probe indices" $k_p(C_i, z_i)$ is calculated in step A605. The probe indices are a set of k-values that reference bins of the occupancy array, $[O_k]$, for purposes of testing for "TRUE" values at each of these indices. The $k_p(C_i, z_i)$ matrix includes a first row having the indices corresponding to the discretized $T(m/z)_i$ values of the (+/−m) theoretical isotopic peaks of the selected centroid $C_i$. For example, if m=5, the probe indices corresponding to the (+/−5) theoretical isotopic peaks are the transformed values of:

$$(m/z)_i - \frac{(5)(1.003)}{z},$$
$$(m/z)_i - \frac{(4)(1.003)}{z}, \ldots, (m/z)_i + \frac{(5)(1.003)}{z}$$

The $k_p(C_i, z_i)$ matrix also includes two additional rows, the elements of which are calculated by generating, for each of the 2m probe indices in the row described above, an additional probe index corresponding to expected location of the z−1 peak and another additional probe index corresponding to the expected location of the z+1 peaks. Specifically, the indices $[k_p(C_i, z_i) + RSM(z_i-1, z_i)]$ and $[k_p(C_i, z_i) + RSM(z_i+1, z_i)]$ are generated, where RSM is the pre-computed and cached relative separation matrix described above. Note that the $k_i$ index of the centroid $C_i$, itself, is excluded from the probe indices matrix because, at this stage of execution of the algorithm, it is given that the occupancy array contains a value of "TRUE" at such index. Similarly, one can also increase the probe matrix in include more charge states of (z−m, z−m+1, ..., z+m−1, z+m) instead of just (z−1, z, z+1) as described above.

In step A607, a score value is calculated for each tested z value and each centroid $C_i$. The set of scores is used to generate a scoring distribution for each z value. Each score S(z) is calculated by summing, for each possible value of $z_i$, the experimentally-derived occupancy values. Specifically, the score for each value of z is determined by $$S(z) = \Sigma O_k / C \qquad \text{Eq. (9)}$$

where the sum is over k of $k_p(C_i, z_i)$ such that $(1 < k < L_{occs})$ and C is just the number of such k's. In other words, the score at z is just the fraction of $k_p(C_i, z_i)$ indices that are "occupied" by a measured above-threshold mass spectral signal (i.e., a value of "TRUE") as coded in occupancy array constructed in step A420 (FIG. 15). Thus, the calculation in step A605 is a form of streamlined approximate "inner product" calculation, with the greatest possible score of any single calculation being unity. The score distribution is formed by summing the scores for each value of z from the lowest to the highest user settable limits. Using our example of 1 and 50 as the low and high limits, we will end up with a distribution of 50 scores for each centroid.

Decision step A611 determines, for each centroid, if the maximum value of z has been considered. If not then execution returns to step A605 for calculation of probe indices with a new value of z (as set in step A609). Otherwise, execution branches to decision step A613 which determines if the last centroid in the subset $\{\mathcal{F}\}$ has been considered. If not, then execution proceeds to step A615 in which the next centroid is selected and then to step A603 in which the z-value is reset to its initial state. Otherwise, execution proceeds to step A617 (FIG. 17B) at which the process of formulating tentative charge assignments is begun.

Steps A617-A635 shown in FIG. 17B illustrate the process of making tentative charge assignments using the scoring distributions previously generated in multiple iterations of step A607 (FIG. 17A). In step A617, the first centroid is selected; later the choice of centroid being considered is updated in step A635. After either of these two steps, the mean, μ, and standard deviation, σ, of the respective scoring distribution is computed in step A620. Thus, repeated iteration of steps A620-A635 causes these statistical measures to be computed for the scoring distribution associated with each centroid. In step A625, if there are any scores larger than mean μ+3σ, then the z-value with the largest score is assigned to the centroid as the initial charge-state assignment. If there are no scores larger than μ+3σ, then a null value as provided as the initial assignment for the centroid in question.

3.5. Achieving Optimality of Completely Self Consistent Charge Assignment by Iteration.

After the tentative charge-state assignments have been made in step A600, execution of the method A300 (FIG. 14) proceeds to step A700 in which the tentative charge state assignments are adjusted. Details of the step A700 are shown in FIG. 18. The optimal condition is simply defined to be most consistent assignment of charges of all centroids of the spectra. Underlying this condition is the reasoning that the charge state assigned to each centroid should be consistent with those assigned to other centroids in the spectrum.

The details of the step A700 shown in FIG. 18 implement an iterative procedure to generate the charge state assignments as guided by the above optimality condition. Each centroid with a non-null assignment (as assigned in step A625 of FIG. 17B) is considered, in turn. Each of these may be associated with a set of probe indices as indicated in step A605 of FIG. 17A. This process is repeated for all centroids with a non-null assignment, and a new charge state distribution is determined at each probe index. Specifically, in step A702, the first or next centroid having a non-null tentatively assigned charge state, $z_t$, is selected. In step A704, the probe indices for the centroid in question are generated, as previously described with respect to step A605 of FIG. 17A, if necessary. Then, in step A706, a charge state is calculated at each of the probe indices corresponding to the centroid in question, assuming that the charge state of the selected centroid is $z_t$. For each probe index, a record is kept of how many times each charge state is calculated for that probe index. Before beginning each loop through steps A702-A710, these records are cleared (re-set zero) in step A701. Thereafter, during each loop, each time that a charge state is calculated for a probe index in step A706, the number of times that the charge state has been so calculated at that probe index is incremented. If, at step A710, there are additional centroids with a non-null assignment, then execution returns to step A702 and the next such centroid is selected.

After the last centroid has been considered, execution branches to step A712. In step A712, the number of occurrences of each charge state (as calculated in step A706) are tabulated at each probe index, thereby generating a charge state distribution for each probe index. Using the new charge-state distributions, a "charge assignment by majority" (CAM) is obtained in step A714 by adjusting tentative charge state at each probe index so at to equal the charge state with the highest number of tabulated at the respective index. The set of all such CAM charge assignments forms an array of values—the charge assignment by majority array.

The charge assignments are considered to be inconsistent if, at step A716, the values of the CAM array differ from the charge-state values used in the generation of the CAM array. By contrast, a completely self consistent charge assignment is defined as the assignment of charge at each index such that it is in complete concordance with that from the CAM array resulting from it. Thus, at step A716, the adjusted tentative charge states are compared to their prior values. If there has been a change that is greater than a certain tolerable limit, then the charge assignments are not self-consistent. In this case, the "N" branch of step A716 is followed and execution returns to step A701 whereby a new set of calculations are performed so as to achieve self consistency. Thus, a set of repetitions of the CAM array determination are performed by using the charges from each CAM to generate a subsequent CAM. Optimality is achieved when convergence is achieved—that is, the CAM generates the same CAM.

In practice, one might not achieve exact convergence by this procedure. However, the inventors' experience shows that, after a few iterations, the incidence of non-concordance becomes negligibly small and thus one can stop the iteration at a very good charge-state assignment. Accordingly, in step A716, convergence is considered to be operationally achieved when the difference in successive CAM arrays is within a certain tolerable limit (i.e., within a certain tolerance). In this case, execution branches to step A718 at which the final self-consistent charge state and each centroid is set to be equal to the tentative charge state at which the operational convergence occurred.

4. Determination of Analyte-Specific Clusters

The clustering approach starts with the clustering criterion defined by Eq. (10), in which the number of $C^{13}$ non-monoisotopic peaks, $\Delta N^{C13}$, that are reasonably expected to occur within a restricted m/z range is given by $$\text{Number of } C^{13} \text{ Peaks} = \frac{[(z_1(m/z)_1) - (z_2(m/z)_2)] - (z_1 - z_2)M_{proton}}{M_{C13}} \quad \text{Eq. (10)}$$

in which $z_1$ and $z_2$ are the charge states assigned to mass spectral lines, $(m/z)_1$ and $(m/z)_2$ are the experimentally measured mass to charge values, $M_{C13}$ is the mass difference between the isotopes of carbon, $C^{13}$ and $C^{12}$, and $M_{proton}$ is the mass of a proton. The error ($\delta$) or standard deviation associated with the calculation is computed from a user-supplied value of accuracy, $\alpha$, which is defined in ppm, as well as the resolutions $R_1$ and $R_2$ of the centroids under consideration as described in Eq. (11)

$$\delta = \frac{1}{M_{C13}} \sqrt{ \begin{cases} (\alpha^2 + 1/2R_1^2)(z_1(m/z)_1)^2 + \\ (\alpha^2 + 1/2R_2^2)(z_2(m/z)_2)^2 \end{cases} } \quad \text{Eq. (11)}$$

To determine if any two centroids (peaks) belong to the same analyte-specific cluster (associated with a particular biomolecule such as a protein), the theoretical $\Delta N^{C13}$ value is calculated using Eq. (10). If the calculated $\Delta N^{C13}$ value is an integer within the measurement error, as computed as in Eq. (11), then the two centroids are considered to belong to the same analyte-specific cluster, provided that the number of $C^{13}$ peaks does not exceed a user defined limit (typically 10 to 15). Of course, one skilled in the art can easily use a multitude of other similar statistical tests such as the z-test, or t-test to determine whether the two peaks differ by an integral number of $C^{13}$, given the uncertainties of their m/z's as encoded in $\alpha$ and the resolution R's.

The step A800 of decomposing the mass spectral lines into analyte-specific clusters shown in FIG. 19 makes use of the above reasoning. The step A800 considers centroids for which charge assignments have been made, as previously described. Step A805 begins with the charge-assigned centroid that has the greatest experimentally-observed intensity. The so-selected centroid is then uses as a "seed" for the first cluster. Then, proceeding in order of decreasing intensity (steps A810 through A830), a check is made to determine if the next centroid in the list clusters with the seed centroid of this cluster. This check is performed by first calculating $\Delta N^{C13}$ and its error, $\delta$, using Eq. 10 and Eq. 11, respectively (step A815). If it is noted, in the decision step A820, that the presently-calculated value of $\Delta N^{C13}$ is an integer, within the calculated error, then execution follows along the "Y" branch to step A825 in which the centroid under consideration is grouped together with the seed centroid as belonging to a single cluster. If not, then the "N" branch is followed such that, in step A830, if there are remaining non-seed centroids, execution returns to step A810 in which the next-intense non-seed centroid is selected for cluster checking. If, at step A830, the list of non-seed centroids is exhausted (that is, there are no remaining non-seed centroids having intensities less than the presently considered centroid) but there are remaining non-clustered centroids (determined in step A835), then execution returns to step A805 in which a new cluster is started with using the most-intense non-seed centroid as the new seed. Subsequent iterations check against all cluster seeds created and create new clusters if the new centroid does not cluster with any preceding clusters.

Finally, in step A840, a simple heuristic is employed to determine if any cluster created by the clustering algorithm is "healthy". In our initial implementation, we use the simple rule that a "healthy" cluster must have at least four distinct charge states or at least N (user settable, but defaulting to 15) member centroids. We filter out clusters that are not "healthy" according to these criteria. After the removal of "unhealthy" clusters, the remaining are the final analyte-specific clusters, each representing a different bio-polymer or other high-mass compound.

5. Protein Molecular Weight Calculations

One of the more common ways of calculating the monoisotopic molecular weight, $M_{mono}$, of a protein from an experimental high-resolution spectrum is to use the so-called "Averagine" method (Senko, M. W, Beu, S. C. and McLafferty, F. W., 1995, Determination of monoisotopic masses and ion populations for large biomolecules from resolved isotopic distributions. J. Am. Soc. Mass Spectrom., 6: 229-233), which itself is an extension of an earlier method for low-resolution data (Zubarev, R. A. and Bonddarenko, P. V., 1991, An a-priori relationship between the average and monoisotopic masses of peptides and oligonucleotides. Rapid Commun. Mass Spectrom., 5: 276-277). Briefly, the Averagine method first models an experimental isotopic cluster by a hypothetical model molecule—the "Averagine" molecule. By optimizing the fit between the experimental and the theoretical isotopic distribution, one can arrive at an estimate of the mono-isotopic mass desired.

The Averagine technique is used within various mass spectrometry peak decomposition and analysis algorithms that are commercially available from Thermo Fisher Scientific of Waltham Mass. USA. Although the Averagine method has been highly successful, the present inventors are motivated to develop a different approach based on the following considerations: (1) Calculation speed. Averagine fitting may be time consuming, a not insignificant consideration for real-time applications, such as those described herein in which decisions are automatically made, in real time, regarding which of several observed ions to fragment. It should be noted, however, that, in situations where a large number of spectral fits are not required, calculation speed may not pose any concern; and (2) Mass accuracy. For a larger molecular weight protein whose signature appears in a crowded spectrum, the corresponding isotopic cluster tends to be noisy and incomplete (missing isotopes—especially the edges, missing charge states etc). The use of an Averagine fit may not be appropriate in such instances.

The present inventors therefore here teach an approach that promises to produce a robust estimate of the mono-isotopic mass that is very easy to calculate and more resistant to noise and artifacts. The main goal is robustness and precision, accepting the compromise that the estimate might be biased. In short, the estimate might not be the "true" mono-isotopic mass (but nonetheless very close to it), but it should be robust/stable in face of experimental imperfections. The error should deviate from the true mono-isotopic mass by either 0 or +/−1 dalton (1 Da) precisely, after taking mass accuracy into consideration. The inventors here point out that robustness, in many cases, is more important than accuracy. For example, if one were to build a molecular weight database based on experimental data, the ability to produce the same answer both while building the database and while testing the database by new data is generally desired, even if the estimates are potentially off by 1 Da from the true molecular weight but nonetheless are identical from experiment to experiment.

The approach starts with three simple observations: (1) the isotopic patterns for most proteins are due to the $C^{12}/C^{13}$ binomial distribution and all the other isotopes are of too low an abundance to warrant consideration; (2) the mode (i.e., the peak having the greatest intensity) of a binomial distribution is a very robust feature of the binomial distribution compared to either the average, the standard deviation, or the exact boundaries of the distribution, and (3) for the binomial distribution, the mode is located less than 1 Da to the left of the average (see Table A1, which is presented in FIGS. 20A-20D). This means that the mode is a very usable replacement for the average, which itself is more difficult to estimate for more noisy data. For example, a distribution truncated at the edges will give rise to an unreliable average estimate while the mode, unless the distribution is highly distorted, is very stable against such truncations.

The starting point for the calculation is defined by M, the observed mode of an isotopic cluster. Zubarev's approach to calculate the first approximation of the monoisotopic mass is then employed where:

$$M_1 = \overline{M} \times 0.999316 \qquad \text{Eq. (12)}$$

The second approximation of the monoisotopic mass is then defined by:

$$M_2 = \overline{M} - n \times 1.003 \qquad \text{Eq. (13)}$$

where n is the smallest integer such that $M_2 \geq M_1$. Finally, in the calculation of the monoisotopic mass, $M_{mono}$, if there is an experimental peak of the cluster which is within 1 Dalton greater than $M_2$ then:

$$M_{mono} = M_2 + 1.003 \qquad \text{Eq. (14a)}$$

otherwise, $$M_{mono} = M_2 \qquad \text{Eq. (14b)}$$

This method of calculating the mono-isotopic mass has been incorporated in the results illustrated herein. The inventors' results show that the predictions compare very favorably to those predicted by the Averagine method. For large proteins, testing on standard proteins indicates that the mono-isotopic mass estimate is stable. In addition, a cluster molecular weight is also calculated for closely related peaks or proteoforms. We term the result of such a calculation as the "Cluster Molecular Weight". After all the proteoforms have been discovered in a batch, a cluster analysis of all the proteoforms is performed using the more discriminatory error function:

$$\text{Error} = \min|w_1 - w_2 - N \times 1.003| \qquad \text{Eq. (15)}$$

over $-3 \leq N \leq 3$. If Error<0.5 $(w_1+w_2) \times 10$ ppm, then $w_1$ and $w_2$ should be considered equivalent. Each proteoform will then be mapped into clusters of equivalent proteoforms represented by a consensus monoisotopic mass. This mass is termed and stored as "consensus MW".

6. Program Input and Output

Figure 21A:
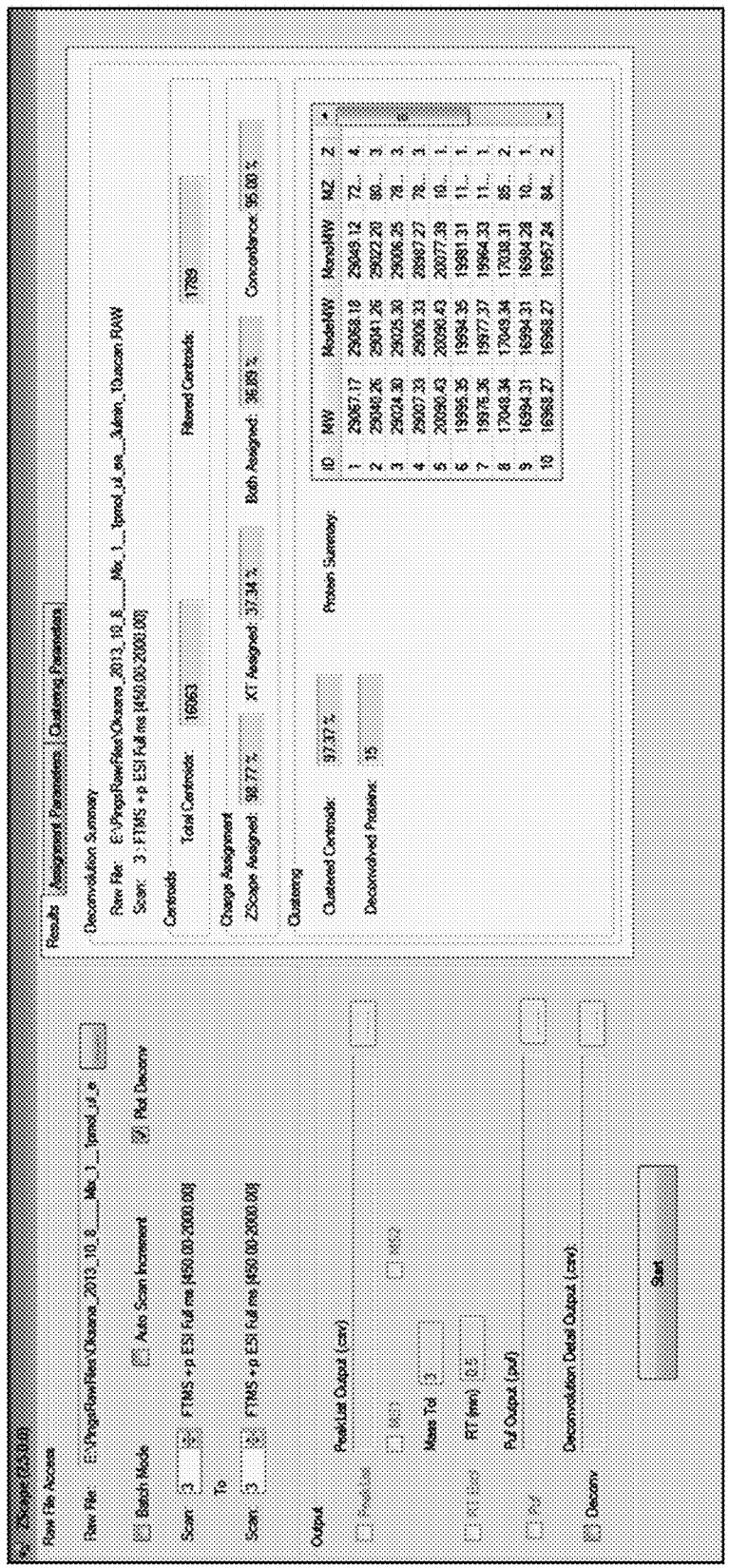

FIG. 21A shows the starting page (i.e., a visual display screen capture) of a post-data-acquisition version of a computer program that employs the data dependent methods described herein. On the left hand side of the display illustrated in FIG. 21A, the "Raw File" box serves as the input line for the mass spectrometry data file to be processed. The "Batch Mode" check box can be enabled, thereby allowing a user to process multiple data files, while the "Auto Scan Increment" check box is used to enable processing of consecutive spectra. Results from the post-data-acquisition version of the program can be plotted in a display by the user enabling the "Plot Deconv" check box. The minimum and maximum spectrum (scan) number to process is set by the "Scan buttons" which directly default to the file length (in scans) or which can be set by the user.

Figure 21D:
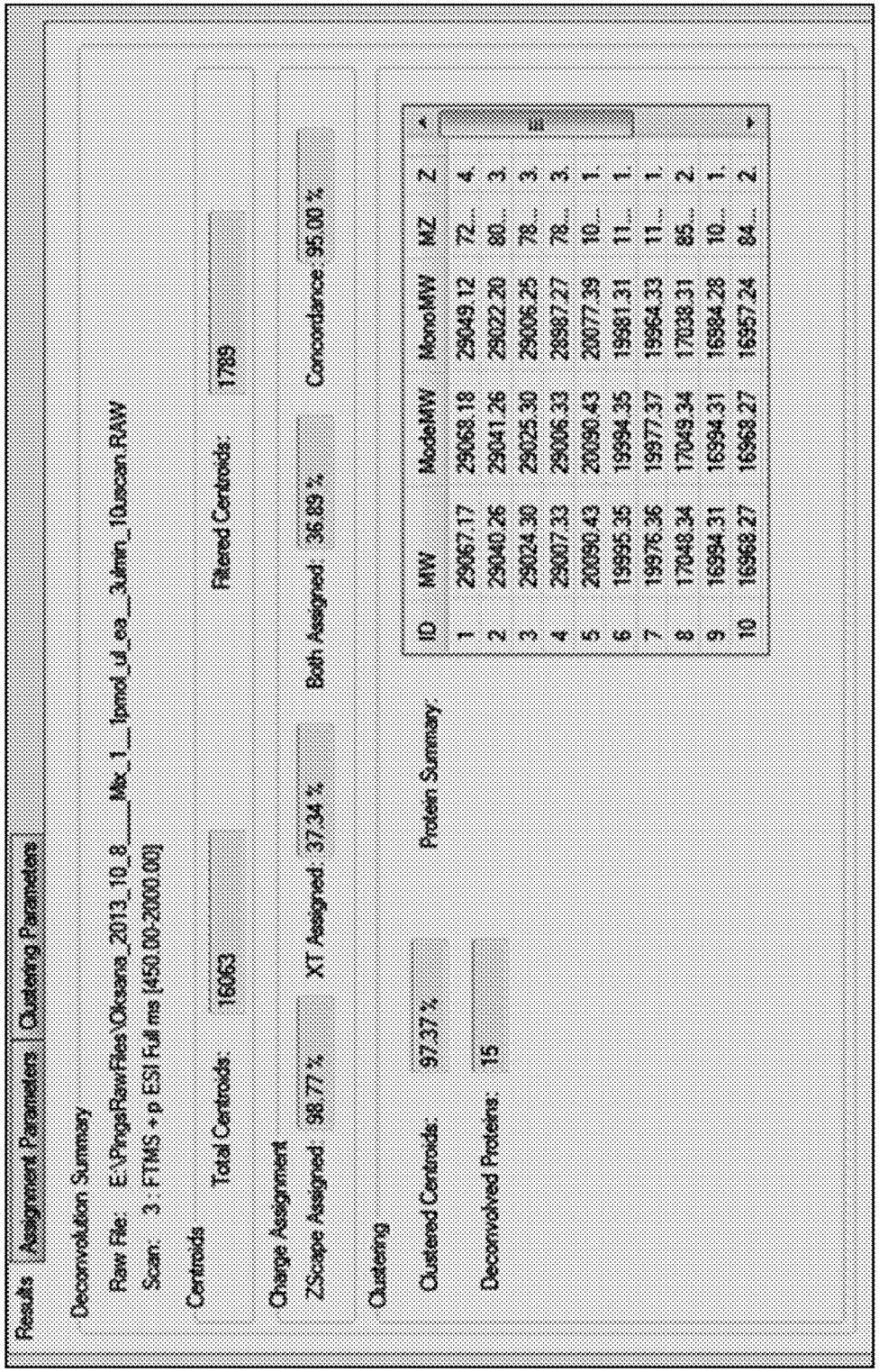

Output can be controlled as seen in the lower left hand side of FIG. 21A, by causing results to be output to a peak list and by the user specifying the output as either MS1 or MS2 type data (in csv file format). The mass tolerance (Mass Tol) defaults to 3; however this too can be set by the user. Output can also be produced in a .puf file format for input into the ProSight™ PC protein identification program. Details of the spectral decomposition results (also referred to herein as "deconvolution" results) can also be stored in a .csv file format for further data analysis. The deconvolution summary in the "Results" tab lists the data file(s) and scan(s) analyzed to produce the report. Moving down the tab are the total number of centroids detected along with the number filtered as part of the program. The percentage of peaks successfully receiving charge-state assignments is found in the "Zscape" box along with a comparison to results as calculated by one of the leading existing deconvolution programs currently used by those skilled in the state-of-the-art. The "both assigned" and "concordance" boxes measure the agreement between the two programs. Moving to the bottom of the "Results" tab, the percentage of cluster assigned and the total number of unique proteins deconvoluted are shown. An expanded view of this tab is shown in FIG. 21D.

Two of the tabs located on the right hand side of the display shown in FIG. 21A provide for choosing the assignment and clustering parameters associated with the deconvolution process. In FIG. 21B, the "Assignment Parameters" tab includes the mass accuracy in parts per million (ppm), the minimum peak intensity threshold, the minimum signal-to-noise ratio (s/n) needed, and the lowest and highest charge state expected for the deconvolution process. These parameters are further divided into two columns one each for $MS^1$ and $MS^2$ analysis.

The "Clustering Parameters" tab shown in FIG. 21C is also divided into two columns relating to $MS^1$ and $MS^2$ analysis respectively. Provision is made for user input of the minimum number of contiguous charge states and isotopes for the clustering convergence calculation described above. The "Sufficient Contiguous Charge States", "Sufficient Contiguous Isotopes" and "Mass Separation" parameter input displays are also present on this input tab.

7. Examples

Figure 22A:
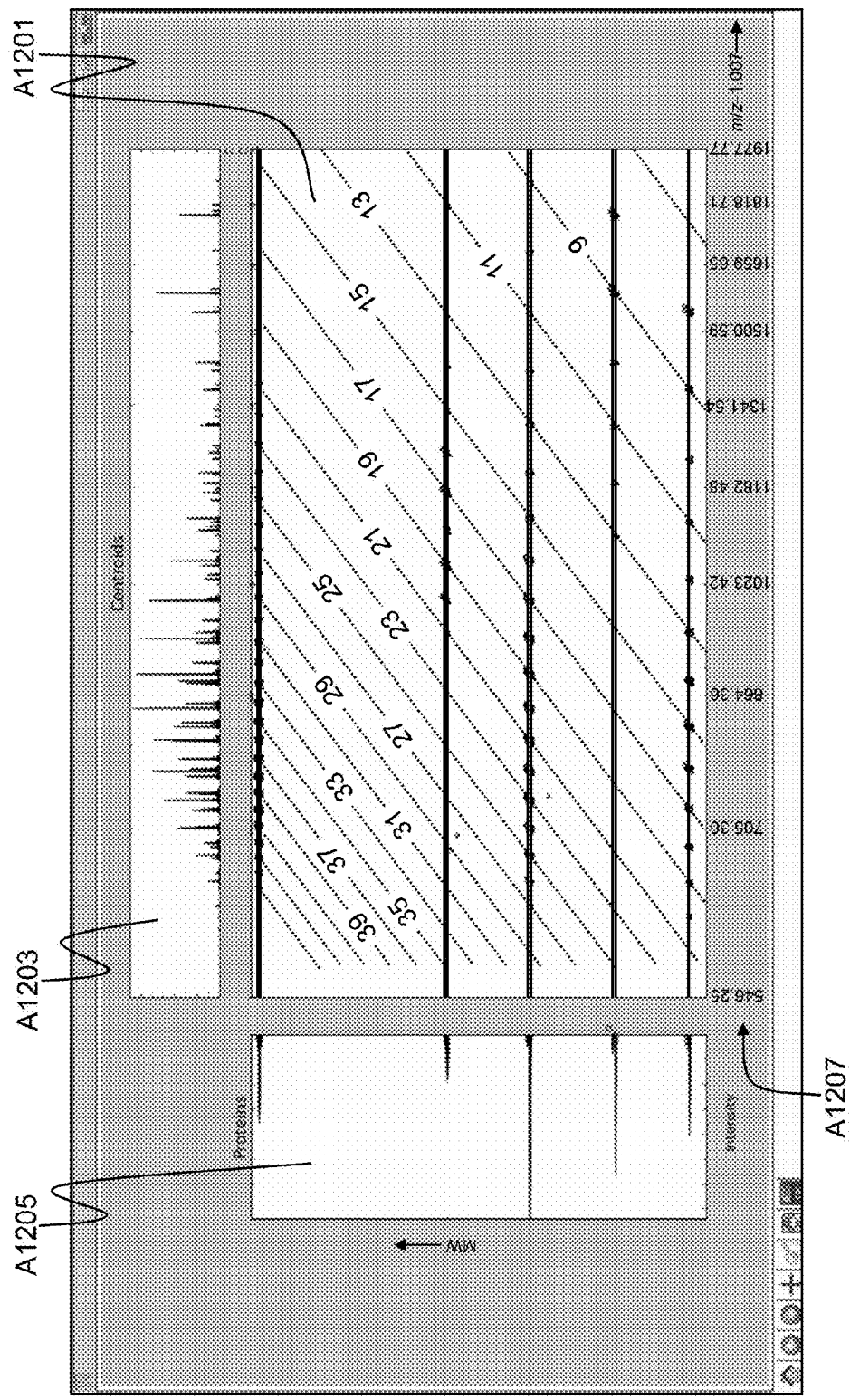
FIG. 22A is a depiction of a computer screen information display illustrating peak cluster decomposition results, as generated by computer software employing methods in accordance with the present teachings, calculated from a mass spectrum of a five-component protein mixture consisting of cytochrome-c, lysozyme, myoglobin, trypsin inhibitor, and carbonic anhydrase.
Figure 22B:
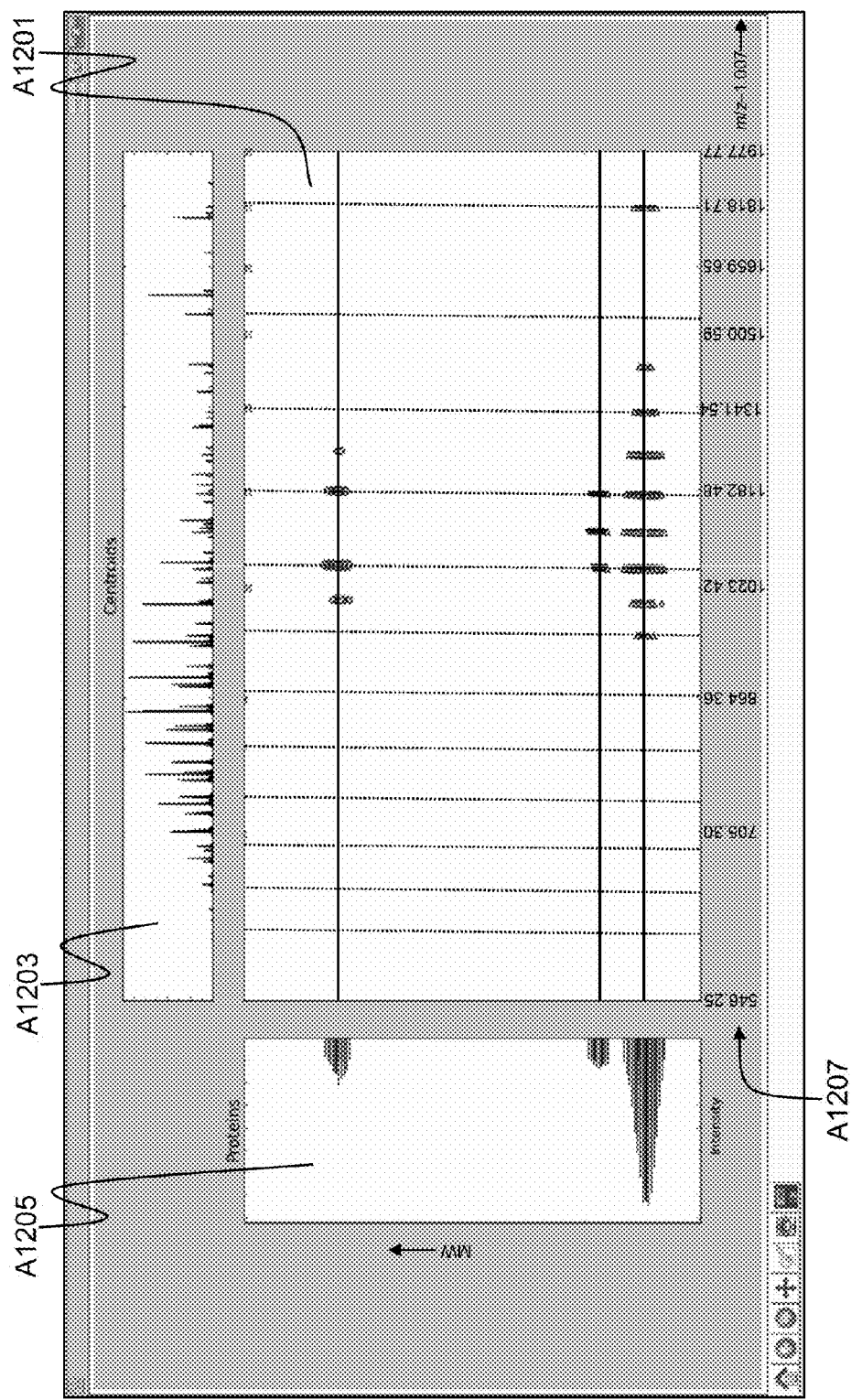
FIG. 22B is a depiction of a computer screen information display illustrating peak cluster decomposition results, as generated by computer software employing methods in accordance with the present teachings, the display illustrating an expanded portion of the decomposition results shown in FIG. 22A.
Figure 22C:
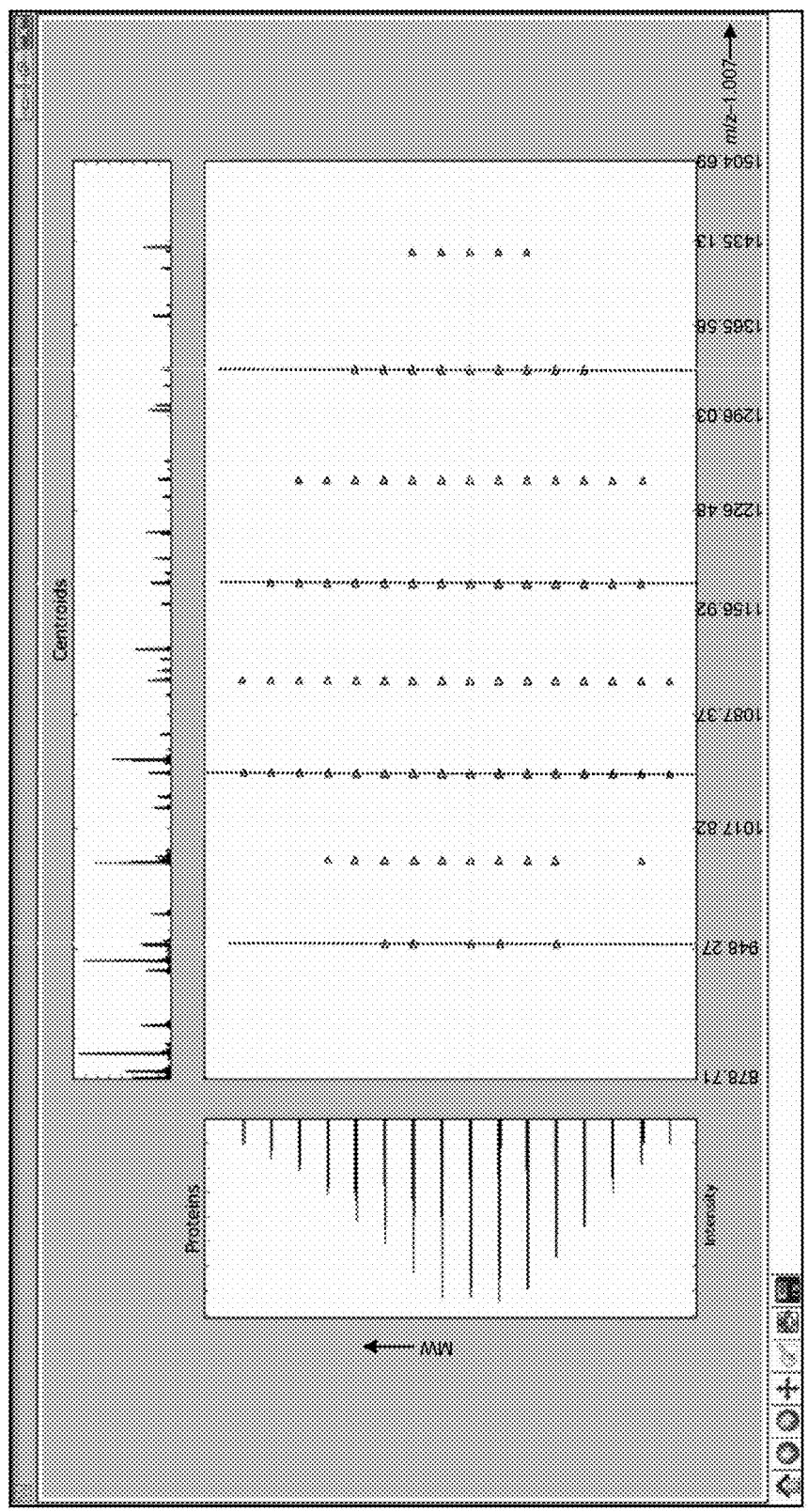
FIG. 22C is a depiction of a computer screen information display illustrating peak cluster decomposition results, as generated by computer software employing methods in accordance with the present teachings, the display illustrating an even-further expanded portion of the decomposition results shown in FIG. 12B.

FIG. 22A shows the deconvolution result from a five component protein mixture consisting of cytochrome c, lysozyme, myoglobin, trypsin inhibitor, and carbonic anhydrase. A top display panel A1203 of the display shows the acquired data from the mass spectrometry represented as centroids. A centrally located main display panel A1201 illustrates each peak as a respective symbol. The horizontally disposed mass-to-charge (m/z) scale A1207 for both the top panel A1203 and central panel A1201 is shown below the central panel. The computer display may also include (not specifically shown in FIG. 22A) the settings for mass accuracy (expressed in ppm), the peaks/isotope cluster setting, the minimum intensity threshold and signal-to-noise settings, and the minimum and maximum charge states associated with the calculation. The panel A1205 on the left hand side of the display shows the calculated molecular weight(s), in daltons, of protein molecules. The molecular weight (MW) scale of the side panel A1205 is oriented vertically on the display, which is perpendicular to the horizontally oriented m/z scale A1207 that pertains to detected ions. Each horizontal line in the central panel A1201 indicates the detection of a protein in this example with the dotted contour lines corresponding to the ionic charge states, which are displayed as a direct result of the transformation calculation discussed previously. In FIG. 22B is shown a display pertaining to the same data set in which the molecular weight (MW) scale is greatly expanded with respect to the view shown in FIG. 22A. The expanded view of FIG. 22B illustrates well-resolved isotopes for a single protein charge state (lowermost portion of left hand panel A1205) as well as potential adduct or impurity peaks (two present in the display). The most intense of these three molecules is that of trypsin inhibitor protein. A further-expanded view in FIG. 22C shows the exact detail of the trypsin inhibitor protein at the isotopic level. The symbol size used to represent the individual isotopes is scaled according to the intensity of each isotope peak.

Figure 23A:
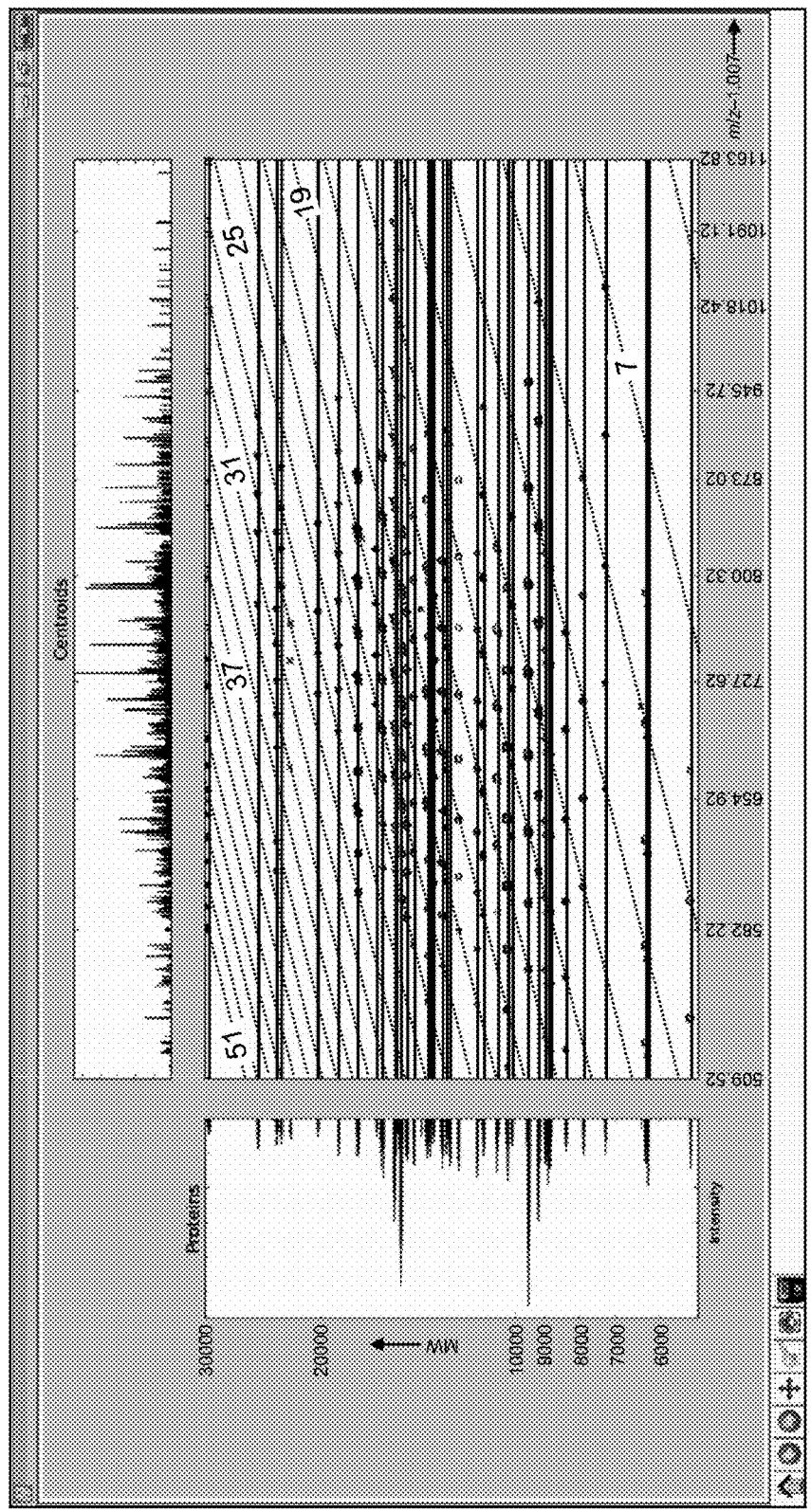
FIG. 23A is a depiction of a computer screen information display illustrating peak cluster decomposition results, as generated by computer software employing methods in accordance with the present teachings, the display illustrating peak cluster decomposition results calculated from a single-stage mass spectrum of a crude extract from the bacterium *E. coli* directly infused into a mass spectrometer.
Figure 23B:
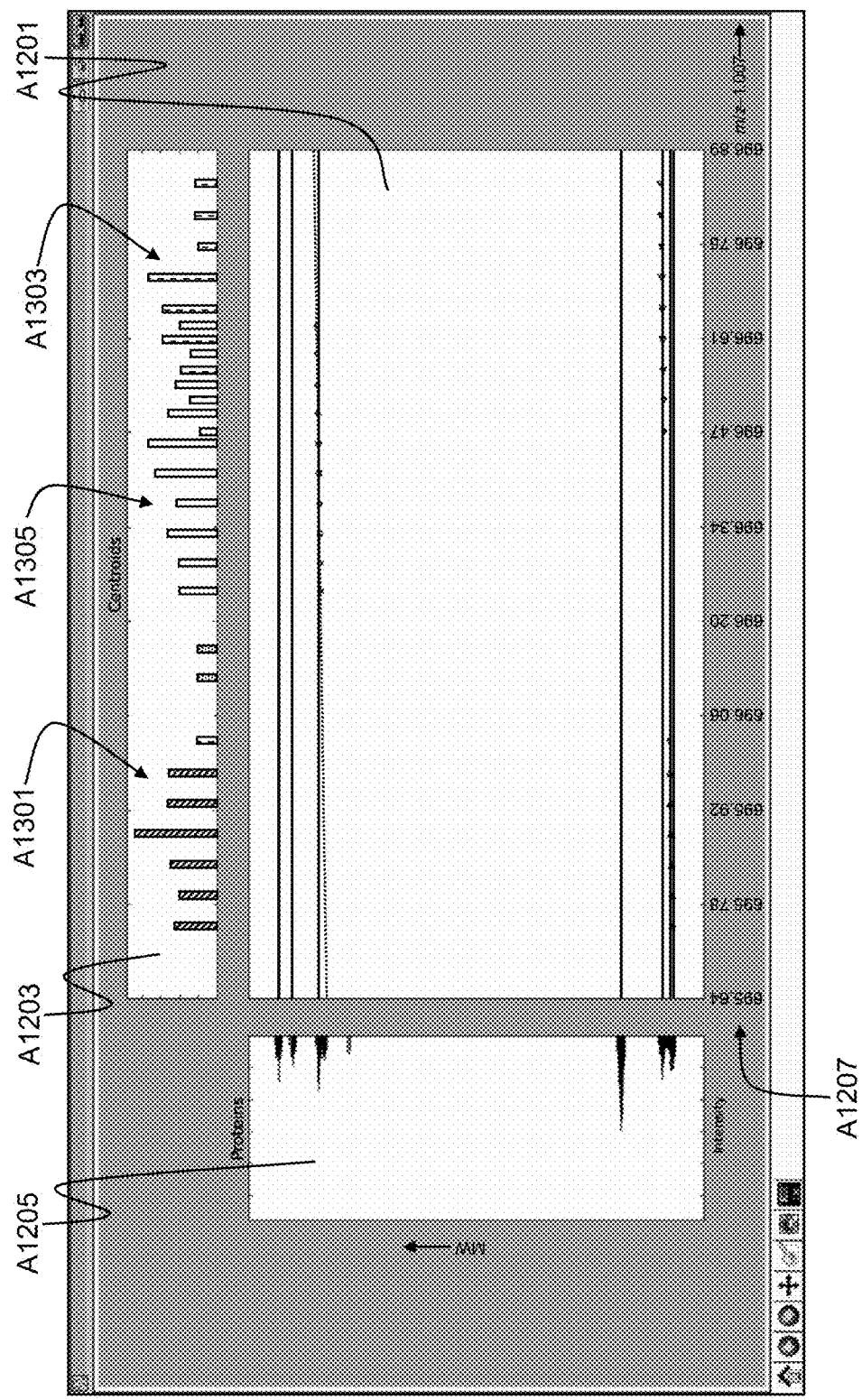
FIG. 23B is a depiction of a computer screen information display illustrating peak cluster decomposition results, as generated by computer software employing methods in accordance with the present teachings, the display illustrating an expanded portion of the decomposition results shown in FIG. 23A.
Figure 23C:
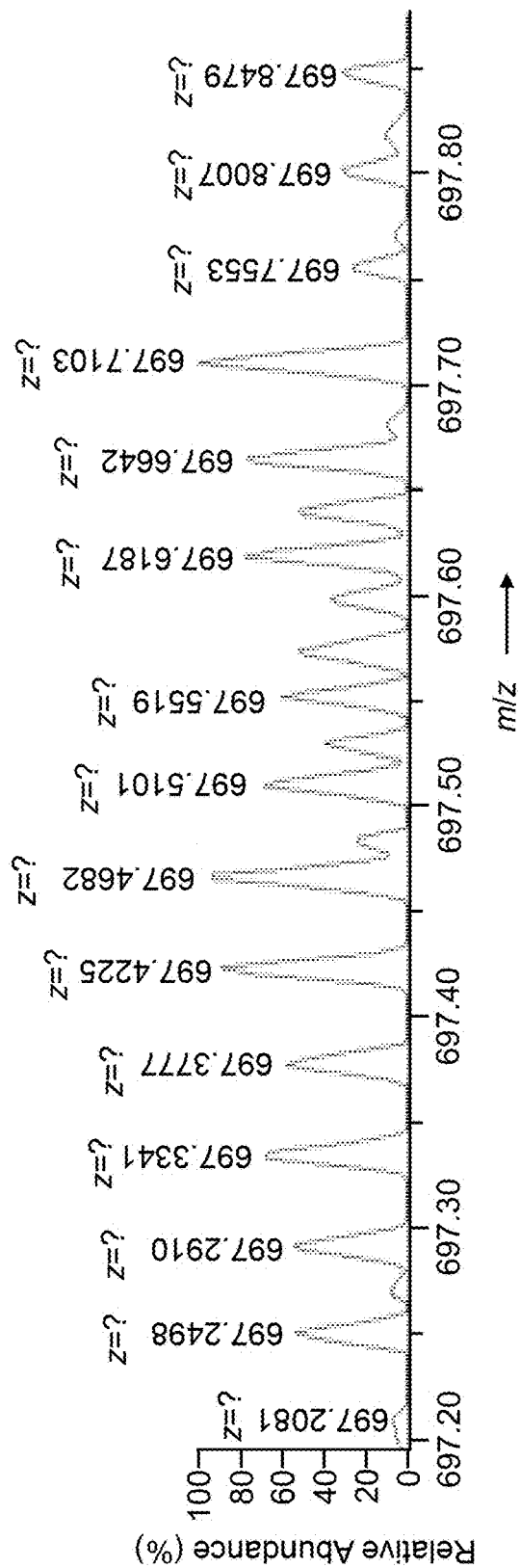
FIG. 23C is a depiction of the mass spectral data whose peak cluster decomposition is shown in FIGS. 23A-23B, showing peak positions and charge-state assignments as provided by a conventional mass spectral peak analysis computer program.
Figure 23D:
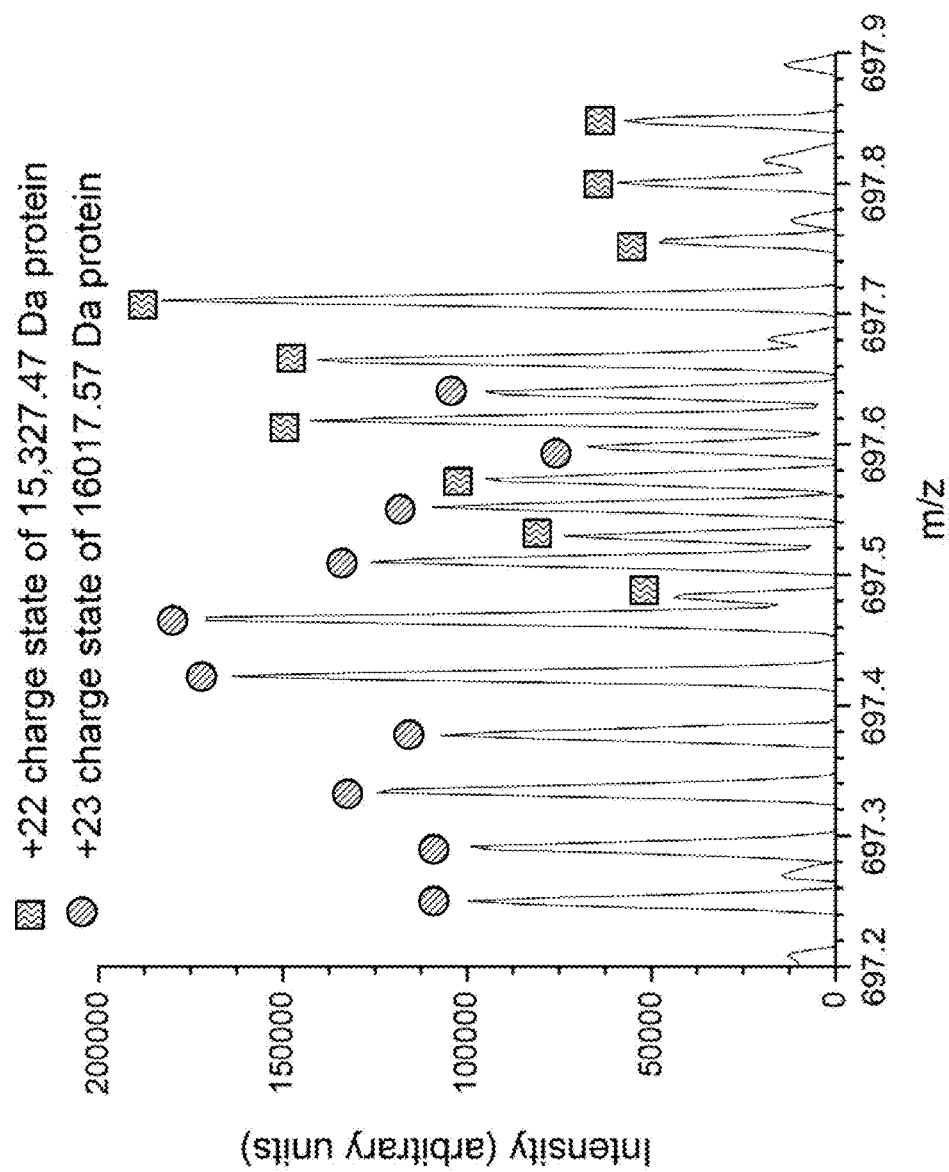
FIG. 23D is a depiction of the mass spectral data whose peak cluster decomposition is shown in FIGS. 23A-23B, showing charge-state assignments as provided by methods in accordance with the present teachings.

FIG. 23A shows the data and deconvolution results of a crude extract from the bacterium *E. coli*. This sample was directly infused into the mass spectrometer using only a single stage of mass spectrometry. The calculated results, obtained using methods in accordance with the present teachings, indicate the presence of 58 unique discernable proteins in this sample. Many of the proteins in this example have overlapping charge states which are easily clustered using the aforementioned algorithm. FIG. 23B illustrates another display corresponding to the same data set showing an expanded view of the m/z scale in the vicinity of m/z=700 Da/e (as well as an expanded view of the MW scale in Daltons) showing three distinct charge states depicted by differently patterned centroids in the top panel A1203. The centroids A1301 in the top panel A1203 of the display correspond to a +22 isotopically resolved charge state of a protein of mass 15,305.76 Da. In this case, this is the only charge state distribution present, yet the algorithm correctly identifies the cluster even though the centroid bars A1303 and A1305 occur within 1 Da of the charge state in question. Many currently available deconvolution programs cannot correctly assign charge state to independent distributions (two different proteins) within a 3 Da window. Also, the centroid bars A1305 represent the +23 charge state of a protein from *E. coli* of mass 16,017.57 Da. Note that the +23 charge state of this protein directly overlaps with the centroid bars A1303 of a separate +22 charge state protein of mass 15327.47 Da. Typical deconvolution programs are unable to correctly assign peaks in spectra having this kind of closely spaced or overlapping charge states as can be seen by comparison to FIG. 13C, which shows the same mass spectrum acquired and processed using a program employing a conventional algorithm. The conventional approach is unable to make any charge state assignments in this region of the spectrum, as is indicated by the "question marks" over the peaks of interest in the figure. FIG. 13D has the correctly labeled charge states of the original profile data as assigned by our algorithm employing the novel methods taught herein for the two overlapping charge states described above.

Figure 24A:
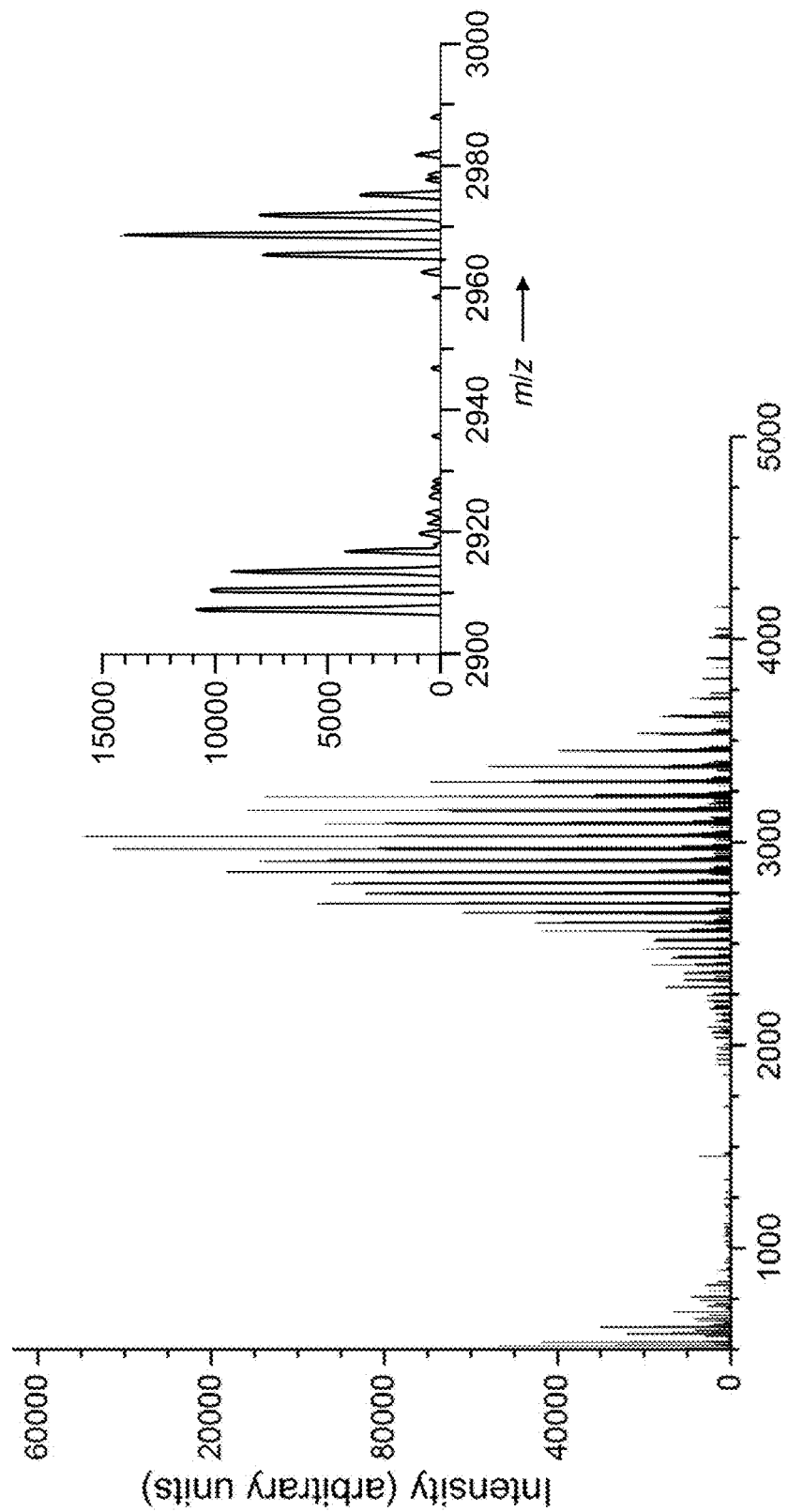
FIG. 24A is a depiction of a mass spectrum of an intact antibody having varying degrees of glycosylation (main plot) also showing (inset) an expanded portion of the spectrum illustrating the different glycoforms of the antibody.
Figure 24B:
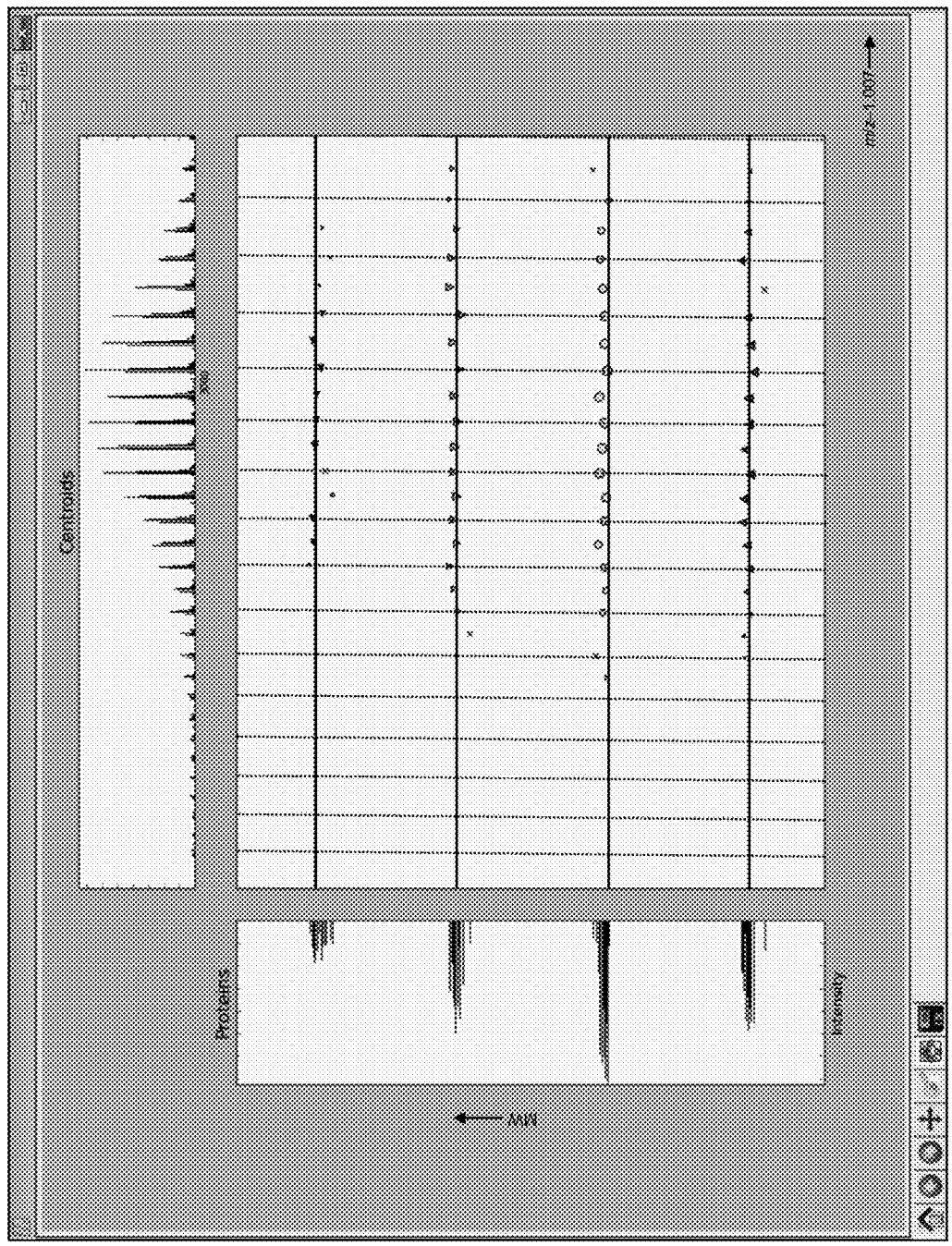
FIG. 24B is a depiction of a computer screen information display illustrating peak cluster decomposition results, as generated by computer software employing methods in accordance with the present teachings, calculated from the mass spectral data shown in FIG. 24A, showing the calculated molecular weights of the four decomposed glycoforms of the antibody ranging from 148378 Da to 148763 Da.

The program employing methods in accordance with the present teachings can also determine charge states for those peaks that do not contain individually resolved isotopes. In another example, illustrated in FIG. 24A, the mass spectrum of an intact antibody is shown with varying degrees of glycosylation. An example of the different glycoforms of the antibody are displayed in the inset of FIG. 24A. FIG. 24B illustrates the deconvoluted molecular weights of the four deconvoluted glycoforms ranging from 148378 Da to 148763 Da.

Figure 25A:
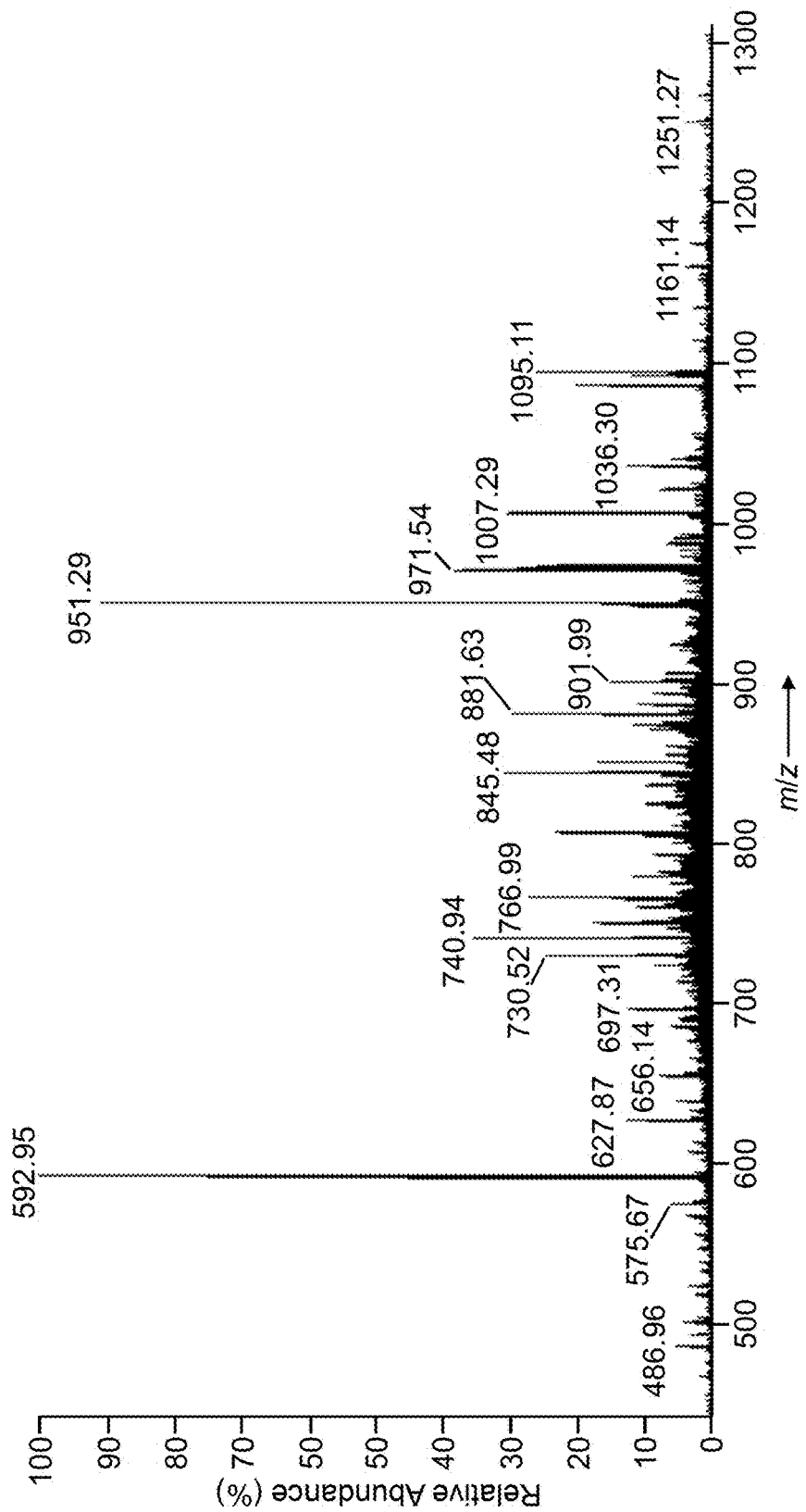
FIG. 25A is a depiction of an $MS^2$ spectrum of the protein carbonic anhydrase II, generated by collision-induced dissociation of the +26 charge state of the protein occurring at m/z=807.00 Da, showing peak assignments as determined by a conventional mass spectral analysis method.
Figure 25B:
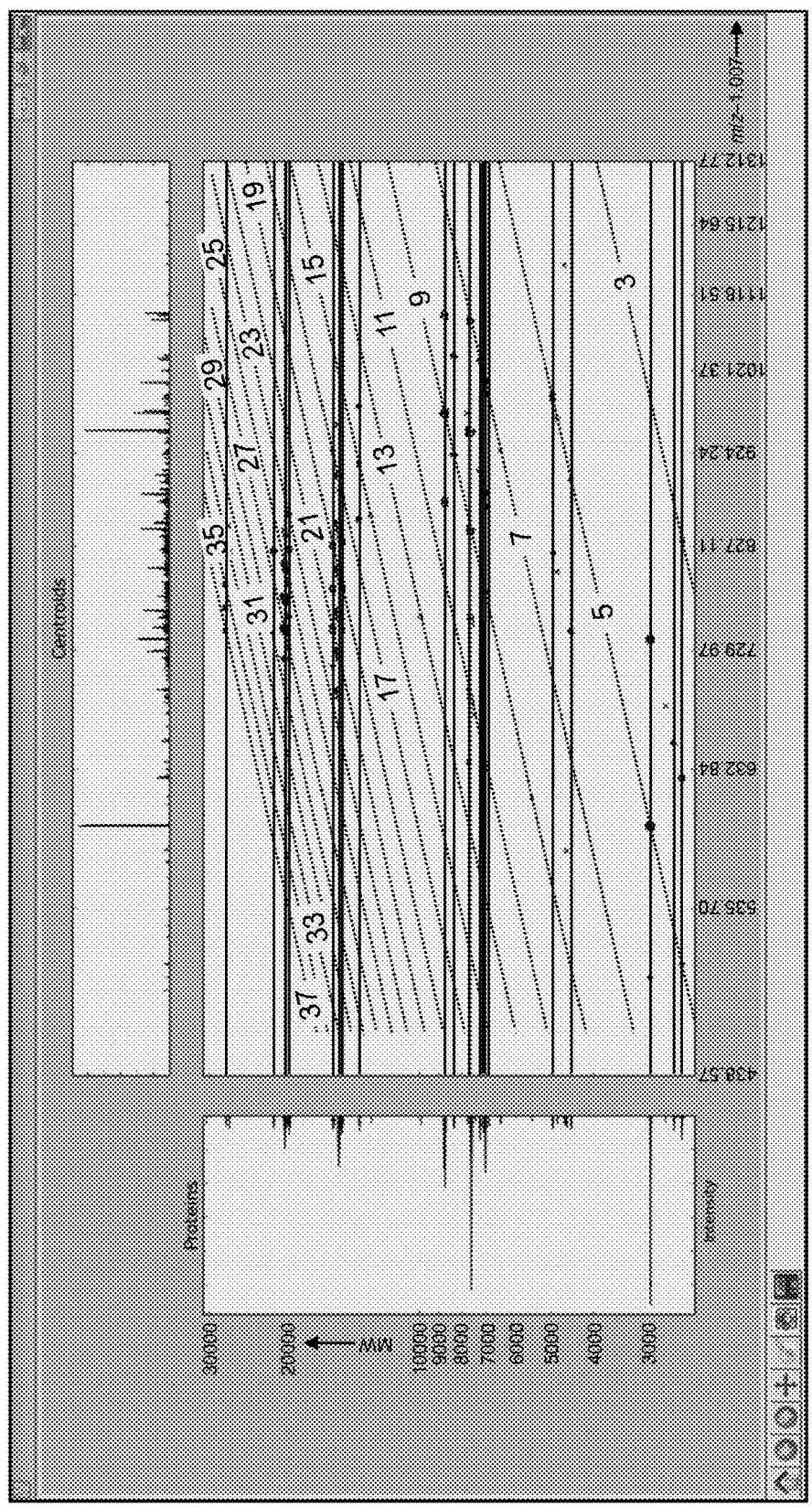
FIG. 25B is a depiction of a computer screen information display illustrating peak cluster decomposition results, as generated by computer software employing methods in accordance with the present teachings, calculated from the $MS^2$ mass spectral data shown in FIG. 25A.
Figure 25C:
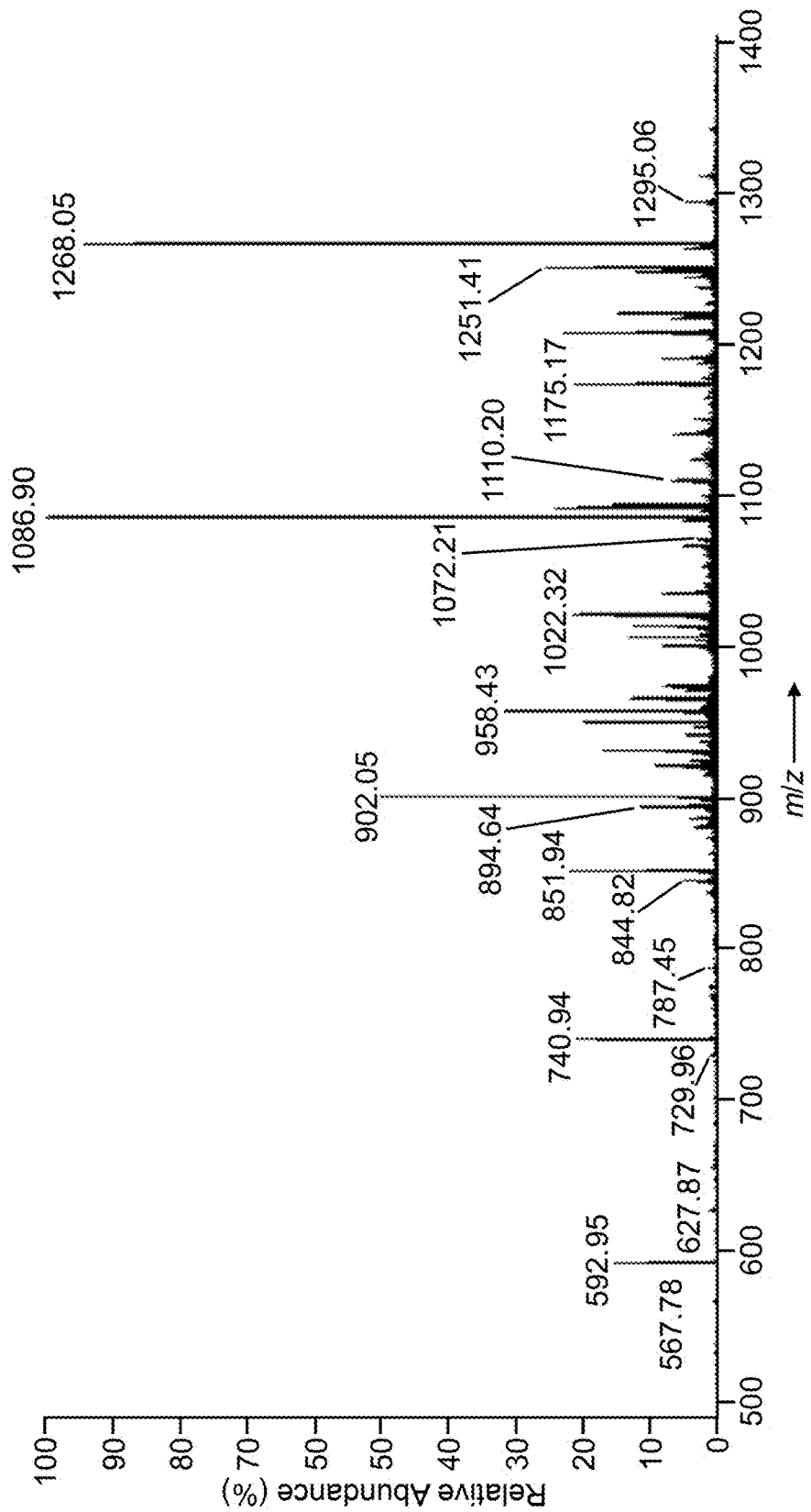
FIG. 25C is a depiction of a second $MS^2$ spectrum of the protein carbonic anhydrase II, generated by collision-induced dissociation of the +21 charge state of the protein at m/z=1001.00 Da, showing peak assignments as determined by a conventional mass spectral analysis method.
Figure 25D:
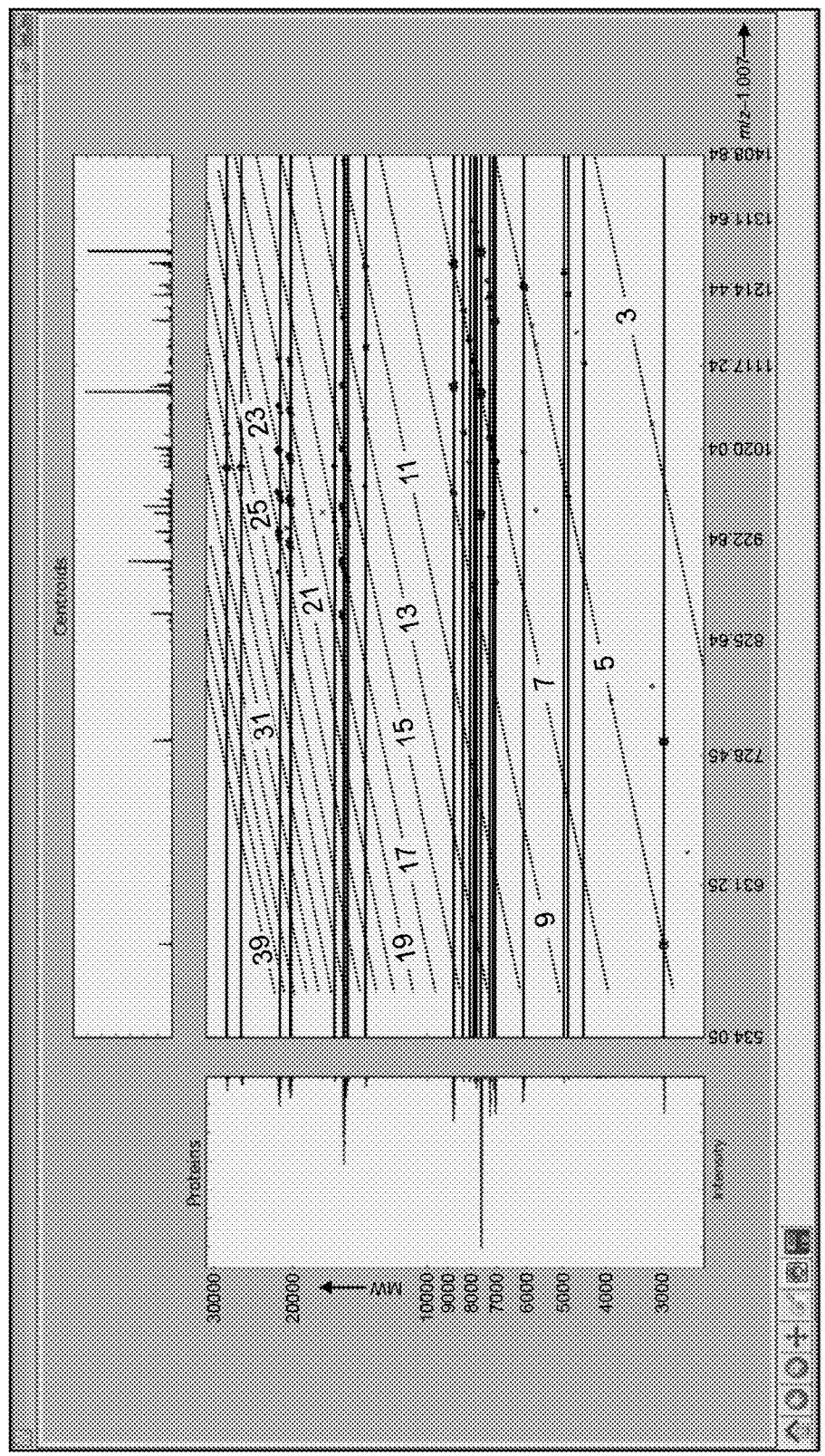
FIG. 25D is a depiction of a computer screen information display illustrating peak cluster decomposition results, as generated by computer software employing methods in accordance with the present teachings, calculated from the $MS^2$ mass spectral data shown in FIG. 25C.

The methods in accordance with the present teachings also have utility for deconvoluting tandem mass spectrometry data. In another example, as illustrated in FIGS. 25A and 25B, two charge states from the protein carbonic anhydrase II were selected for collisional activated dissociation. In FIG. 25A is shown the MS/MS spectrum and corresponding deconvolution of the +26 charge state of carbonic anhydrase II. Here 64% of the centroids were correctly identified compared to only 9% using the conventional algorithm. Exactly 50% of the centroids were clustered even in the event where many MS/MS fragments do not produce multiple charge states of the same fragment. The total number of fragment ions identified correctly was 35. FIG. 25B shows the MS/MS fragmentation and deconvolution of the +21 charge state of carbonic anhydrase II at m/z 1001. Here 74% of the centroids were clustered and 78% of the charge states were assigned correctly. A total of 49 fragments ions were identified using the program.

8. Directing Data Dependent Acquisition to Avoid Redundant Measurements

In the traditional approach to setting up a dynamic exclusion list, m/z values are placed on the list for a specified time period, which approximates the average peak width of a given compound/type of compound. When using such an approach with small molecules or peptides (i.e. tryptic peptides which typically have the same physiochemical properties), it works well to increase the dynamic range associated with the compound identification process. On the contrary, intact proteins (as are measured in top-down proteomics studies) widely vary in sizes, amino acid compositions, physiochemical properties, and 3-D structures. This variability typically leads to many more sites on the protein (than would be the case for smaller-molecule analytes) interacting with the stationary phase of a chromatographic column. The result is that some peaks may be only a few seconds wide while others can persist on the order of minutes. A typical example of the variability that can be expected is illustrated in FIG. 13, showing the varying peak profiles obtained from a single chromatographic run. Therefore, the standard approach to dynamic exclusion is not an ideal fit for top-down analysis. To rectify this problem, the present methods employ a signal intensity ranking system to determine for how long the charge states associated with a given protein should be placed on the dynamic exclusion list. In this new approach, the seed centroid of each cluster is put on the exclusion list. When a new seed centroid is proposed in subsequent $MS^1$ scan, a check is first made to determine if the new centroid clusters with any of the seed centroids presently on the selection list in step A510 (FIG. 14). If so, a check is made to determine if the intensity of the new centroid has fallen below a threshold (as a fraction of the intensity of the original seed centroid). Only when the intensity does fall below the threshold, will the original seed centroid be taken off of the exclusion list (step A515).

Alternatively, all charge states from a given protein can be placed on the exclusion list, thus eliminating selecting different charge states from the same protein for tandem MS analysis. While these charge states are on the dynamic exclusion list, the signal intensity of the peaks comprising the list are monitored until they are below a defined minimum intensity or there is an increase in signal from one of the charge states at a defined mass difference (ppm), indicating the presence of two components of differing mass and charge but the same m/z value.

What is claimed is:

1. A method for identifying the presence or absence of a protein or polypeptide analyte compound within a liquid sample comprising a mixture of compounds that includes a plurality of protein compounds or a plurality of polypeptide compounds or pluralities of both protein and polypeptide compounds, the method comprising:
    (a) introducing a portion of the liquid sample into an electrospray ionization source of a mass spectrometer;
    (b) forming positively charged ions of the mixture of compounds of the portion of the liquid sample by electrospray ionization, the positively charged ions comprising a plurality of ion species;
    (c) isolating a first subset of the ion species comprising a first mass-to-charge (m/z) ratio range that includes an m/z ratio of a particular predetermined multiply-protonated molecular species of the analyte compound;
    (d) generating a plurality of first-generation product ion species from the isolated first subset of ion species by causing the isolated first subset of ion species to be reacted, for a predetermined time duration, with reagent anions that, upon reaction, extract protons from each of one or more ion species that comprises a protonated molecular species of a protein or polypeptide compound;
    (e) generating a mass spectrum, using a mass analyzer, of either the first-generation product ion species or of second-generation product ion species generated from the first-generation product ion species;
    (f) recognizing, from the mass spectrum of either the first-generation or the second-generation product ion species, a set of one or more m/z ratios that are diagnostic of the protein or polypeptide analyte compound; and
    (g) identifying the presence of the analyte compound within the sample if the set of one or more m/z ratios is identified in the mass spectrum,
    wherein the step (f) of recognizing the set of one or more m/z ratios that are diagnostic of the protein or polypeptide analyte compound employs a mathematical analysis algorithm in which intensities of peaks observed in the mass spectrum are represented as Boolean values and the m/z value of each peak is represented by a variable, $T(m/z)$, where $T(m/z)=\ln(m/z)-M_{proton}$) and $M_{proton}$ is the mass of a proton.

2. A method as recited in claim 1, further comprising repeating the steps (a) through (e) a second time, wherein the steps (f) and (g) are performed during or prior to the second performing of the steps (a) through (e).

3. A method as recited in claim 1, further comprising repeatedly performing steps (a) through (g) a plurality of times, wherein each repetition of step (a) comprises introducing, into the electrospray ionization source, an eluate from a chromatographic column corresponding to a respective retention time.

4. A method as recited in claim 1, wherein the step (f) of recognizing the set of one or more m/z ratios that are diagnostic of the protein or polypeptide analyte compound comprises recognizing a series of m/z ratios within the mass spectrum of the first-generation product ion species that correspond to a sequence of multiply-protonated ion species of the analyte compound that are progressively charge-reduced with respect to the charge state of the particular predetermined multiply-protonated molecular species.

5. A method as recited in claim 1, wherein:
    the step (c) comprises further isolating a second subset of the ion species comprising a second m/z ratio range that includes an m/z ratio of a particular predetermined multiply-protonated molecular species of a second protein or polypeptide analyte compound;
    the step (f) comprises recognizing, from the mass spectrum of either the first-generation or the second-generation product ion species and using the mathematical analysis algorithm, a second set of one or more m/z ratios that are diagnostic of the second protein or polypeptide analyte compound; and
    the step (g) comprises identifying the presence of the second analyte compound within the sample if the second set of m/z ratios is identified in the mass spectrum.

6. A method as recited in claim 5, wherein the first m/z ratio range is identical to the second m/z ratio range.

7. A method as recited in claim 5, wherein the step (c) comprises simultaneously isolating the first subset of the ion species comprising the first m/z ratio and the second subset of the ion species comprising the second m/z ratio range such that the first and second m/z ratio ranges are non-contiguous.

8. A method as recited in claim 1, wherein the step (d) of generating a plurality of first-generation product ion species comprises causing the isolated first subset of ion species and reagent anions to be reacted for a time duration that causes the product ion species to be stable against decomposition during the subsequent generation of the mass spectrum in step (e).

9. A method as recited in claim 8, wherein the step (e) comprises generating a mass spectrum of the first-generation product ion species using a mass analyzer that generates the mass spectrum by detecting image currents caused by motions of the ions of the product ion species within an ion trap.

10. A method as recited in claim 1, wherein the step (d) of generating a plurality of first-generation product ion species includes applying a supplemental AC voltage across electrodes of an ion trap within which the isolated first subset of ion species are reacted with reagent anions, wherein a frequency of the supplemental AC voltage is such that ion-ion reaction between the reagent anions and selected first-generation product ion species is inhibited.

11. A method as recited in claim 10, wherein the frequency of the supplemental AC voltage is such that, subsequent to the execution of step (d), product ions formed from the analyte compound exist substantially as a single ion species having a particular charge state.

12. A method as recited in claim 11, wherein:
the step (e) comprises generating a mass spectrum of the first-generation product ion species; and
wherein the mass of the single ion species is greater than 20,000 Da and the charge state of the single ion species is sufficiently great such that ions of the single ion species may be detected, during the generation of the mass spectrum, by either a quadrupole mass analyzer, a Fourier transform ion cyclotron resonance mass spectrometer or an electrostatic trap mass analyzer.

13. A method as recited in claim 1, wherein the step (e) of generating a mass spectrum comprises generating a mass spectrum of second-generation product ion species, wherein the second-generation product ion species are generated by the steps of:
generating a first mass spectrum comprising a mass spectrum of the first-generation product ion species;
isolating a subset of the first-generation product ion species comprising a particular product-ion m/z ratio range, said range automatically chosen using results generated by application of the mathematical analysis algorithm to the first mass spectrum; and
fragmenting the isolated subset of the first-generation product ion species so as to form fragment ion species, wherein the fragment ion species comprise the second-generation product ion species.

14. A method as recited in claim 1, wherein the step (e) of generating a mass spectrum comprises generating a mass spectrum of second-generation product ion species, wherein the second-generation product ion species are generated by the steps of:
generating a first mass spectrum comprising a mass spectrum of the first-generation product ion species;
isolating a subset of the first-generation product ion species comprising a particular product-ion m/z ratio range, said range automatically chosen using results generated by application of the mathematical analysis algorithm to the first mass spectrum; and
causing the isolated subset of the first-generation product ion species to be reacted, for a second predetermined time duration, with the reagent anions, wherein products of reaction between the first-generation product ion species and the reagent anions comprise the second-generation product ion species.

15. A method as recited in claim 14, wherein a supplemental AC voltage is applied across electrodes of an ion trap within which the first-generation product ion species are reacted with the reagent anions, wherein a frequency of the supplemental AC voltage is such that ion-ion reaction between the reagent anions and selected product ion species is inhibited.

16. A method as recited in claim 1, further comprising generating the liquid sample comprising the mixture of compounds by a procedure comprising:
(i) culturing microorganisms or cells;
(ii) lysing the cultured microorganisms or cells; and
(iii) extracting proteins from the lysate of cultured microorganisms or cells.

17. A method as recited in claim 16, wherein the step (iii) of extracting the liquid sample from the lysate includes passing the lysate through a solid-phase-extraction apparatus.

18. A method as recited in claim 1, wherein ion charge states are assigned to a portion of the peaks of the mass spectrum by recognizing particular differences between pairs of the T(m/z) values.

19. A method as recited in claim 18, further comprising adjusting the assigned charge states such that the adjusted charge states are optimally mutually consistent.

* * * * *

UNITED STATES PATENT AND TRADEMARK OFFICE
CERTIFICATE OF CORRECTION

PATENT NO. : 10,151,758 B2
APPLICATION NO. : 15/406626
DATED : December 11, 2018
INVENTOR(S) : Ping F. Yip et al.

Page 1 of 1

It is certified that error appears in the above-identified patent and that said Letters Patent is hereby corrected as shown below:

In the Claims

Claim 1, Column 70, Line 7-8:
Replace "..., where $T(m/z) = \ln(m/z) - M_{proton}$ ..."
With --..., where $T(m/z) = \ln((m/z) - M_{proton})$ ...--

Signed and Sealed this
Twenty-seventh Day of August, 2019

Andrei Iancu
*Director of the United States Patent and Trademark Office*